US012751719B2

(12) United States Patent
Kawaura et al.

(10) Patent No.: US 12,751,719 B2
(45) Date of Patent: Oct. 6, 2026

(54) COMPRESSION DEVICE AND COMPRESSION METHOD

(71) Applicant: TERUMO KABUSHIKI KAISHA, Tokyo (JP)

(72) Inventors: Masakatsu Kawaura, Mountain View, CA (US); Yuki Soma, Mountain View, CA (US); Shuji Uemura, Mountain View, CA (US); Daniel W. Kaiser, East Palo Alto, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 115 days.

(21) Appl. No.: 18/952,142

(22) Filed: Nov. 19, 2024

(65) Prior Publication Data

US 2025/0072904 A1 Mar. 6, 2025

Related U.S. Application Data

(63) Continuation of application No. 17/098,951, filed on Nov. 16, 2020, now Pat. No. 12,161,345, which is a (Continued)

(30) Foreign Application Priority Data

May 16, 2018 (JP) ................................ 2018-094955

(51) Int. Cl.

*A61B 17/135* (2006.01)
*A61B 17/00* (2006.01)

(Continued)

(52) U.S. Cl.

CPC ........ *A61B 17/135* (2013.01); *A61B 17/0057* (2013.01); *A61B 17/085* (2013.01);

(Continued)

(58) Field of Classification Search

CPC ................ A61B 17/135; A61B 17/325; A61B 2017/12004; A61F 2013/00468

See application file for complete search history.

(56) References Cited

U.S. PATENT DOCUMENTS

| | | |
|---|---|---|
| 3,490,448 A | 1/1970 | Grubb |
| 3,630,195 A | 12/1971 | Santomieri |

(Continued)

FOREIGN PATENT DOCUMENTS

| | | |
|---|---|---|
| CN | 205832007 U | 12/2016 |
| CN | 205849496 U | 1/2017 |

(Continued)

OTHER PUBLICATIONS

An English Translation of the International Search Report (Form PCT/ISA/210) and the Written Opinion of the International Searching Authority (Form PCT/ISA/237) issued on Jun. 18, 2019, by the Japanese Patent Office in corresponding International Application No. PCT/JP2019/019389, 8 pages.

(Continued)

*Primary Examiner* — Alexander J Orkin
(74) *Attorney, Agent, or Firm* — BUCHANAN INGERSOLL & ROONEY PC

(57) ABSTRACT

A compression device includes an adhesion sheet including an adhesion surface; and a compression member mounted on the adhesion sheet and configured to compress a biological surface. The compression member includes a fixing portion fixed to the adhesion sheet on a side of the sheet opposite the adhesion surface in a thickness direction, and a compression main body portion provided in a portion of the compression member, in a plan view seen along the thickness direction, that does not overlap the adhesion sheet. The compression main body is configured to protrude or be protrusible further toward one side in the thickness direction than the adhesion surface. The adhesion sheet includes a first portion to which (Continued)

the fixing portion is fixed and a second portion to which the fixing portion is not fixed. The second portion is provided on at least a compression main body portion side of the adhesion sheet.

20 Claims, 34 Drawing Sheets

Related U.S. Application Data continuation of application No. PCT/JP2019/019389, filed on May 15, 2019.

(51) Int. Cl.
*A61B 17/08* (2006.01)
*A61B 17/12* (2006.01)

(52) U.S. Cl.
CPC ............... *A61B 2017/00557* (2013.01); *A61B 2017/00951* (2013.01); *A61B 2017/12004* (2013.01)

(56) References Cited

U.S. PATENT DOCUMENTS

| | | | |
|---|---|---|---|
| 4,224,945 | A | 9/1980 | Cohen |
| 5,690,610 | A | 11/1997 | Ito et al. |
| 5,792,173 | A | 8/1998 | Breen et al. |
| 5,891,074 | A | 4/1999 | Cesarczyk |
| 6,007,562 | A | 12/1999 | Harren et al. |
| 6,074,356 | A | 6/2000 | Starkey et al. |
| 6,316,686 | B1 | 11/2001 | Byrd |
| 6,638,296 | B2 | 10/2003 | Levinson |
| 2004/0068290 | A1 | 4/2004 | Bates et al. |
| 2005/0125025 | A1 | 6/2005 | Rioux |
| 2007/0066926 | A1 | 3/2007 | Utterberg et al. |
| 2009/0281565 | A1 | 11/2009 | Mcneese |
| 2012/0016410 | A1 | 1/2012 | Belson et al. |
| 2012/0116444 | A1 | 5/2012 | Zodnik et al. |
| 2012/0197204 | A1 | 8/2012 | Helm, Jr. |
| 2015/0224285 | A1 | 8/2015 | Howell et al. |
| 2018/0008280 | A1 | 1/2018 | Clark |
| 2018/0147092 | A1 | 5/2018 | Krensky |
| 2021/0059686 | A1 | 3/2021 | Kawaura et al. |

FOREIGN PATENT DOCUMENTS

| | | | |
|---|---|---|---|
| JP | H05-277126 | A | 10/1993 |
| JP | 2005-521464 | A | 7/2005 |
| JP | 3186252 | U | 9/2013 |
| JP | 2018-033602 | A | 3/2018 |
| KR | 20110088899 | A | 8/2011 |
| WO | 97/06735 | A1 | 2/1997 |

OTHER PUBLICATIONS

International Search Report (PCT/ISA/210) issued on Jun. 18, 2019, by the Japan Patent Office as the International Searching Authority for International Application No. PCT/JP2019/019389.
Office Action (Notice of Reasons for Refusal) issued on Jan. 23, 2024, in corresponding Japanese Patent Application No. 2023-102758 and English translation of the Office Action, 12 pages.
Office Action (The First Office Action) issued May 24, 2023, by the National Intellectual Property Administration, P. R. China in corresponding Chinese Patent Application No. 201980024888.3 and an English translation of the Office Action, 15 pages.
Extended European Search Report issued Jul. 23, 2021, by the European Patent Office in corresponding European Patent Application No. 19804504.9, 9 pages.
Written Opinion (PCT/ISA/237) issued on Jun. 18, 2019, by the Japan Patent Office as the International Searching Authority for International Application No. PCT/JP2019/019389.

COMPRESSION DEVICE AND COMPRESSION METHOD

CROSS-REFERENCES TO RELATED APPLICATIONS

This application is a continuation of U.S. patent application Ser. No. 17/098,951 filed on Nov. 16, 2020, which is a continuation of International Application No. PCT/JP2019/019389 filed on May 15, 2019, which claims priority to Japanese Application No. 2018-094955 filed on May 16, 2018, the entire content of all of which is incorporated herein by reference.

FIELD OF THE INVENTION

The present disclosure generally relates to a compression device and a compression method.

BACKGROUND DISCUSSION

In recent years, in medical institutions, various forms of examinations or treatments are performed using an elongated hollow tubular medical device which is called a catheter. The catheter is percutaneously inserted into a blood vessel from a puncture site, which is formed in the wrist, the inguinal region, or the like, to be delivered to a site to be examined or treated through the blood vessel. After the examination or treatment by a health care worker is completed, the catheter or a sheath used to introduce the catheter is removed from the puncture site, and hemostasis is performed on the puncture site.

JP 2005-521464 A discloses a dressing as a compression device that compresses a wound of a patient after a sheath is removed. The dressing disclosed in JP 2005-521464 A includes an inflatable bladder having a contracted state where a membrane is adjacent to an end wall and an inflated state where the membrane is spaced apart from the end wall. In addition, the dressing disclosed in JP 2005-521464 A includes holding means that holds the bladder against the skin of the patient at a position where the wound is substantially covered. JP 2005-521464 A discloses that the holding means includes a flexible web that is connected to the end wall of the bladder to protrude outward from the end wall of the bladder, and an adhesion layer that adheres to the skin of the patient is provided on one surface of the flexible web.

SUMMARY

In the dressing as a compression device described in JP 2005-521464 A, the adhesion layer provided on the one side of the flexible web adheres to the skin as a biological surface of the patient and the bladder is brought into the inflated state, so that the wound of the patient can be compressed by the bladder.

However, in the dressing described in JP 2005-521464 A, when the wound of the patient is compressed by the bladder, due to a depression of the skin caused by compression and reaction force received from the skin, the adhesion layer provided on the one side of the flexible web is likely to peel off in the vicinity of the bladder. When the adhesion layer peels off, a desired compression force of the bladder may not be obtained.

The present disclosure provides a compression device that is unlikely to peel off from a biological surface. In addition, the present disclosure provides a new compression method.

In addition, since the dressing as a compression device described in JP 2005-521464 A compresses a blood vessel to perform hemostasis, there is a possibility that the blood vessel is damaged. The compression device and compression method disclosed here relatively easily narrow or obstruct a perforation, which is formed between a biological surface and a vein, without obstructing the vein.

In addition, since the disposition of the dressing as a compression device described in JP 2005-521464 A is visually performed, there is a possibility that compression cannot be performed at a proper position. The compression device disclosed here rather easily compresses a proper position on a biological surface.

According to a first aspect of the present disclosure, a compression device comprises an adhesion sheet and a compression member. The adhesion sheet includes an adhesion surface that is adherable to a biological surface, and the adhesion sheet possesses a thickness extending in a thickness direction of the adhesion sheet between one side of the adhesion sheet and an other side of the adhesion sheet that face in opposite directions. An adhesion surface is fixed to the adhesion sheet and is on the one side of the of the adhesion sheet in the thickness direction. The compression member is mounted on the adhesion sheet and is configured to compress the biological surface when the adhesion surface of the adhesion sheet is adhered to the biological surface. The compression member comprises a fixing portion and a compression main body portion. The fixing portion is fixed to the adhesion sheet on the other side of the adhesion sheet in the thickness direction. The compression main body portion is provided in a portion of the compression member in a plan view of the compression device seen along the thickness direction, with the portion of the compression member in which the compression main body portion is provided being positioned to not overlap the adhesion sheet in the plan view. The compression main body portion includes a part that is configured to protrude further toward the one side of the adhesion sheet in the thickness direction than the adhesion surface of the adhesion sheet. The compression main body portion comprises: a housing portion, a support portion and an arm portion. The housing portion accommodates the part of the compression main body that is configured to protrude further toward the one side of the adhesion sheet in the thickness direction than the adhesion surface of the adhesion sheet, and the housing portion is located so that the housing portion does not overlap the adhesion sheet in the plan view. The support portion is located in overlapping relation to the adhesion sheet in the plan view, and the support portion is fixed to the adhesive sheet on the other side of the adhesive sheet in the thickness direction. The arm portion connects the housing portion and the support portion. The housing portion and the arm portion collectively constitute a first member that is configured to be disassembled from the support portion and that is configured to be connected to the support portion after being disassembled from the support portion.

According to another aspect of the present disclosure, a compression device comprises an adhesion sheet possessing a thickness extending in a thickness direction of the adhesion sheet between a first side of the adhesion sheet and an opposite second side of the adhesion sheet, with the adhesion sheet including an adhesion surface on the first side of the adhesion sheet to contact a biological surface and adhere the compression device to the biological surface. The adhesion sheet is an annular-shaped adhesion sheet as seen in a plan view, and the annular-shaped adhesion sheet has, as seen in the plan view, an inner periphery surrounding a region that is devoid of the adhesion sheet. An upstanding support portion is fixed to the annular-shaped adhesion sheet on the second side of the annular-shaped adhesion sheet. An expandable expander is configured to compress the biological surface when the adhesion surface of the annular-shaped adhesion sheet is adhered to the biological surface. The expandable expander is mounted on a holder so that the expandable expander is positioned, as seen in the plan view, in the region that is surrounded by the inner periphery of the annular-shaped adhesion sheet and that is devoid of the adhesion sheet. The expandable expander is configured to protrude further toward the first side of the adhesion sheet in the thickness direction than the adhesion surface of the adhesion sheet. An arm portion removably connects the holder and the expandable expander to the support portion so that the holder and the expandable expander are disassemblable from the support portion.

According to a further aspect of the present disclosure, a compression device comprises an adhesion sheet possessing a thickness extending in a thickness direction of the adhesion sheet between a first side of the adhesion sheet and an opposite second side of the adhesion sheet, with the adhesion sheet including an adhesion surface on the first side of the adhesion sheet to contact a biological surface and adhere the compression device to the biological surface. The adhesion sheet is an annular-shaped adhesion sheet as seen in a plan view, and the annular-shaped adhesion sheet has, as seen in the plan view, an inner periphery surrounding a region that is devoid of the adhesion sheet. An upstanding support portion is fixed to the annular-shaped adhesion sheet on the second side of the annular-shaped adhesion sheet. An expandable expander is mounted on a holder, and an arm portion is configured to removably connect the holder to the upstanding support portion so that: i) the expandable expander mounted on the holder is positioned, as seen in the plan view, in the region that is surrounded by the inner periphery of the annular-shaped adhesion sheet and that is devoid of the adhesion sheet; and ii) the arm portion when connected to the support portion is separable from the support portion to disassemble the holder and the expandable expander from the support portion. The expandable expander is configured to protrude further toward the first side of the adhesion sheet in the thickness direction than the adhesion surface of the adhesion sheet when the holder is connected to the upstanding support portion by the arm portion.

The compression device is unlikely to peel off from a biological surface. The compression device is able to relatively easily narrow or obstruct a perforation, which is formed between a biological surface and a vein, without obstructing the vein. Also, the compression device can relatively easily compress a proper position on the biological surface.

DETAILED DESCRIPTION

Figure 1:
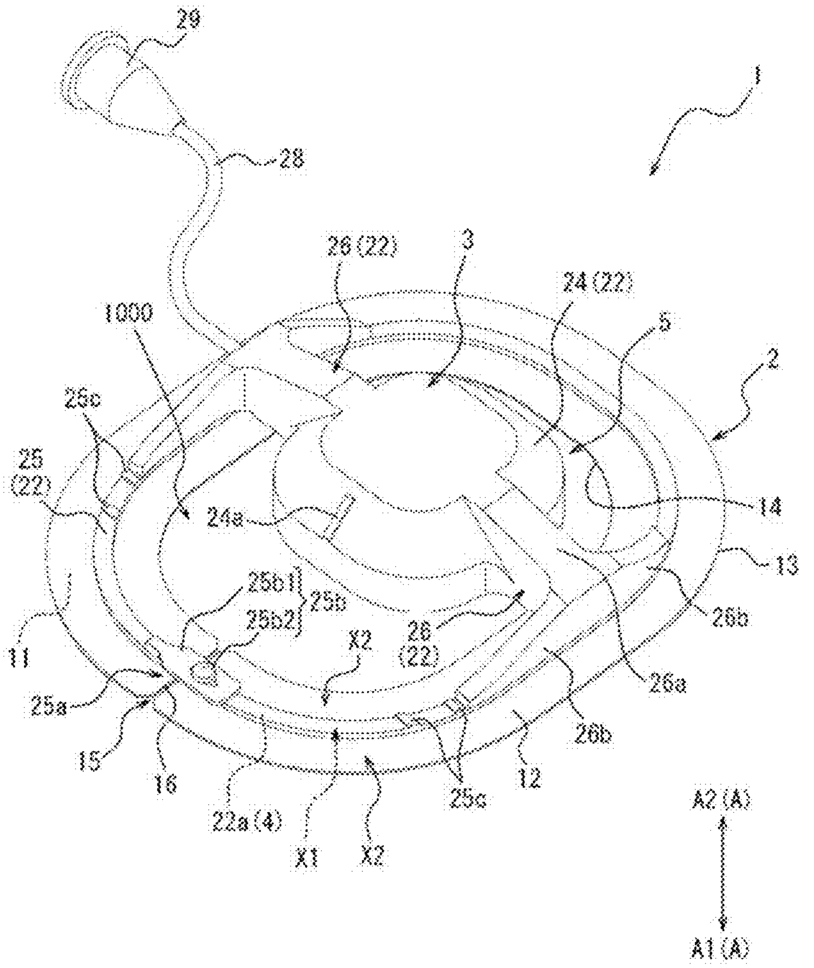
FIG. 1 is a perspective view of a compression device as one embodiment.

Set forth below with reference to the accompanying drawings is a detailed description of embodiments of a compression device and a compression method representing examples of the inventive compression device and compression method disclosed here. The dimensions or scales on the drawings may be exaggerated or different from actuality/reality for convenience of description and illustration. Common features in the different drawing figures are denoted by the same reference numerals.

First Embodiment

Figure 2:
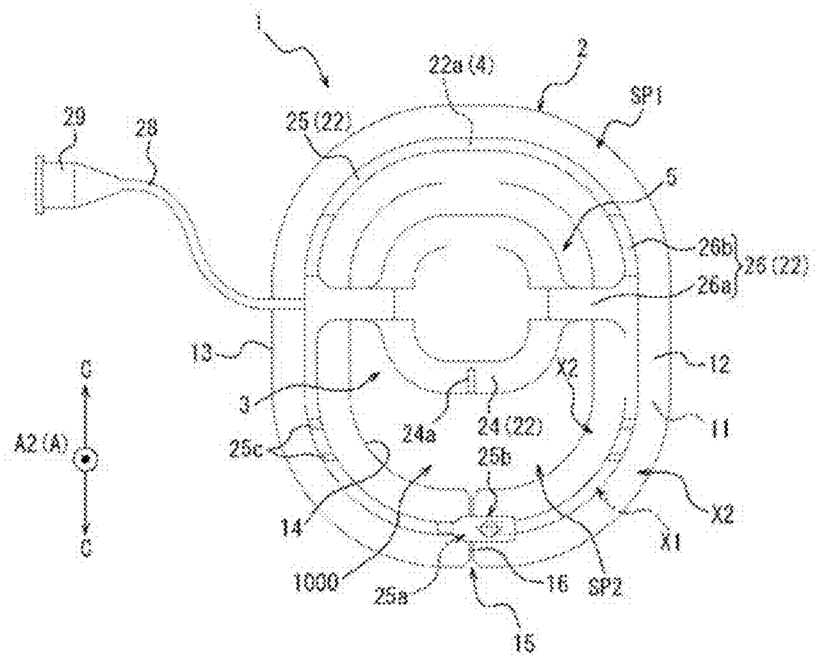
FIG. 2 is a top view of the compression device illustrated in FIG. 1.
Figure 3:
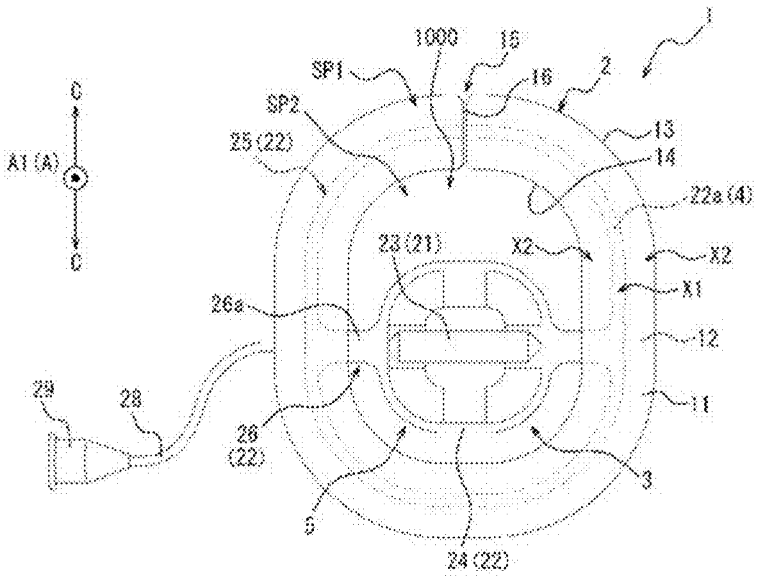
FIG. 3 is a bottom view of the compression device illustrated in FIG. 1.
Figure 4A:
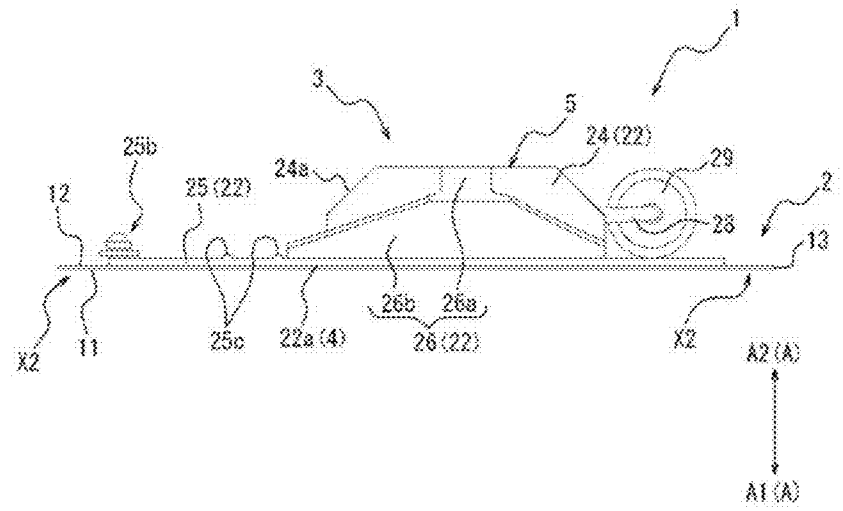
FIG. 4A is a side view of the compression device illustrated in FIG. 1, and is a view illustrating a state where an inflator is in a retracted form.
Figure 4B:
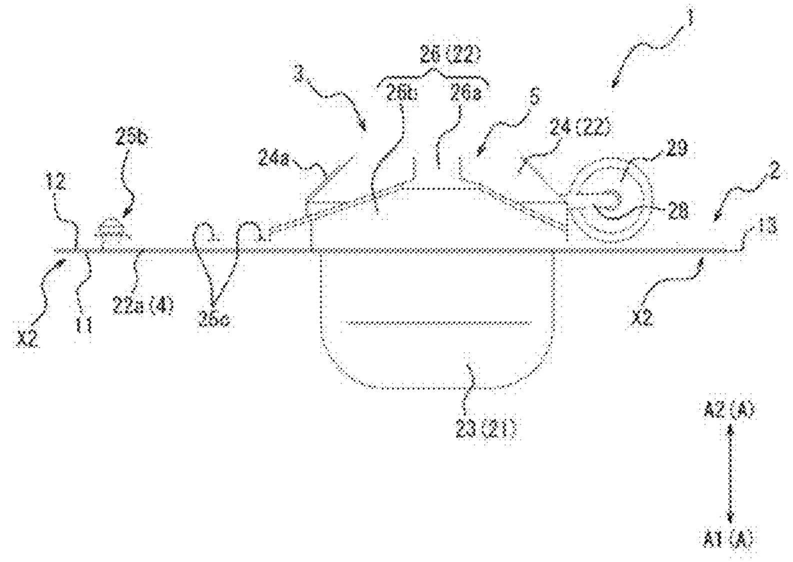
FIG. 4B is a side view of the compression device illustrated in FIG. 1, and is a view illustrating a state where the inflator is in a protruding form.

FIGS. 1 to 4B are views illustrating a compression device 1 according to one embodiment. Specifically, FIG. 1 is a perspective view of the compression device 1. FIGS. 2 and 3 are plan views of the compression device 1. Specifically, FIG. 2 is a top view of the compression device 1. FIG. 3 is a bottom view of the compression device 1. FIGS. 4A and 4B are side views of the compression device 1. As will be described in detail later, FIGS. 4A and 4B illustrate different states of the compression device 1.

The compression device 1 includes an adhesion sheet or adhesive sheet 2, serving as a mounting member, and a compression member 3.

The adhesion sheet 2 includes an adhesion surface or adhesive surface 11, which is adherable to a biological surface (e.g., a surface of a living body such as the outer surface of a patient's body), on one side of a thickness direction A. The compression member 3 is mounted on the adhesion sheet 2, and can compress the biological surface or apply a compressive force in a state where the adhesion surface 11 is adhered to the biological surface. In such a manner, when the adhesion surface 11 is adhered to the biological surface, the position of the compression device 1 on the biological surface is fixed. In addition, in a state where the position of the compression device 1 is fixed on the biological surface, a predetermined site on the biological surface can be compressed by the compression member 3. Examples of the predetermined site on the biological surface include a wound hole or the vicinity of the wound hole which is formed when a medical device such as a puncture needle, a catheter, or a sheath is inserted into or punctures a blood vessel of a living body. Hemostasis can be performed by removing the above-described medical device from the living body and then compressing the wound hole or the vicinity of the wound hole on the biological surface with the compression member 3.

Hereinafter, each member and each portion of the compression device 1 will be described in detail.

<Adhesion sheet 2>

As described above, the adhesion sheet 2 includes the adhesion surface 11 on the one side of the adhesion surface 11 in the thickness direction A of the adhesion surface 11. In addition, the other side of the adhesion sheet 2 in the thickness direction A includes a mounting surface 12 on which the compression member 3 is mounted. The compression member 3 is thus mounted on the opposite side of the adhesion sheet 2 from the adhesion surface 11. The adhesion sheet 2 is flexible. For this reason, the adhesion sheet 2 is deformable along the shape of the biological surface so that the adhesion sheet 2 can generally conform to the shape of the biological surface. In addition, the adhesion surface 11 easily follows a deformation of the biological surface. As a result, the compression device 1 can be suppressed from unintentionally peeling from the biological surface.

More specifically, the adhesion surface 11 of the adhesion sheet 2 of the present embodiment is formed of a lower surface of the adhesion sheet 2 (i.e., the lower surface of the adhesion sheet 2 is the adhesion surface 11). In addition, the mounting surface 12 of the adhesion sheet 2 of the present embodiment is formed of an upper surface of the adhesion sheet 2 (i.e., the upper surface of the adhesion sheet 2 is the mounting surface 12).

Hereinafter, for convenience of description, the one thickness direction A, which is a direction from the mounting surface 12 toward the adhesion surface 11 in the thickness direction A, is referred to as a "downward direction A1". In addition, for convenience of description, the other thickness direction A, which is a direction from the adhesion surface 11 toward the mounting surface 12 in the thickness direction A, is referred to as an "upward direction A2". Furthermore, among plan views (refer to FIGS. 2 and 3) of the compression device 1 as seen along the thickness direction A of the adhesion sheet 2, for convenience of description, a plan view (refer to FIG. 2) seen from the mounting surface 12 side of the adhesion sheet 2 is referred to as a "top view". In addition, among the plan views (refer to FIGS. 2 and 3) of the compression device 1 as seen along the thickness direction A of the adhesion sheet 2, for convenience of description, a plan view (refer to FIG. 3) seen from the adhesion surface 11 side of the adhesion sheet 2 is simply referred to as a "bottom view".

The adhesion sheet 2 is formed of a plurality of layers including, for example, a base material layer, an adhesion layer, and a surface layer.

The base material layer is made of, for example, a thin resin sheet. More specifically, the base material layer is made of, for example, a white spunlace non-woven fabric made of polyester fibers, and the thickness of the base material layer is in a range of 5 μm to 150 μm, for example, 30 μm. The material from which the base material layer is fabricated is not limited to polyester, and for example, acrylic polymer, polyethylene, ethylene-vinyl acetate copolymer, polyurethane, polyamide derivative, and the like may be used.

The adhesion layer is made of an adhesive such as a rubber adhesive, an acrylic adhesive, or a silicone adhesive. The adhesion layer is laminated on the base material layer directly or indirectly with another layer interposed therebetween. The adhesion surface 11 of the adhesion sheet 2 of the present embodiment is formed of the adhesion layer.

The surface layer is made of, for example, a resin having a thickness of approximately 5 μm to 50 μm. More specifically, examples of materials which may be sued to fabricate the surface layer include polyester, polyamide, polyamide-imide, polyethylene, polypropylene, polycarbonate, polyurethane, polyvinyl chloride, fluororesin, and the like. The surface layer is laminated on an opposite side of the base material layer from the adhesion layer with the base material layer interposed therebetween, directly or indirectly with another layer interposed between the surface layer and the base material layer. The mounting surface 12 of the adhesion sheet 2 of the present embodiment is formed of the surface layer.

The adhesion sheet 2 is not limited to a three-layer structure including the base material layer, the adhesion layer, and the surface layer, and may have, for example, four or more layers of structure further including other layers. In addition, the adhesion sheet 2 may be formed of only two layers including the base material layer and the adhesion layer.

In such a manner, the adhesion sheet 2 of the present embodiment is made of non-woven tape having one surface to which a pressure sensitive adhesive as an adhesive is applied, but may be made of double-sided tape in which the adhesion layers are provided on both sides of the base material layer. When the adhesion sheet is made of the double-sided tape, a fixing portion 4 (to be described later) of the compression member 3 adheres to one adhesion layer of the adhesion sheet, so that the compression member 3 can be fixed to the adhesion sheet 2.

As illustrated in FIGS. 2 and 3, the adhesion sheet 2 of the present embodiment extends in an annular shape. In other words, the annular-shaped adhesion sheet 2 of the present embodiment defines a central opening region.

In addition, a slit 15 extending from an outer edge 13 to an inner edge 14 is formed in the adhesion sheet 2 of the present embodiment. In a plan view (refer to FIGS. 2 and 3), the slit 15 extends in a radial direction C of a circle centered around the center of the adhesion sheet 2 (hereinafter, simply referred to as a "radial direction C"). In other words, both end edges 16 of the adhesion sheet 2, in which the two end edges 16 are opposite to each other with the slit 15 interposed therebetween, extend in parallel to each other along the radial direction C. An extending direction of the slit 15 is not limited to the radial direction C, and the slit 15 may be a slit extending in a direction that is inclined with respect to the radial direction C. Since the slit 15 is provided, the medical device such as a catheter or a sheath is movable from outside the adhesion sheet 2 into the central opening region through the slit 15.

As will be described in detail later, the adhesion sheet 2 includes a first portion X1 to which the fixing portion 4 (to be described later) of the compression member 3 is fixed and a second portion X2 to which the fixing portion 4 is not fixed. The compression device 1 includes the second portion X2 on at least a compression main body portion 5 side (to be described later) of the adhesion sheet 2.

In a state before the adhesion surface 11 is adhered to the biological surface (hereinafter, referred to as a "pre-use state"), the adhesion surface 11 of the adhesion sheet 2 is covered with a separation sheet 27 (to be described later) (refer to FIG. 6C). When the adhesion sheet 2 is to be adhered to the biological surface, the separation sheet 27 is peeled off and removed from the adhesion surface 11 by a user. Since the adhesion surface 11 is exposed due to the removal of the separation sheet 27 from the adhesion surface 11, the adhesion surface 11 of the adhesion sheet 2 is adherable to the biological surface. The separation sheet 27 can be made of, for example, separation paper or a resin sheet material. In FIGS. 1 to 4B, the separation sheet 27 is unillustrated.

<Compression Member 3>

The compression member 3 is disposed across an in-edge region SP1 of the adhesion sheet 2, which is located to overlap the adhesion sheet 2 in a plan view (refer to FIGS. 2 and 3) and an out-of-edge region SP2 of the adhesion sheet 2, which is located to not overlap the adhesion sheet 2 in a plan view (refer to FIGS. 2 and 3). In other words, the compression member 3 includes a portion which overlaps the adhesion sheet 2 and a portion which does not overlap the adhesion sheet 2 in a plan view (refer to FIGS. 2 and 3). The in-edge region SP1 for the compression member 3 of the present embodiment is an annular region interposed between the outer edge 13 and the inner edge 14 of the adhesion sheet 2 in a plan view (refer to FIGS. 2 and 3). In addition, the out-of-edge region SP2 for the compression member 3 of the present embodiment is the central opening region inside the inner edge 14 in a plan view (refer to FIGS. 2 and 3). Namely, the central opening region of the present embodiment is a part of the out-of-edge region SP2.

More specifically, as illustrated in FIGS. 2 and 3, in a plan view, the compression member 3 of the present embodiment is disposed across the central opening region as the out-of-edge region SP2, and the in-edge region SP1. In addition, in a plan view, the compression member 3 of the present embodiment crosses the inner edge 14 of the adhesion sheet 2 at a plurality (two in the present embodiment) of positions. As will be described in detail later, the compression member 3 of the present embodiment can compress the biological surface in the central opening region of the adhesion sheet 2.

The compression member 3 includes the fixing portion 4 and the compression main body portion 5.

In a plan view (refer to FIG. 2 and the like), the fixing portion 4 is located in the in-edge region SP1. Namely, in a plan view (refer to FIG. 2 and the like), the fixing portion 4 is disposed at a position to overlap the adhesion sheet 2. In addition, the fixing portion 4 is fixed to the adhesion sheet 2 on the mounting surface 12 side of the adhesion sheet 2 in the thickness direction A. The fixing portion 4 of the present embodiment is fixed to the mounting surface 12 by, for example, adhesion, fusion, or the like; however, the position where the fixing portion 4 is fixed to a portion of the adhesion sheet 2 is not particularly limited as long as the portion is located closer to the upward direction A2 than the adhesion surface 11. Therefore, the fixing portion 4 may be fixed to a layer that is located closer to the downward direction A1 than the mounting surface 12. By the way, when the fixing portion 4 of the compression member 3 is configured to be fixed to the mounting surface 12 of the adhesion sheet 2 by adhesion, fusion, or the like, the compression member 3 is easily mountable on the adhesion sheet 2.

The fixing portion 4 of the present embodiment is formed of a contact surface 22*a* of a portion of the compression member 3, the portion being located in the in-edge region SP1 in a plan view (refer to FIG. 2 and the like) and the contact surface 22*a* being in contact with the mounting surface 12 of the adhesion sheet 2. More specifically, the fixing portion 4 of the present embodiment is formed of the contact surface 22*a* of a support portion 25 (to be described later) of the compression member 3, the contact surface 22*a* being in contact with the mounting surface 12 of the adhesion sheet 2. The details will be described later (refer to FIG. 2 and the like).

In a plan view (refer to FIGS. 2 and 3), the compression main body portion 5 is located in the out-of-edge region SP2. Namely, in a plan view (refer to FIGS. 2 and 3), the compression main body portion 5 is disposed at a position in which the compression main body portion 5 does not overlap the adhesion sheet 2. In other words, in a plan view (refer to FIGS. 2 and 3), the compression main body portion 5 is provided in the portion of the compression member 3, the portion not overlapping the adhesion sheet 2. In addition, the compression main body portion 5 is protrusible, or is configured to be able to protrude or project, further toward the downward direction A1 in the thickness direction A than the adhesion surface 11 of the adhesion sheet 2. That is, the compression main body portion 5 can protrude, in the downward direction A1 in the thickness direction A, beyond the adhesion surface 11 of the adhesion sheet 2.

The compression main body portion 5 of the present embodiment includes an expander 21 (to be described later) that is expandable toward the biological surface in a state where the adhesion sheet 2 is adhered to the biological surface. In a state where the adhesion sheet 2 is adhered to the biological surface, the expander 21 can be changed in form between a retracted form in which the expander 21 is located closer to the upward direction A2 than the adhesion surface 11 of the adhesion sheet 2 in the thickness direction A and a protruding or projecting form in which the expander 21 is located closer to the downward direction A1 than the adhesion surface 11 of the adhesion sheet 2 in the thickness direction A. FIG. 4A illustrates the retracted form of the expander 21. FIG. 4B illustrates the protruding or projecting form of the expander 21. When the expander 21 is changed in form from the retracted form (refer to FIG. 4A) to the protruding form (refer to FIG. 4B), the compression main body portion 5 of the present embodiment is protrusible, or is configured to be able to protrude or project, further toward the downward direction A1 in the thickness direction A than the adhesion surface 11 of the adhesion sheet 2. Therefore, the compression main body portion 5 can press and compress the biological surface in the out-of-edge region SP2 in a state where the adhesion sheet 2 is adhered to the biological surface. The expander 21 will be described in detail later.

As will be described later, the compression main body portion 5 (refer to FIG. 30) may protrude further toward the downward direction A1 in the thickness direction A than an adhesion surface 811 (refer to FIG. 30) of an adhesion sheet 802 (refer to FIG. 30). The compression main body portion 5 described above will be described in detail later.

<First Portion X1 and Second Portion X2 of Adhesion Sheet 2>

As described above, the adhesion sheet 2 includes the first portion X1 to which the fixing portion 4 of the compression member 3 is fixed and the second portion X2 to which the fixing portion 4 of the compression member 3 is not fixed.

More specifically, the first portion X1 of the present embodiment is a portion that is in contact with the contact surface 22*a* as the fixing portion 4 of the compression member 3. In addition, the second portion X2 of the present embodiment is a portion that is not in contact with the contact surface 22*a* as the fixing portion 4 of the compression member 3.

As illustrated in FIGS. 1 to 3, at least a part of the second portion X2 is located on at least the compression main body portion 5 side of the adhesion sheet 2. Namely, in the adhesion sheet 2 of the compression device 1, the second portion X2 is provided on at least the compression main body portion 5 side with respect to the first portion X1 of the adhesion sheet 2. More specifically, in the adhesion sheet 2 of the present embodiment, the second portion X2 that continuously extends from the first portion X1 is provided on at least the compression main body portion 5 side with respect to the first portion X1 of the adhesion sheet 2. Namely, the second portion X2 of the present embodiment includes at least a portion of the adhesion sheet 2, which extends from the first portion X1 to the compression main body portion 5 side.

In the present embodiment, the adhesion layer as an adhesion portion which is adherable to the biological surface is provided in the entire region of the adhesion surface 11; however, the present disclosure is not limited to this configuration. An adhesion portion made of an adhesive or the like is provided in at least a part of the adhesion surface 11 at a position corresponding to the first portion X1. In addition, an adhesion portion made of an adhesive or the like is provided in at least a part of the adhesion surface 11 at a position that corresponds to the second portion X2 located on the compression main body portion 5 side with respect to the first portion X1.

In other words, in a plan view (refer to FIG. 2 and the like), an edge of the adhesion sheet 2 and an adhesion region in the adhesion surface 11 of the adhesion sheet 2 are located between the fixing portion 4 and the compression main body portion 5 of the compression member 3. In the present embodiment, in a plan view (refer to FIG. 2 and the like), the edge of the adhesion sheet 2 and an adhesion edge of the adhesion region in the adhesion surface 11 of the adhesion sheet 2 coincide with the inner edge 14 of the adhesion sheet 2, but may be configured to not coincide therewith in a plan view.

Since the adhesion sheet 2 of the compression device 1 includes the second portion X2 described above on the compression main body portion 5 side, when the compression member 3 of the compression device 1 compresses the biological surface, the adhesion sheet 2 can be suppressed from peeling off from the biological surface. Hereinafter, this aspect of the compression device and method will be described.

In a state where the adhesion surface 11 adheres to the biological surface, the biological surface is pressed by the compression main body portion 5, so that the compression member 3 can compress the biological surface. In this case, since the adhesion surface 11 of the adhesion sheet 2 adheres to the biological surface, the compression main body portion 5 can maintain a state where the biological surface is compressed. In other words, the force with which the compression main body portion 5 compresses the biological surface is applied via the fixing portion 4 as force that lifts the adhesion surface 11 of the adhesion sheet 2 in the upward direction A2 of the thickness direction A. Namely, since the force is applied in a direction to separate the adhesion sheet 2 from the biological surface, the adhesion region of the adhesion surface tends to partially peel off from the biological surface, which may be a problem. When the adhesion region peels off, the compression force that compresses the biological surface may not be maintained at a desired compression force. Particularly, the force is applied such that the adhesion sheet peels off from the position of the adhesion edge of the adhesion region of the adhesion surface, and thus the adhesion sheet is likely to peel off.

In addition, when the biological surface is compressed by the compression main body portion 5, a large force is applied in the upward direction A2 to the compression member 3 at the position of the compression main body portion 5. For this reason, the compression member 3 is likely to be deformed in a tent shape in which the top portion is at the position of the compression main body portion 5 to project in the upward direction A2. When such a force is applied to the compression member 3, the force that lifts the adhesion sheet 2 in the upward direction A2 is larger at the position of a compression main body portion 5 side of the fixing portion 4 than at a position opposite to the compression main body portion 5 side.

Therefore, if the position of the compression main body portion 5 side of the fixing portion 4 coincided with the position of the adhesion edge of the adhesion region in the adhesion surface of the adhesion sheet in a plan view (refer to FIG. 2 and the like), when the biological surface is compressed by the compression main body portion 5, the adhesion sheet is likely to peel off from the position of the adhesion edge of the adhesion region.

On the other hand, in the adhesion sheet 2 of the compression device 1, the second portion X2 to which the fixing portion 4 of the compression member 3 is not fixed is provided on at least the compression main body portion 5 side with respect to the first portion X1 to which the fixing portion 4 of the compression member 3 is fixed. For this reason, in a plan view (refer to FIG. 2 and the like), the position of the compression main body portion 5 side of the fixing portion 4 does not coincide with the position of the adhesion edge of the adhesion region in the adhesion surface 11 of the adhesion sheet 2 (i.e., the position of the compression main body portion 5 side of the fixing portion 4 is spaced from the position of the adhesion edge of the adhesion region in the adhesion surface 11 of the adhesion sheet 2), and an adhesion edge of the adhesion region is closer to the compression main body portion 5 side than the position of the compression main body portion 5 side of the fixing portion 4. Therefore, when the biological surface is compressed by the compression main body portion 5, peeling force can be suppressed from being applied to the adhesion edge of the adhesion region of the adhesion sheet 2.

Figure 33:
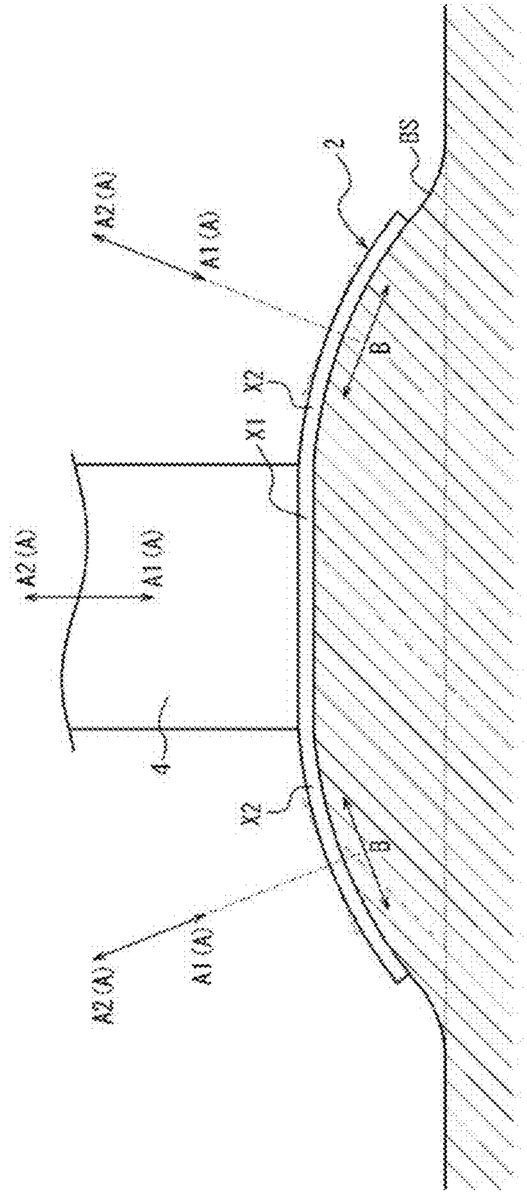
FIG. 33 is a view illustrating an outline of a fixing portion of a compression member illustrated in FIG. 1 and force applied to an adhesion sheet.

Furthermore, as illustrated in FIG. 33, since the fixing portion 4 is lifted in the upward direction A2, the adhesion sheet 2 and a biological surface BS are deformed to protrude at the position of the fixing portion 4. Namely, since the first portion X1 of the adhesion sheet 2 is pulled up in the upward direction A2, force in a direction along the adhesion surface 11 and the biological surface (refer to arrow B in FIG. 33) is likely to be applied to the second portion X2 via the fixing portion 4. In such a manner, the force that is applied to the second portion X2 of the adhesion sheet 2 in the upward direction A2 orthogonal to the biological surface can be reduced. In addition, shearing force in the direction along the biological surface is likely to be applied to the second portion X2 of the adhesion sheet 2. The adhesion sheet 2 is unlikely to be moved by the shearing force in the direction along the biological surface, so that the adhesion sheet 2 is unlikely to peel off. Therefore, the second portion X2 of the adhesion sheet 2 can be unlikely to peel off from the biological surface.

The second portion X2 may be provided on at least the compression main body portion 5 side of the adhesion sheet 2; however, as in the present embodiment, it is preferable that the second portion X2 is provided on both the compression main body portion 5 side of the adhesion sheet 2 and the opposite side of the adhesion sheet 2 from the compression main body portion 5 side.

In such a manner, the same above-described effect of the compression main body portion 5 side can be obtained also on the opposite side from the compression main body portion 5 side, and the adhesion sheet 2 can be further suppressed from peeling off from the biological surface.

Hereinafter, the compression member 3 of the present embodiment will be described in further detail.

The compression member 3 of the present embodiment includes the expander 21 that is expandable toward the downward direction A1 of the thickness direction A, and a holder 22 that holds the expander 21. In a plan view (refer to FIGS. 2 and 3), the holder 22 of the present embodiment is disposed across the in-edge region SP1 which is located to overlap the adhesion sheet 2 and the central opening region as the out-of-edge region SP2 which is located to not overlap the adhesion sheet 2. In other words, the holder 22 of the present embodiment includes a portion which overlaps the adhesion sheet 2 and a portion which does not overlap the adhesion sheet 2 in a plan view (refer to FIGS. 2 and 3). In addition, in the present embodiment, the portion of the compression member 3, which does not overlap the adhesion sheet 2 in a plan view (refer to FIGS. 2 and 3), more specifically, the portion of the holder 22, which does not overlap the adhesion sheet 2 in a plan view (refer to FIGS. 2 and 3), is located in the central opening region defined by the annular-shaped adhesion sheet 2.

The fixing portion 4 of the present embodiment described above is formed of the contact surface 22*a* of the holder 22, the contact surface 22*a* being in contact with the adhesion sheet 2 in the in-edge region SP1. More specifically, the fixing portion 4 of the present embodiment described above is formed of the contact surface 22*a* of the portion of the holder 22, the portion not overlapping the adhesion sheet 2 and the contact surface 22*a* being in contact with the adhesion sheet 2. The compression main body portion 5 of the present embodiment described above includes the expander 21 and the holder 22.

The expander 21 of the present embodiment is an inflator 23 that is inflatable toward the downward direction A1 of the thickness direction A by supply of a fluid to the inflator 23. When the inflator 23 as the expander 21 of the present embodiment is changed in form from the retracted form (refer to FIG. 4A) to the protruding form (refer to FIG. 4B) described above, the inflator 23 protrudes further toward the downward direction A1 in the thickness direction A than the adhesion surface 11 of the adhesion sheet 2, to take a posture capable of compressing the biological surface or applying a compressive force to the biological surface.

FIG. 3 illustrates the inflator 23 in the retracted form. As illustrated in FIG. 3, when in the retracted form, the inflator 23 of the present embodiment is disposed in a recessed portion of the holder 22. When in the retracted form, the inflator 23 of the present embodiment extends in a tubular shape to define an internal space. The internal space of the inflator 23 communicates with a tube 28 that penetrates or passes through the holder 22 to extend to outside the holder 22. A fluid such as air is supplied through the tube 28 to the internal space of the inflator 23 from a fluid supply device to be connected to an inflation port as a connection portion 29 provided in an end portion of the tube 28. Therefore, the inflator 23 can be changed in form from the retracted form (refer to FIG. 4A) to the protruding form (refer to FIG. 4B). The fluid supplied to the internal space of the inflator 23 is not limited to gas, and may be liquid.

The inflator 23 may be a balloon that is inflated by gas such as air. Examples of the material from which the inflator 23 may be fabricated include a flexible material such as soft polyvinyl chloride, polyurethane, polyethylene, polypropylene, polyester, ethylene-vinyl acetate copolymer (EVA), silicone, or a mixture of any of these materials.

The holder 22 of the present embodiment includes a housing portion 24 that is located in a portion which does not overlapping the adhesion sheet 2 in a plan view (refer to FIG. 2 and the like), to accommodate the expander 21; the support portion 25 that is located in a portion which overlaps the adhesion sheet 2 in a plan view (refer to FIG. 2 and the like), to include the contact surface 22*a*; and an arm portion 26 that connects the housing portion 24 and the support portion 25.

The housing portion 24 defines the recessed portion that accommodates the inflator 23 as the expander 21 described above. The recessed portion of the housing portion 24 is open toward the downward direction A1, and is defined by a bottom portion that is located on an upward direction A2 side and a side wall portion that continues to the bottom portion to surround the inflator 23. Therefore, the inflation of an upward direction A2 side of the inflator 23 is restricted by the bottom portion. In addition, the inflation of the inflator 23 is restricted by a side wall that is located around a direction orthogonal to the thickness direction A. Namely, since the inflator 23 is restricted by the bottom portion and the side wall portion of the recessed portion, the inflator 23 is inflated to protrude toward a downward direction A1 side. The compression main body portion 5 of the present embodiment includes the inflator 23 as the expander 21, and the housing portion 24 of the holder 22.

An outer wall of the housing portion 24 of the present embodiment is provided with a first guide portion 24*a* that guides the mounting position of the compression device 1 on the biological surface with respect to the medical device such as a catheter or a sheath which is inserted into the living body. The first guide portion 24*a* of the present embodiment is a projection that is formed on a side surface (outer side surface) of the housing portion 24, the side surface being adjacent to the central opening region. More specifically, the first guide portion 24*a* of the present embodiment is a projection that is formed on a surface on a slit 15 side of the housing portion 24. In the present embodiment, since the first guide portion 24*a* is provided, the compression device 1 and the medical device can be easily aligned in a direction orthogonal to the extending direction of the slit 15. The shape of the first guide portion 24*a* is not limited to a projection, and may be another shape such as a recessed portion. In addition, the first guide portion 24*a* is not limited to a three-dimensional shape such as a projection, and may be a mark formed by printing or the like.

The support portion 25 of the present embodiment extends in an annular shape. As described above, the adhesion sheet 2 of the present embodiment extends in an annular shape, and the support portion 25 of the present embodiment extends in an annular shape in the in-edge region SP1 along the adhesion sheet 2. The support portion 25 of the present embodiment is thin in the thickness direction A, and is deformable to follow the adhesion sheet 2. The contact surface 22*a* as the fixing portion 4 of the present embodiment is formed of an annular surface on the downward direction A1 side of the support portion 25.

In addition, a gap 25*a* is formed in the support portion 25 at the same position as the slit 15 of the adhesion sheet 2 in a circumferential direction. Therefore, the medical device such as a catheter or a sheath is movable from outside the adhesion sheet 2 into the central opening region through the slit 15 and the gap 25*a*.

Furthermore, the support portion 25 of the present embodiment includes a connection portion 25*b* that connects both sides interposing the gap 25*a* (i.e., the connection portion 25*b* connects the portions of the support portion 25 located on opposite sides of the gap 25*a*). The connection portion 25*b* of the support portion 25 extends from one side toward the other side of both sides interposing the gap 25*a*, and includes a receiving portion 25*b*1 having a projection receiving hole and a projection portion 25*b*2 that is located on the other side with respect to the gap 25*a* to be inserted into the projection receiving hole. Since the connection portion 25*b* is provided, the shapes of the support portion 25 and the adhesion sheet 2 are easily held to be annular, and the operability in operation other than an operation of moving the medical device through the slit 15 and the gap 25*a* can be improved.

Furthermore, the support portion 25 of the present embodiment is provided with a second guide portion 25*c* that guides the mounting position of the compression device 1 on the biological surface with respect to the medical device such as a catheter or a sheath which is inserted into the living body. The second guide portion 25*c* of the present embodiment is a projection that is formed on a surface on the upward direction A2 side of the support portion 25 having an annular shape. As shown in FIG. 1, the second guide portion 25*c* may include two projections 25*c*, 25*c* along one part of the support portion 25 and two other projections 25*c*, 25*c* along another part of the support portion 25. In the present embodiment, since the second guide portion 25*c* is provided, the compression device 1 and the medical device can be easily aligned in the extending direction of the slit 15. The shape of the second guide portion 25*c* is not limited to a projection, and may be another shape such as a recessed portion. In addition, the second guide portion 25*c* is not limited to a three-dimensional shape such as a projection, and may be a mark formed by printing or the like.

The arm portion 26 of the present embodiment includes an arm main body 26*a* that protrudes from the outer wall of the housing portion 24, and an arm connection portion 26*b* that protrudes from the arm main body 26*a* along the support portion 25 to continue to the support portion 25 on the downward direction A1 side.

The arm main body 26*a* protrudes linearly from the outer wall of the housing portion 24 in the direction orthogonal to the thickness direction A. A plurality (two in the present embodiment) of the arm main bodies 26*a* of the present embodiment are provided, and protrude from the outer wall of the housing portion 24 toward opposite directions.

The arm connection portion 26*b* protrudes along the support portion 25 from an end portion on an opposite side of the arm main body 26*a* from the housing portion 24. In a plan view (refer to FIG. 2 and the like), the arm connection portion 26*b* of the present embodiment protrudes toward a direction substantially orthogonal to an extending direction of the arm main body 26*a*. Since the arm connection portion 26*b* is provided in such a manner, the force with which the support portion 25 lifts the adhesion sheet 2 in the upward direction A2 can be dispersed in the circumferential direction of the support portion 25. Therefore, the force that lifts the adhesion sheet 2 in the upward direction A2 can be suppressed from being locally concentrated on a part in the circumferential direction of the support portion 25, and the adhesion sheet 2 can be suppressed from locally peeling off from the biological surface.

The arm connection portion 26*b* of the present embodiment protrudes from the end portion of one arm main body 26*a* to both sides along the support portion 25. In such a manner, since the arm portion 26 has a T shape in a top view (refer to FIG. 2), the force with which the support portion 25 lifts the adhesion sheet 2 in the upward direction A2 can be further dispersed in the circumferential direction of the support portion 25.

Furthermore, the arm connection portion 26*b* of the present embodiment is gradually reduced in thickness in the thickness direction A as the distance from the arm main body 26*a* is increased (i.e., the thickness of the arm connection portion 26*b* becomes gradually smaller at increasing distances away from the arm main body 26*a*). In such a manner, in the circumferential direction of the support portion 25, a large step in rigidity can be suppressed from being formed between a portion where the arm connection portion 26*b* is provided and a portion where the arm connection portion 26*b* is not provided, and the support portion 25 and the adhesion sheet 2 can be suppressed from being damaged at the boundary between the portion where the arm connection portion 26*b* is provided and the portion where the arm connection portion 26*b* is not provided. Furthermore, in a state where the compression device 1 is mounted on the biological surface, the compression device 1 can be suppressed from being caught on clothes, a bed sheet, or the like.

The rigidity in the thickness direction A of each of the housing portion 24, the support portion 25, and the arm portion 26 of the present embodiment is greater than the rigidity in the thickness direction A of the adhesion sheet 2. In addition, the rigidity in the thickness direction A of the arm portion 26 may be higher or lower than the rigidity in the thickness direction A of each of the housing portion 24 and the support portion 25. In the present embodiment, the rigidity is decreased in order of the housing portion 24, the arm portion 26, and the support portion 25. That is, the support portion 25 is less rigid than the arm portion 26, and the arm portion 26 is less rigid than the housing portion 24. The arm portion 26 may be configured to be bendable in the thickness direction A when a predetermined external force is applied thereto.

Examples of the material from which the holder 22 of the present embodiment may be fabricated include a resin material. Examples of the resin material include thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, and polyethylene terephthalate, and thermosetting resins such as phenol resin, epoxy resin, silicone resin, and unsaturated polyester.

It is preferable that at least the housing portion 24 of the holder 22 is made of an ultrasound transmitting material. In addition, it is preferable that the expander 21 described above is also made of an ultrasound transmitting material. When the inflator 23 is used as the expander 21, not only the inflator 23 is made of an ultrasound transmitting material, but also an ultrasound transmitting fluid such as water or gel is used as the fluid to be supplied to the inflator 23. In such a manner, an obstructed state of a vein caused by the compression device 1 can be detected by an ultrasound device. The details will be described later.

<Compression Method Performed Using Compression Device 1>

Figure 5:
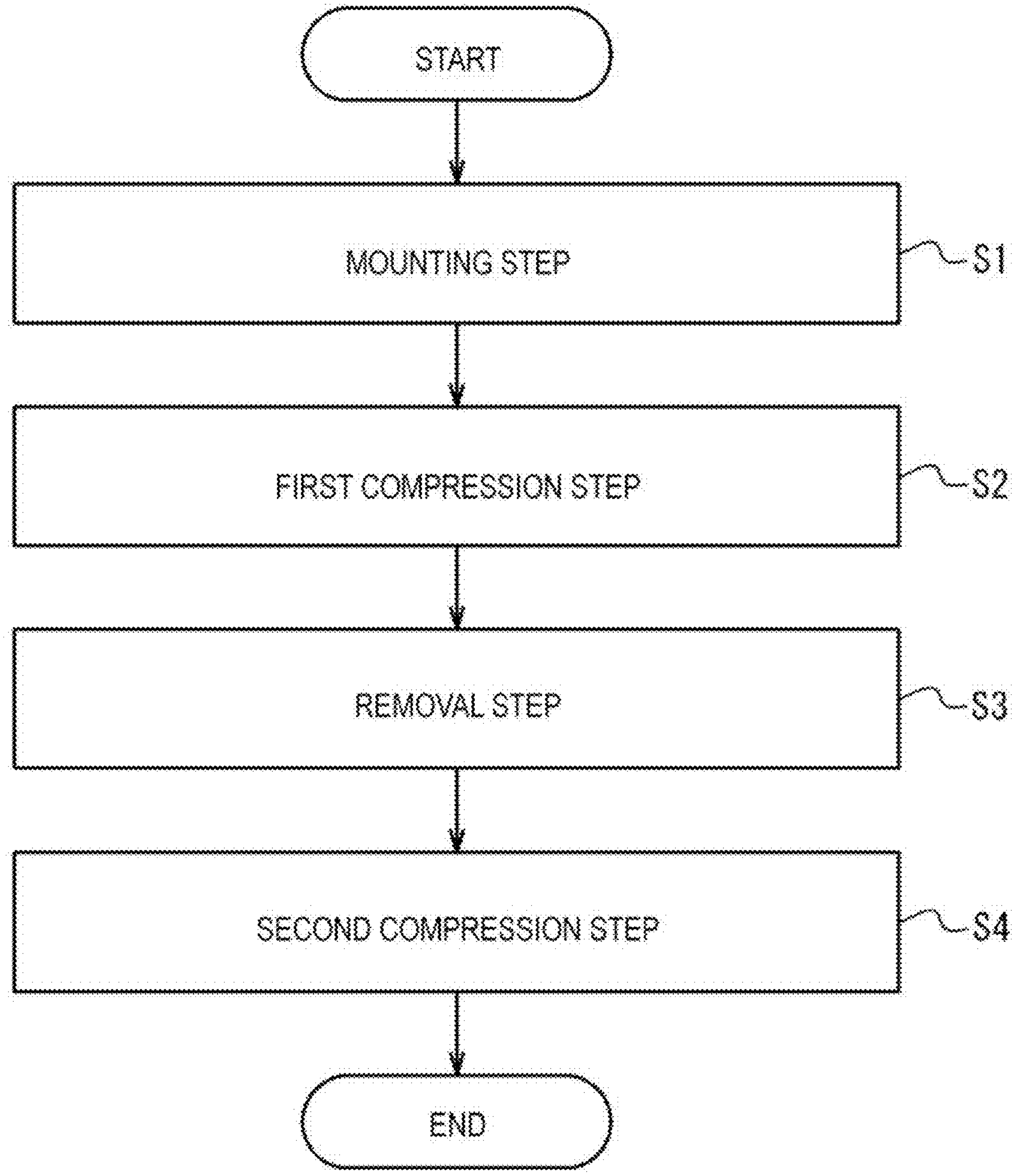
FIG. 5 is a flowchart illustrating a compression method as one embodiment.

Next, a method for compressing a biological surface or applying a compression force to the biological surface which is performed using the compression device 1 will be described. FIG. 5 is a flowchart illustrating one example of the method for compressing a biological surface. The compression method illustrated in FIG. 5 includes a mounting step S1, a first compression step S2, a removal step S3, and a second compression step S4. FIGS. 6A to 6D are views illustrating an outline of the mounting step S1. FIG. 6E is a view illustrating an outline of the first compression step S2. FIG. 6F is a view illustrating an outline of the removal step S3. FIG. 6G is a view illustrating an outline of the second compression step S4.

Figure 34A:
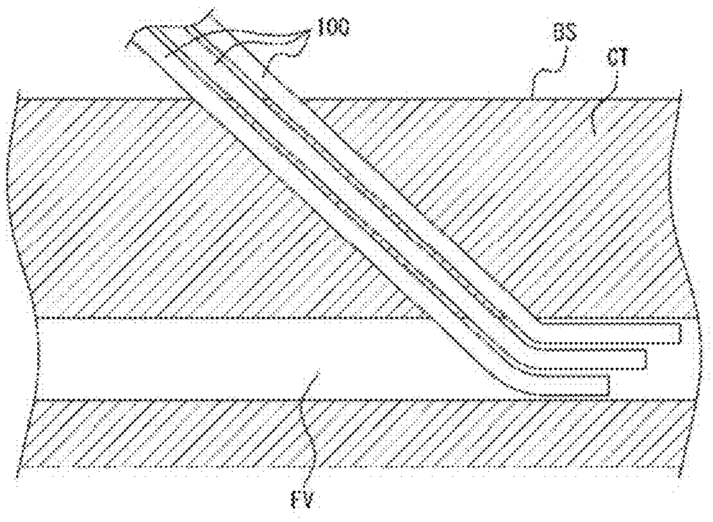
FIG. 34A is a view illustrating a state where medical devices are inserted into a femoral vein from a biological surface through a connective tissue.
Figure 34B:
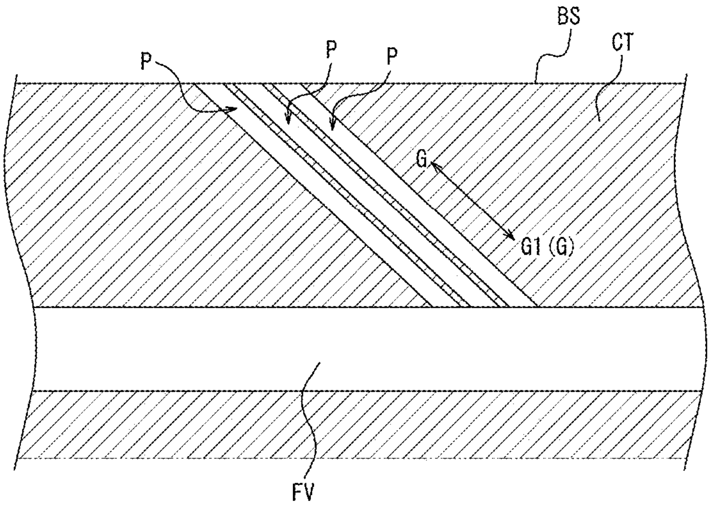
FIG. 34B is a view illustrating a state after the medical devices are removed from the state illustrated in FIG. 34A.

The compression method illustrated in FIGS. 5 and 6A to 6G is a compression method by which the biological surface BS is compressed to narrow or obstruct a perforation, which is formed when a sheath as a medical device 100 that is inserted into a vein such as a femoral vein from the biological surface BS through a connective tissue is removed, without obstructing the vein. Therefore, after the sheath as the medical device 100 is removed, hemostasis can be performed. First, the perforation formed after the medical device 100 is removed will be described with reference to FIGS. 34A and 34B. FIG. 34A illustrates a state where the sheaths as the medical devices 100 are inserted into a femoral vein FV from the biological surface BS through a connective tissue CT. FIG. 34A illustrates three sheaths as the medical devices 100; however, two or less sheaths may be used or four or more sheaths may be used. FIG. 34B illustrates a state after the sheaths as the medical devices 100 are removed from the state illustrated in FIG. 34A. As illustrated in FIG. 34B, when the sheaths as the medical devices 100 are removed, a perforation P is formed between the biological surface BS and the femoral vein FV. In the compression method illustrated in FIGS. 5 and 6A to 6G, the perforation P can be narrowed or obstructed without obstructing the femoral vein FV. For this reason, even when hemostasis is performed for bleeding from the vein at a deep position from the biological surface, hemostasis can be more efficiently performed without the need to narrow or obstruct the vein itself. Hereinafter, steps S1 to S4 will be described in detail with reference to FIGS. 6A to 6G.

Figure 6A:
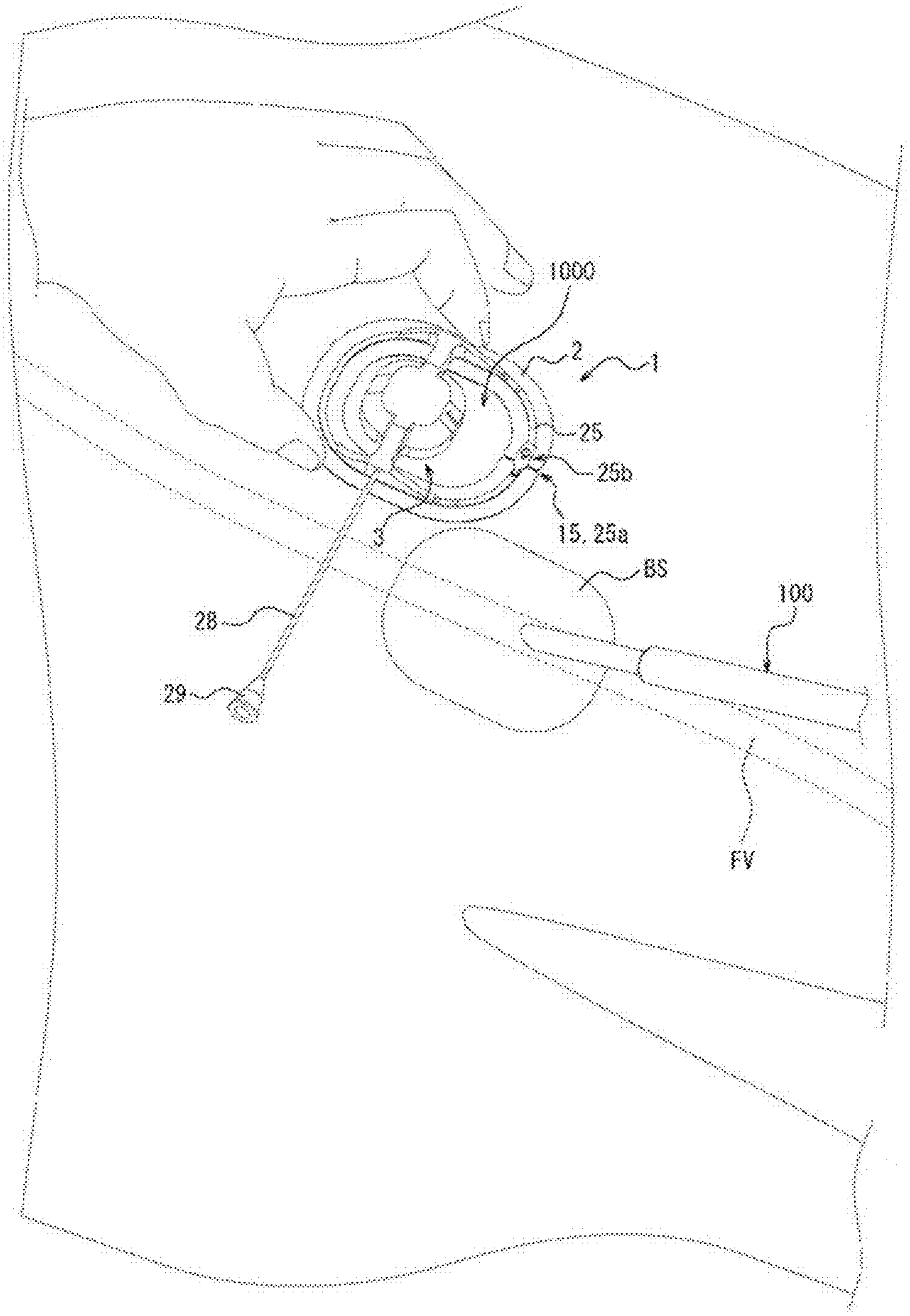
FIG. 6A is a view illustrating an outline of a mounting step of FIG. 5.

FIG. 6A illustrates a state where the sheath as the medical device 100 is inserted into the femoral vein FV (refer to FIGS. 34A and 34B) from the biological surface BS. First, in this state, the compression device 1 is mounted on the biological surface BS. The connection of the connection portion 25*b* of the support portion 25 is released from the state illustrated in FIG. 6A, and the slit 15 of the adhesion sheet 2 and the gap 25*a* of the support portion 25 are opened. Specifically, the projection portion 25*b*2 (refer to FIG. 1) of the connection portion 25*b* of the support portion 25 is removed from the projection receiving hole of the receiving portion 25*b*1 (refer to FIG. 1), so that the connection of the connection portion 25*b* is released.

Figure 6B:
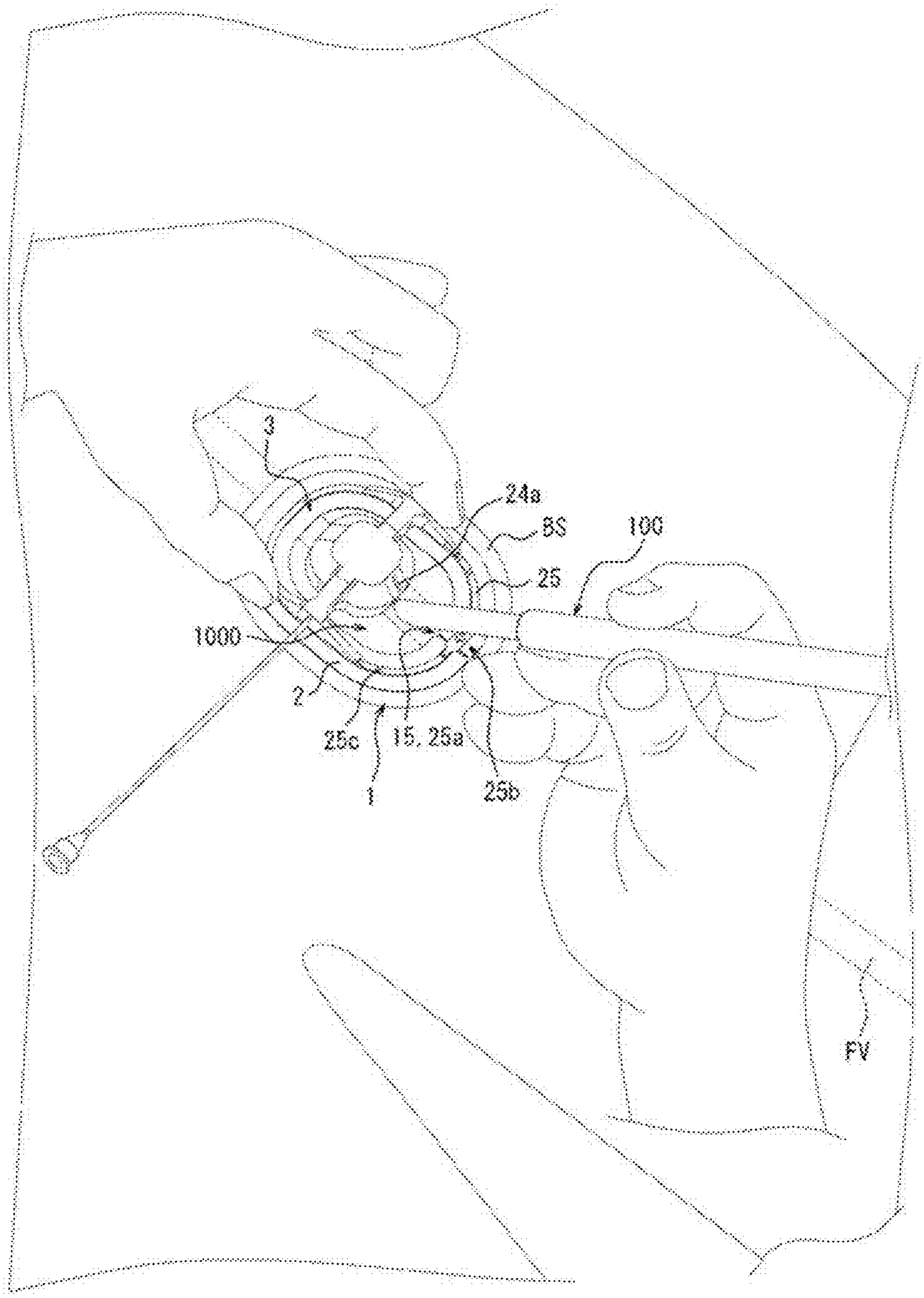
FIG. 6B is a view illustrating an outline of the mounting step of FIG. 5.

Therefore, even in a state where the sheath as the medical device 100 is inserted into the living body, as illustrated in FIG. 6B, a portion of the medical device 100, the portion extending outside the living body, is movable from outside the adhesion sheet 2 into the central opening region through the slit 15 and the gap 25*a* as shown in FIG. 6B. FIG. 6B illustrates a state where after the sheath as the medical device 100 is moved into the central opening region, the connection portion 25*b* is connected again and the slit 15 is closed. As illustrated in FIG. 6B, after the medical device 100 is moved into the central opening region, the mounting position of the compression device 1 on the biological surface BS is adjusted. The mounting position is adjusted by using the first guide portion 24*a* and the second guide portion 25*c* described above, so that the compression device 1 is mountable at a proper position.

Figure 6C:
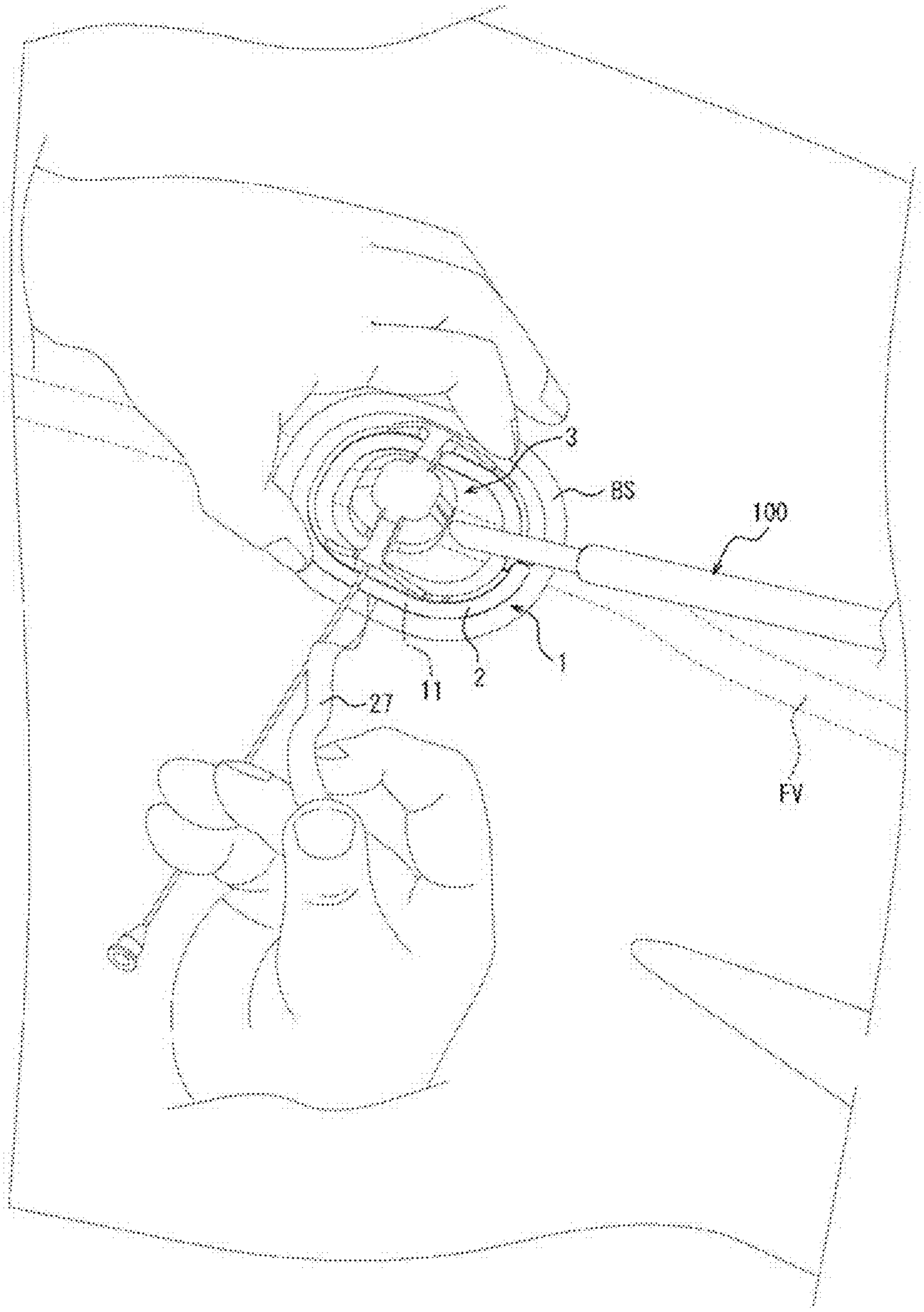
FIG. 6C is a view illustrating an outline of the mounting step of FIG. 5.
Figure 6D:
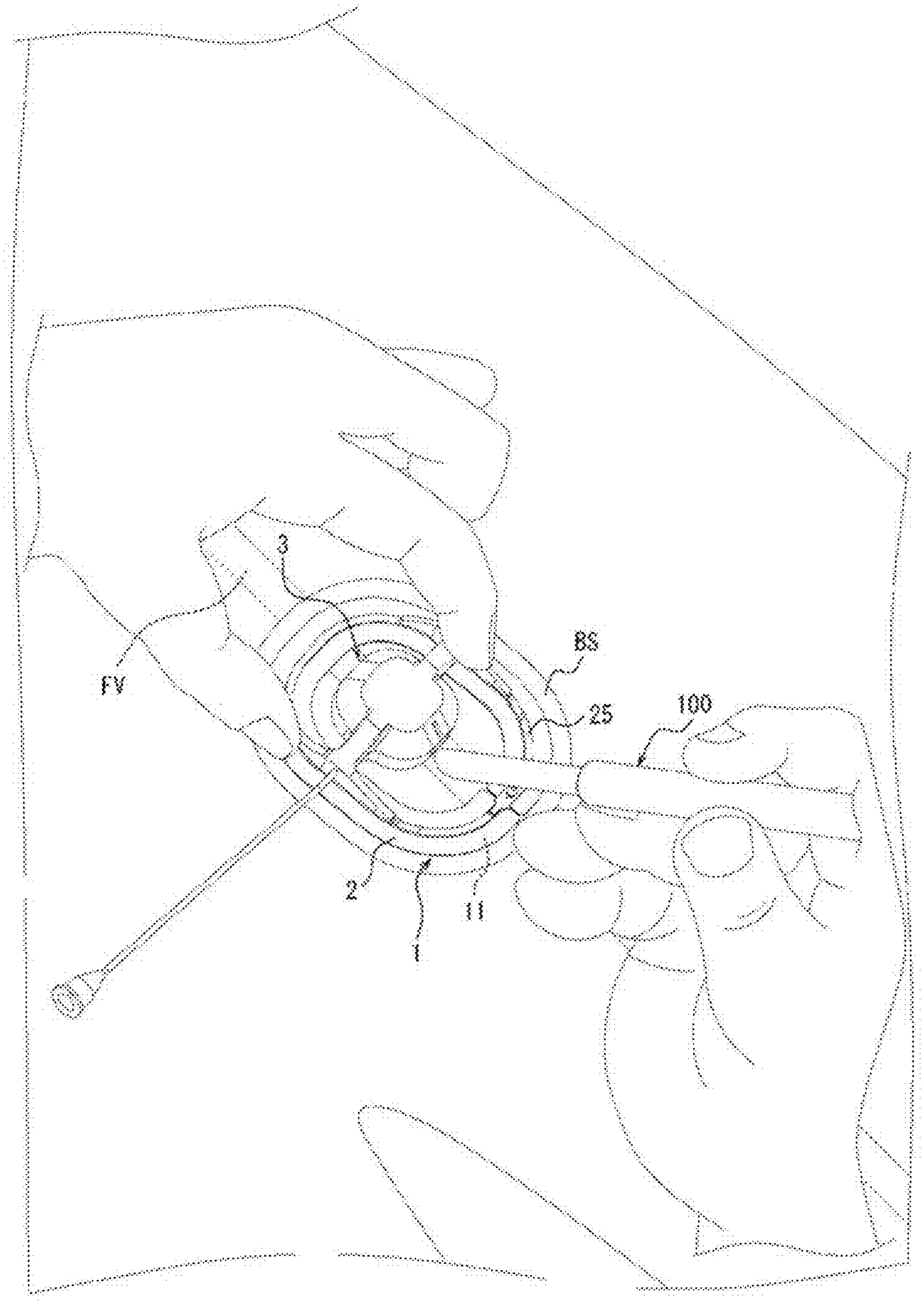
FIG. 6D is a view illustrating an outline of the mounting step of FIG. 5.
Figure 6E:
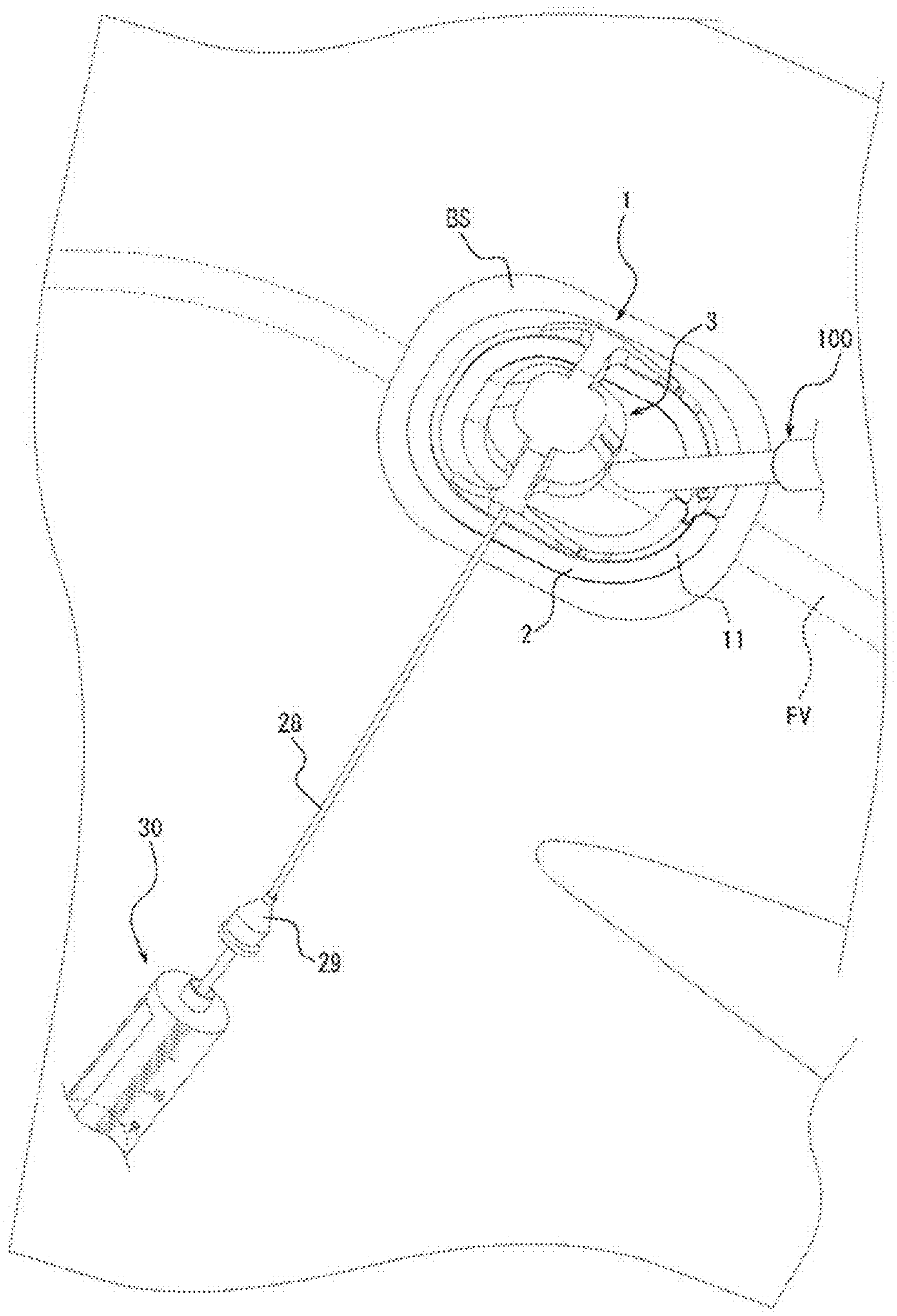
FIG. 6E is a view illustrating an outline of a first compression step of FIG. 5.
Figure 6F:
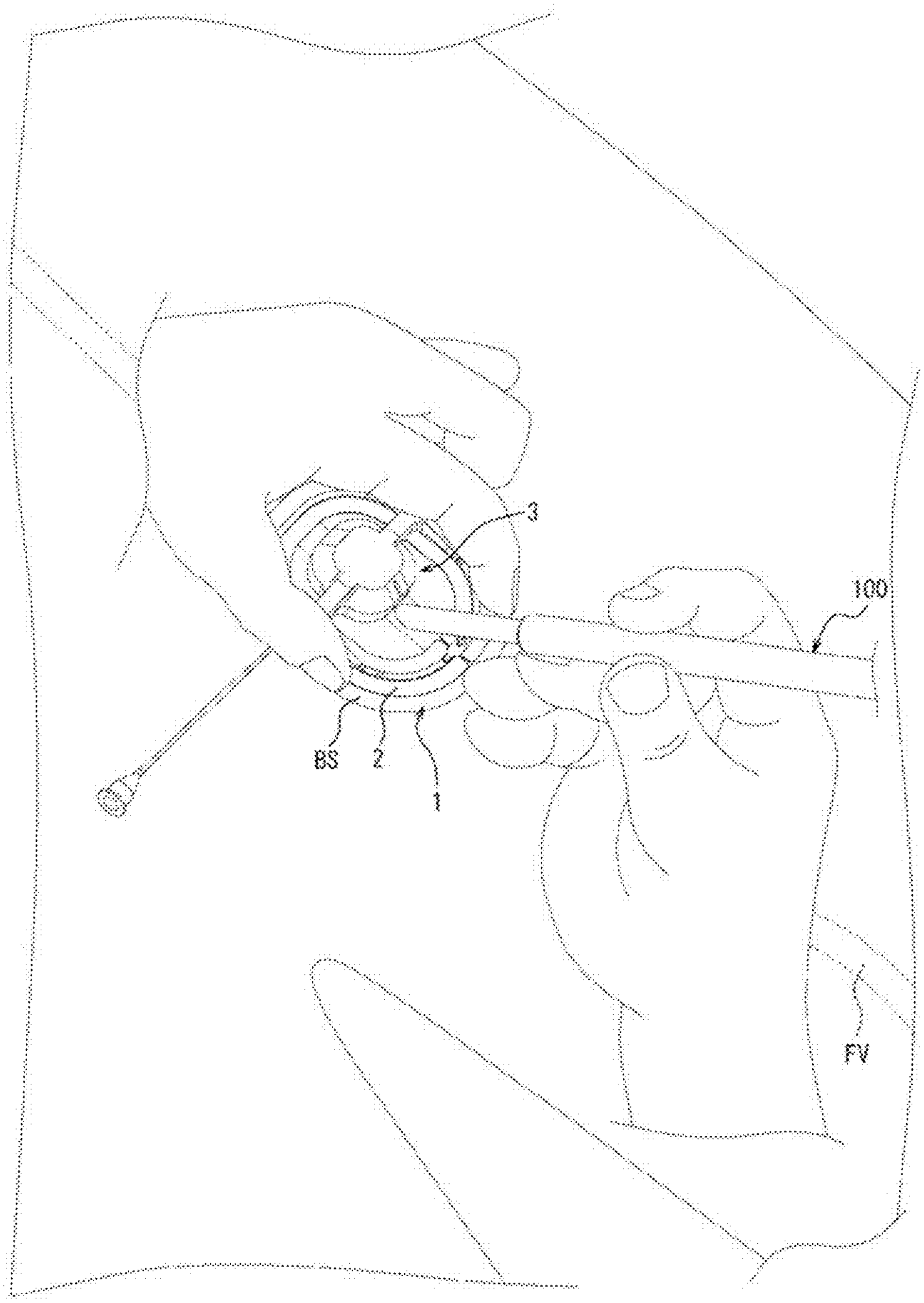
FIG. 6F is a view illustrating an outline of a removal step of FIG. 5.
Figure 6G:
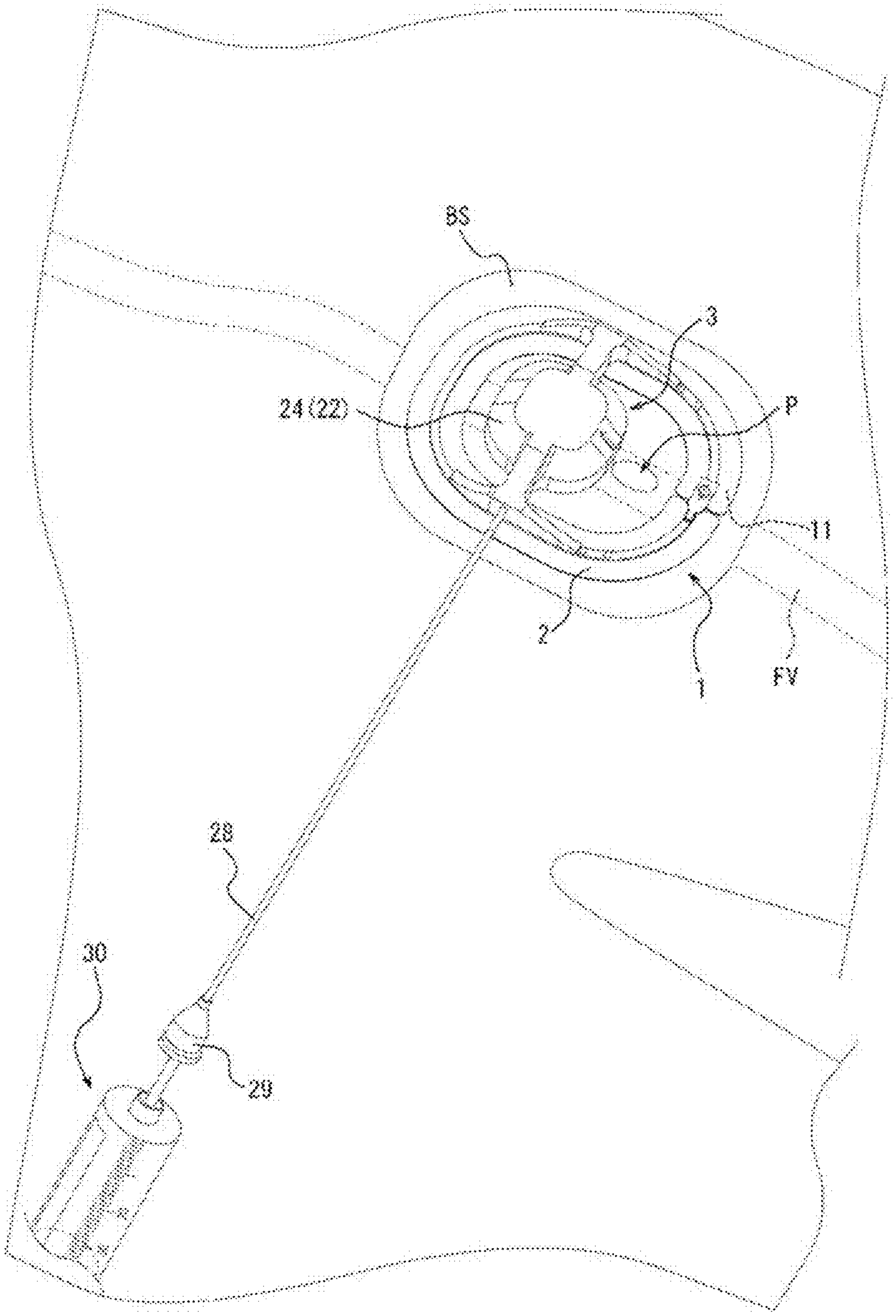
FIG. 6G is a view illustrating an outline of a second compression step of FIG. 5.

As illustrated in FIG. 6C, after the mounting position of the compression device 1 on the biological surface BS is determined, the separation sheet 27 laminated on the adhesion surface 11 of the adhesion sheet 2 is peeled off, so that the adhesion surface 11 is exposed. Thereafter, as illustrated in FIG. 6D, the adhesion surface 11 of the adhesion sheet 2 adheres to the position adjusted in FIG. 6B, so that the compression device 1 is mountable on the biological surface BS.

Next, as illustrated in FIG. 6E, a syringe 30 representing an example of a fluid supply device is connected to the connection portion 29 of the tube 28. Air is supplied to the inflator 23 (refer to FIGS. 3 and 4B) of the compression device 1 through the tube 28 to inflate the inflator 23. In such a manner, before the sheath as the medical device 100 is removed from the biological surface BS, the vicinity of a wound hole of the biological surface BS can be compressed (a compression force can be applied) in advance. In other words, in a state where the sheath as the medical device 100 is inserted into or positioned in the femoral vein FV as a vein from the biological surface BS through the connective tissue CT (refer to FIGS. 34A and 34B), the compression of the biological surface BS is started. In such a manner, since compression is performed before the medical device 100 is removed from the biological surface BS, immediately after the sheath as the medical device 100 is removed, the biological surface BS can be compressed such that the perforation P (refer to FIG. 34B) that extends from the biological surface BS to the femoral vein FV (refer to FIGS. 34A and 34B) is narrowed or obstructed.

Next, as illustrated in FIG. 6F, the sheath as the medical device 100 is removed from the biological surface BS. More specifically, the sheath as the medical device 100 of the present embodiment is removed to outside the living body through the central opening region of the adhesion sheet 2. The perforation P illustrated in FIG. 34B is formed by the removal of the sheath. If the biological surface BS is not compressed at all in this state, there occurs bleeding outside the living body from the femoral vein FV through the perforation P and the wound hole on the biological surface BS. However, in the compression method illustrated here, as illustrated in FIG. 6E, before the sheath as the medical device 100 is removed from the biological surface BS, the biological surface BS is compressed in advance. For this reason, immediately after the sheath is removed, the biological surface BS is compressed such that the perforation P (refer to FIG. 34B) is narrowed or obstructed, and the amount of bleeding immediately after the removal of the sheath can be suppressed.

Next, as illustrated in FIG. 6G, the syringe 30 as a fluid supply device is connected again to the connection portion 29 of the tube 28. Air is supplied again to the inflator 23 (refer to FIGS. 3 and 4B) of the compression device 1 through the tube 28 to apply pressure, or air is removed to reduce pressure. In other words, after the sheath as the medical device 100 is removed, the compression force on the biological surface BS is adjusted. Therefore, the compression force on the biological surface BS is adjusted to further narrow or obstruct the perforation P (refer to FIG. 34B) without obstructing the femoral vein FV (refer to FIGS. 34A and 34B), and thus the amount of bleeding can be greatly reduced, or bleeding can be stopped.

More specifically, when bleeding is confirmed after the sheath is removed, the compression force is gradually increased to apply pressure until hemostasis is achieved. On the other hand, when hemostasis is confirmed after the sheath is removed, the compression force is gradually decreased to reduce pressure until bleeding is confirmed. Then, after bleeding is confirmed, the compression force is gradually increased to apply pressure until hemostasis is achieved. In such a manner, the obstruction of the femoral vein FV (refer to FIGS. 34A and 34B) by over-pressurization can be prevented.

In addition, whether or not the biological surface BS is properly compressed may be detected by using the ultrasound device. Specifically, since the holder 22 and the inflator 23 (refer to FIGS. 3 and 4B) are made of an ultrasound transmitting material and an ultrasound transmitting fluid such as water is supplied to the inflator 23, a compressed state obtained by the compression device 1 can be diagnosed by ultrasound waves. Namely, the ultrasound device can detect whether or not the femoral vein FV (refer to FIGS. 34A and 34B) is obstructed. The compression force of the compression device 1 may be adjusted according to a result of diagnosis by the ultrasound device.

The compressed state is maintained for several hours (for example, 2 to 6 hours) as it is, so that hemostasis can be completed. After hemostasis is completed, the adhesion surface 11 of the adhesion sheet 2 is peeled off from the biological surface BS to remove the compression device 1 from the biological surface BS.

In the compression method illustrated here, the perforation P (refer to FIG. 34B) is narrowed or obstructed without obstructing the femoral vein FV (refer to FIGS. 34A and 34B). In the case of hemostasis at a vein, hemostasis can be performed by narrowing or obstructing the perforation P (refer to FIG. 34B). On the other hand, for example, in the case of hemostasis at a femoral artery, even if only the perforation is obstructed, the blood leaks to spread in the connective tissue CT (refer to FIGS. 34A and 34B), so that hemostasis cannot be achieved. In the case of hemostasis at the femoral artery, large-scale measures such as a method for applying strong compression to the extent that the artery itself is narrowed or obstructed and a method for closing a hole in an artery wall are required.

Therefore, in the above-described compression method, it is preferable that the biological surface BS is compressed to a position where the compression depth from the biological surface BS is 5 mm to 20 mm. When the compression depth is in the above range, a compressed state where the perforation P (refer to FIG. 34B) is narrowed or obstructed without obstructing the vein is easily realized. The compression depth is more preferably 5 mm to 15 mm and further preferably 8 mm to 12 mm.

Furthermore, in the above-described compression method, it is preferable that the biological surface BS is compressed at 100 $g/cm^2$ to 400 $g/cm^2$ from the biological surface BS. That is, the pressure applied to the biological surface BS is preferably between 100 $g/cm^2$ and 400 $g/cm^2$. The compression pressure is a pressure after the sheath as the medical device 100 is removed, and does not mean the above-described compression force before the sheath is removed. When the compression pressure is in the above range, a compressed state where the perforation P (refer to FIG. 34B) is narrowed or obstructed without obstructing the vein is easily realized. The compression pressure is more preferably 200 $g/cm^2$ to 400 $g/cm^2$ and further preferably 200 $g/cm^2$ to 300 $g/cm^2$.

In addition, it is preferable that the biological surface BS is compressed along a direction orthogonal to an extending direction of the perforation P (refer to FIG. 34B). The expression "compression is performed along the direction orthogonal to the extending direction of the perforation" is not limited to a case where compression is performed only in the direction orthogonal to the extending direction of the perforation, and also includes a case where compression is performed in a direction that is inclined at a predetermined angle or less (for example, 30 degrees or less) with respect to the direction orthogonal to the extending direction of the perforation. A compression device that can compress the biological surface BS along the direction orthogonal to the extending direction of the perforation P (refer to FIG. 34B) will be described in detail later (refer to FIGS. 10 to 13B).

According to the compression method illustrated in FIGS. 5 and 6A to 6G, hemostasis can be performed by narrowing or obstructing the perforation P (refer to FIG. 34B) without obstructing the vein such as the femoral vein FV. Particularly, since the above-described compression method is realized by the compression device 1, compression by the hand of a health care worker or the use of a large-scale hemostatic device is not required, and hemostasis can be performed by a simple method. Furthermore, as illustrated in FIG. 34B, even when a plurality of the perforations P are collectively formed, the plurality of perforations P can be collectively narrowed or obstructed.

Second Embodiment

Next, a compression device 101 as a second embodiment will be described with reference to FIGS. 7 to 9. In the compression device 101 of the present embodiment, the configuration of a compression member differs but the other configuration is the same in comparison to the compression device 1 described above. The following description will mainly focus on the above-mentioned point of difference, and features that are the same or similar to those described above are identified by the same reference numerals and a detailed description of such features is not repeated.

Figure 7:
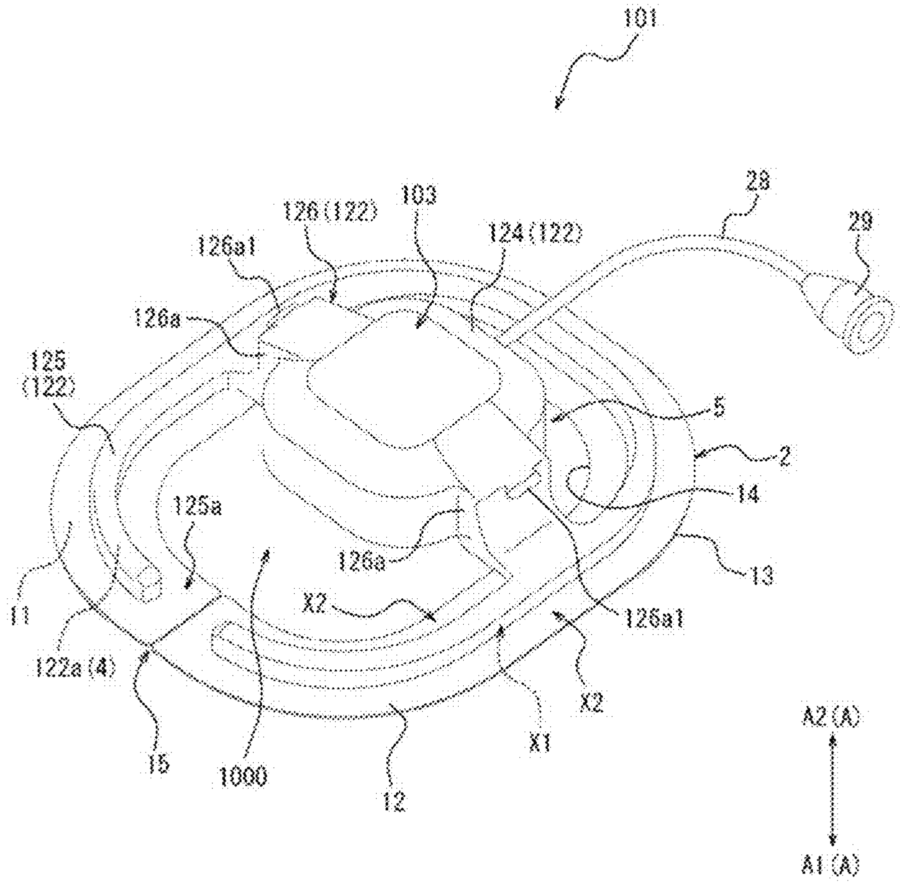
FIG. 7 is a perspective view of a compression device as one embodiment.

FIG. 7 is a perspective view of the compression device 101. FIGS. 8 and 9 are plan views of the compression device 101. Specifically, FIG. 8 is a top view of the compression device 101. FIG. 9 is a bottom view of the compression device 101.

The compression device 101 includes the adhesion sheet 2 and a compression member 103. The adhesion sheet 2 includes the adhesion surface 11 that adheres to a biological surface, and the mounting surface 12 that is located on an opposite side of the adhesion sheet 2 from the adhesion surface 11. In a plan view seen along the thickness direction A, the compression member 103 is disposed across the in-edge region SP1 which overlaps the adhesion sheet 2 and the out-of-edge region SP2 which does not overlap the adhesion sheet 2.

The compression member 103 includes the fixing portion 4 and the compression main body portion 5.

The adhesion sheet 2 includes the first portion X1 to which the fixing portion 4 is fixed and the second portion X2 to which the fixing portion 4 is not fixed. In the compression device 101, the second portion X2 is provided on at least the compression main body portion 5 side of the adhesion sheet 2. An adhesion portion made of an adhesive or the like is provided in the adhesion surface 11 of the adhesion sheet 2 at the position of each of the first portion X1 and the second portion X2.

In other words, in the adhesion sheet 2 of the compression device 101, the second portion X2 is provided on at least the compression main body portion 5 side with respect to the first portion X1 of the adhesion sheet 2. More specifically, in the adhesion sheet 2 of the present embodiment, the second portion X2 that continuously extends from the first portion X1 is provided on at least the compression main body portion 5 side with respect to the first portion X1 of the adhesion sheet 2.

The compression member 103 of the present embodiment includes an expander 121 that is expandable toward the downward direction A1 of the thickness direction A, and a holder 122 that holds the expander 121.

The fixing portion 4 of the present embodiment described above is formed of a contact surface **122*a* of the holder 122, the contact surface 122*a* being in contact with the adhesion sheet 2 in the in-edge region SP1. The compression main body portion 5 of the present embodiment described above includes the expander 121 and the holder 122**.

The expander 121 of the present embodiment is an inflator 123 that is inflatable toward the downward direction A1 of the thickness direction A by supply of a fluid. Similar to the inflator 23 (refer to FIGS. 4A and 4B and the like), the inflator 123 as the expander 121 of the present embodiment is also changed in form from a retracted form to a protruding or projecting form, and thus the inflator 123 protrudes or projects further toward the downward direction A1 in the thickness direction A than the adhesion surface 11 of the adhesion sheet 2, to take a posture capable of compressing the biological surface.

Figure 9:
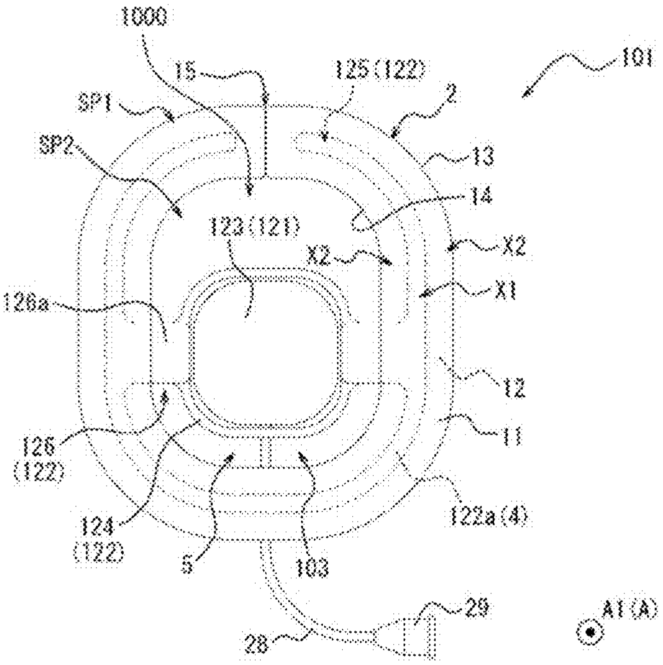
FIG. 9 is a bottom view of the compression device illustrated in FIG. 7.

FIG. 9 illustrates the inflator 123 in the retracted form. As illustrated in FIG. 9, when in the retracted form, the inflator 123 of the present embodiment is disposed in a recessed portion of the holder 22. When in the retracted form, the inflator 123 of the present embodiment defines a substantially rectangular internal space. The internal space of the inflator 123 communicates with the tube 28 that penetrates through the holder 122 to extend to outside the holder 122. A fluid such as air is supplied through the tube 28 to the internal space of the inflator 123 from a fluid supply device to be connected to the connection portion 29 provided in the end portion of the tube 28. Therefore, the inflator 123 can be changed in form from the retracted form to the protruding form. The fluid supplied to the internal space of the inflator 123 is not limited to gas, and may be liquid.

The inflator 123 may be a balloon that is inflated by gas such as air. As the forming material of the inflator 123, the same material as the above-described forming material of the inflator 23 (refer to FIGS. 4A and 4B and the like) can be used.

The holder 122 of the present embodiment includes a housing portion 124 that is located in the out-of-edge region SP2 to accommodate the inflator 123 as the expander 121; a support portion 125 that is located in the in-edge region SP1 to include the contact surface **122*a*; and an arm portion 126 that connects the housing portion 124 and the support portion 125**.

In comparison to the housing portion 24 (refer to FIG. 1 and the like) described above, the housing portion 124 differs in that the housing portion 124 defines an insertion hole into which the tube 28 is inserted, but the other configuration is the same. The insertion hole of the housing portion 124 is formed in a side surface of the housing portion 124, the surface being different from a side surface on which the arm portion 126 is mounted. More specifically, the insertion hole of the housing portion 124 is formed in a side surface of the housing portion 124, in a plan view (refer to FIG. 8 and the like), the side surface facing a central opening region. In such a manner, the position of the tube 28 is not biased to one side of an extending direction of the arm portion 126. For this reason, the compression device 101 is easily used for both the right and left legs.

In addition, a lower end surface on the downward direction A1 side of the housing portion 124 and a lower end on the downward direction A1 side of the expander 121 in the retracted form illustrated in FIG. 9 are located closer to the upward direction A2 side than the mounting surface 12 of the adhesion sheet 2. In other words, the lower end surface of the housing portion 124 and the mounting surface 12 of the adhesion sheet 2 are located separate from each other in the thickness direction A. In addition, the lower end on the downward direction A1 side of the expander 121 in the retracted form illustrated in FIG. 9, and the mounting surface 12 of the adhesion sheet 2 are located separate from each other in the thickness direction A. In such a manner, in the above-described mounting step S1 (refer to FIGS. 5 and 6A to 6D), the compression device 101 can be mounted on the biological surface BS at a proper position for narrowing or obstructing the perforation P (refer to FIG. 34B), for example, a position where the housing portion 124 covers a wound hole of the biological surface BS. Namely, the compression position of the expander 121 (refer to FIG. 9) on the biological surface BS is more easily adjusted.

In comparison to the support portion 25 (refer to FIG. 1 and the like) described above, the support portion 125 is thicker in thickness in the thickness direction A and is larger in rigidity (i.e., is more rigid). In other words, the support portion 125 of the present embodiment is unlikely to be deformed to follow a deformation of the adhesion sheet 2, and holds a substantially constant shape during normal use of the compression device 101. In such a manner, the force with which the support portion 125 lifts the adhesion sheet 2 in the upward direction A2 is easily dispersed in a circumferential direction of the support portion 125. Therefore, the force that lifts the adhesion sheet 2 in the upward direction A2 can be suppressed from being locally concentrated on a part in the circumferential direction of the support portion 125, and the adhesion sheet 2 can be suppressed from locally peeling off from the biological surface.

In addition, as in the present embodiment, the rigidity of the support portion 125 is increased, and thus the arm connection portion 26*b* (refer to FIG. 1) of the first embodiment may be omitted. Furthermore, as in the present embodiment, the rigidity of the support portion 125 is increased, and thus the connection portion 25*b* (refer to FIG. 1) of the support portion 25 of the first embodiment may be omitted.

The arm portion 126 includes an arm main body 126*a* that protrudes from an outer wall of the housing portion 124 to be connected to the support portion 125. More specifically, the arm portion 126 of the present embodiment is formed of only the arm main body 126*a*. The arm main body 126*a* protrudes linearly from the outer wall of the housing portion 124 in a direction orthogonal to the thickness direction A. A plurality (two in the present embodiment) of the arm main bodies 126*a* of the present embodiment are provided, and protrude from the outer wall of the housing portion 124 toward opposite directions.

A projection portion 126*al* is provided on an end surface on an opposite side of each of the arm main bodies 126*a* from a housing portion 124 side. Namely, a health care worker who uses the compression device 101 pinches both the end surfaces of the arm main bodies 126*a* with the fingers, the projection portions 126*al* being formed on the end surfaces, so that the fingers are caught on the projection portions 126*a*1. Therefore, the compression device 101 can be easily gripped. In other words, the both end surfaces of the arm main bodies 126*a*, the projection portions 126*al* being formed on the end surfaces, form a grip portion of the compression device 101. Furthermore, since the projection portions 126*al* are provided, the fingertips are guarded by the support portion 125, and thus the outer edge 13 of the adhesion sheet 2 can be suppressed from being touched and peeled off with the fingers, and the adhesion sheet 2 can be suppressed from being bent.

Third Embodiment

Next, a compression device 201 as a third embodiment will be described with reference to FIGS. 10 to 13B. In the compression device 201 of the present embodiment, the configuration of a compression member differs but the configuration of other aspects of the compression device is the same in comparison to the compression device 101 described above. In the description below, features that are the same or similar to those described above are identified by the same reference numerals and a detailed description of such features is not repeated.

Figure 10:
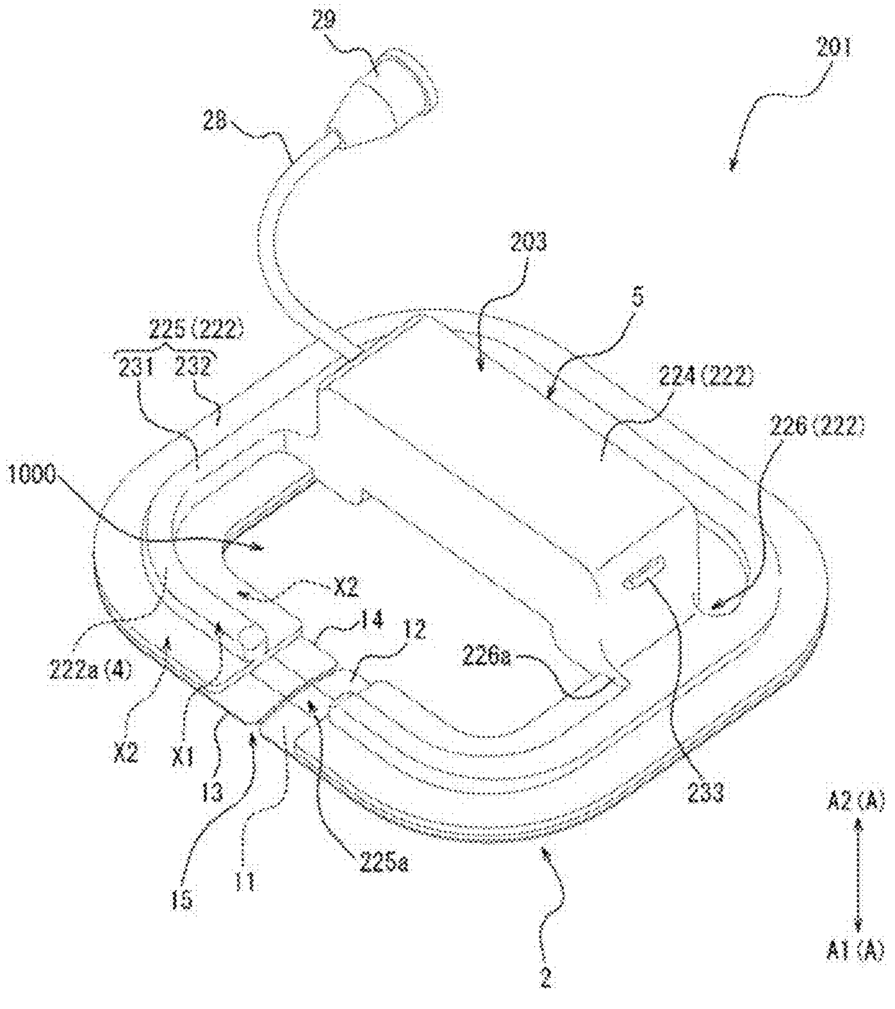
FIG. 10 is a perspective view of a compression device as one embodiment.
Figure 11:
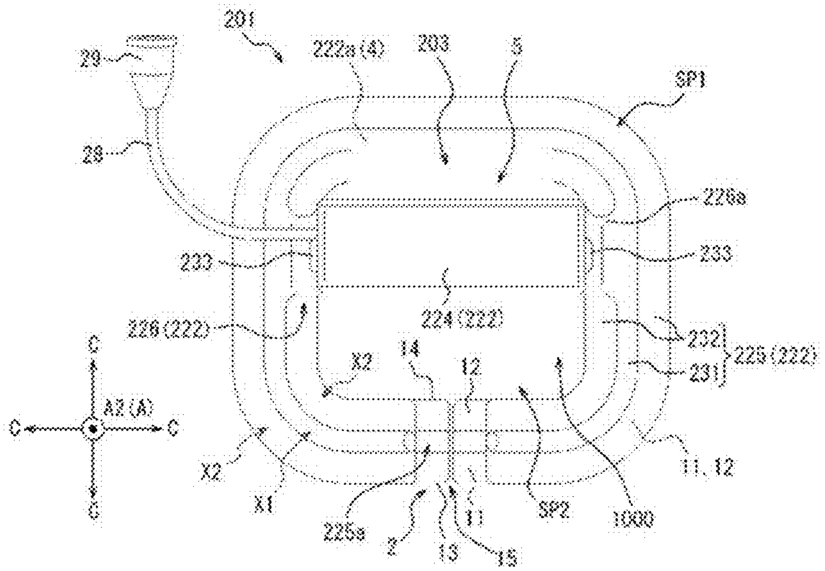
FIG. 11 is a top view of the compression device illustrated in FIG. 10.
Figure 12:
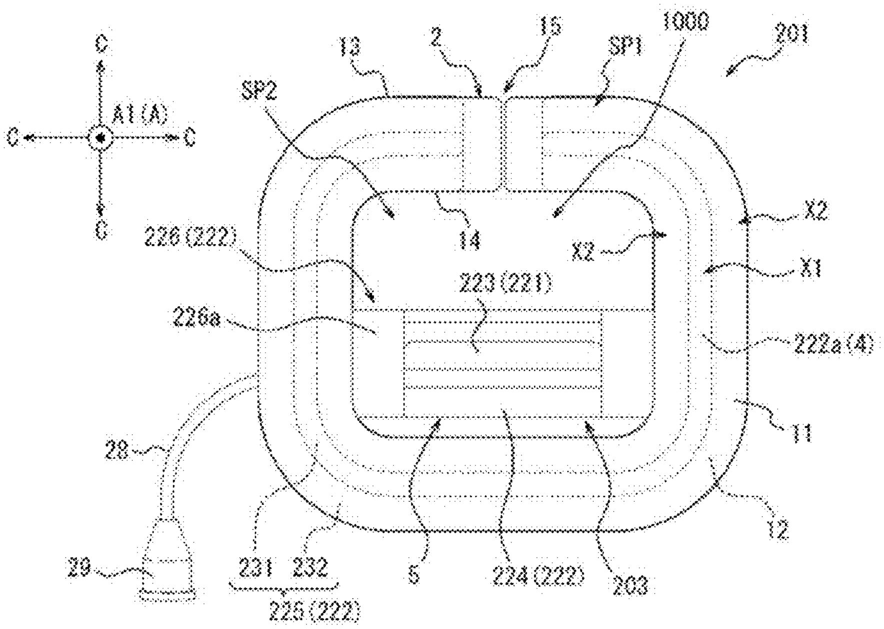
FIG. 12 is a bottom view of the compression device illustrated in FIG. 10.
Figure 13A:
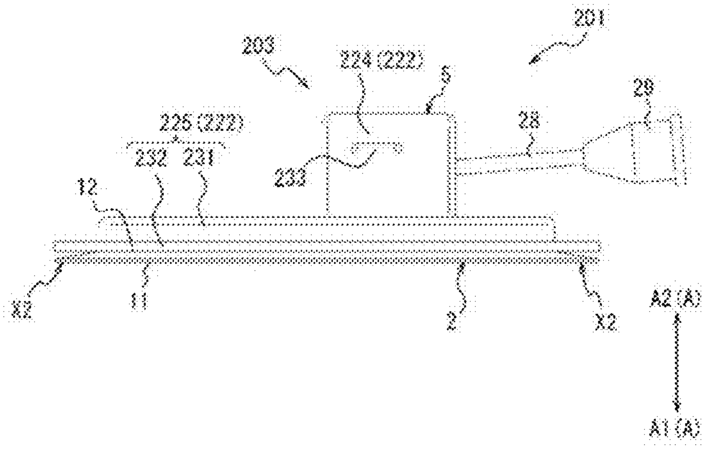
FIG. 13A is a side view of the compression device illustrated in FIG. 10, and is a view illustrating a state where an inflator is in a retracted form.
Figure 13B:
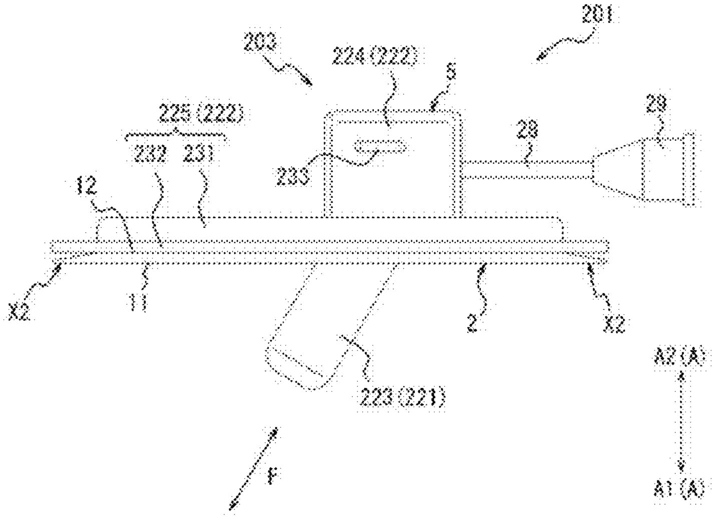
FIG. 13B is a side view of the compression device illustrated in FIG. 10, and is a view illustrating a state where the inflator is in a protruding form.

FIG. 10 is a perspective view of the compression device 201. FIGS. 11 and 12 are plan views of the compression device 201. Specifically, FIG. 11 is a top view of the compression device 201. FIG. 12 is a bottom view of the compression device 201. FIGS. 13A and 13B are side views of the compression device 201. Specifically, FIG. 13A illustrates a state where an inflator 223 (to be described later) of the compression device 201 is in a retracted form. FIG. 13B illustrates a state where the inflator 223 (to be described later) of the compression device 201 is in a protruding form.

The compression device 201 includes the adhesion sheet 2 and a compression member 203. The adhesion sheet 2 includes the adhesion surface 11 that adheres to a biological surface, and the mounting surface 12 that is located on an opposite side of the adhesion sheet 2 from the adhesion surface 11. In a plan view seen along the thickness direction A, the compression member 203 is disposed across the in-edge region SP1 which overlaps the adhesion sheet 2 and the out-of-edge region SP2 which does not overlap the adhesion sheet 2.

The compression member 203 includes the fixing portion 4 and the compression main body portion 5.

The adhesion sheet 2 includes the first portion X1 to which the fixing portion 4 is fixed and the second portion X2 to which the fixing portion 4 is not fixed. In the compression device 201, the second portion X2 is provided on at least the compression main body portion 5 side of the adhesion sheet 2. An adhesion portion made of an adhesive or the like is provided in the adhesion surface 11 of the adhesion sheet 2 at the position of each of the first portion X1 and the second portion X2.

In other words, in the adhesion sheet 2 of the compression device 201, the second portion X2 is provided on at least the compression main body portion 5 side with respect to the first portion X1 of the adhesion sheet 2. More specifically, in the adhesion sheet 2 of the present embodiment, the second portion X2 that continuously extends from the first portion X1 is provided on at least the compression main body portion 5 side with respect to the first portion X1 of the adhesion sheet 2.

As illustrated in FIG. 13B, the compression member 203 of the present embodiment includes an expander 221 that is expandable toward the downward direction A1 of the thickness direction A, and a holder 222 that holds the expander 221.

The fixing portion 4 of the present embodiment described above is formed of a contact surface 222*a* of the holder 222, the contact surface 222*a* being in contact with the adhesion sheet 2 in the in-edge region SP1. The compression main body portion 5 of the present embodiment described above includes the expander 221 and the holder 222.

The expander 221 of the present embodiment is the inflator 223 that is inflatable toward the downward direction A1 of the thickness direction A by supply of a fluid. Similar to the inflator 23 (refer to FIGS. 4A and 4B and the like) and the inflator 123 (refer to FIG. 9), the inflator 223 as the expander 221 of the present embodiment is also changed in form from the retracted form (refer to FIG. 13A) to the protruding form (refer to FIG. 13B), and thus the inflator 223 protrudes further toward the downward direction A1 in the thickness direction A than the adhesion surface 11 of the adhesion sheet 2, to take a posture capable of compressing a biological surface.

Figure 35:
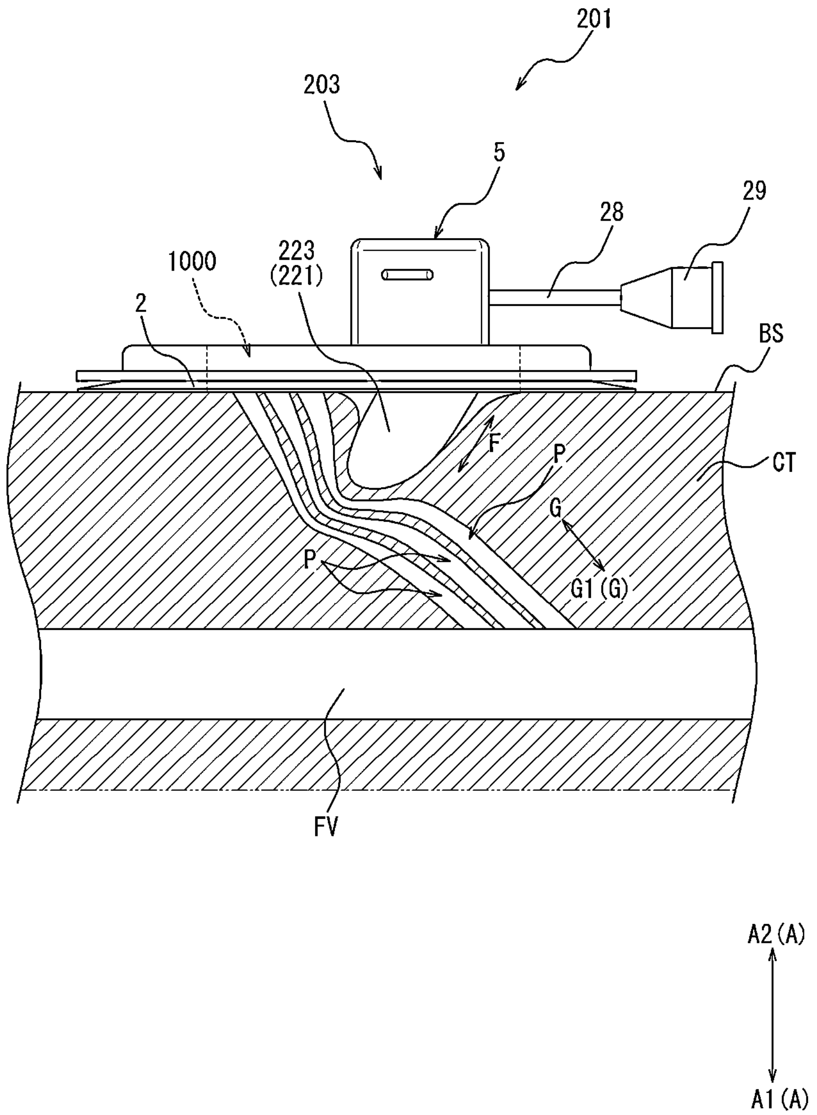
FIG. 35 is a view illustrating a state where a perforation illustrated in FIG. 34B is narrowed or obstructed by the compression device illustrated in FIG. 10.

In addition, as illustrated in FIG. 13B, the inflator 223 is inflatable toward a direction inclined with respect to the thickness direction A. In such a manner, the biological surface can be compressed along a direction orthogonal to the extending direction of the perforation P (refer to FIG. 34B). Specifically, as illustrated in FIGS. 34A and 34B, the sheath as the medical device 100 is inserted not in a direction (the same direction as the thickness direction A) orthogonal to the biological surface BS but in a direction inclined to one side with respect to the direction orthogonal to the biological surface BS. For this reason, as illustrated in FIG. 34B, the extending direction of the perforation P is also inclined with respect to the direction orthogonal to the biological surface BS. Therefore, when the inflator 223 is inflatable in a direction (hereinafter, may be referred to as an "inclination direction F") that is inclined reverse to the extending direction of the perforation P with respect to the thickness direction A which is the direction orthogonal to the biological surface BS, the inflator 223 easily compresses the biological surface BS along the direction orthogonal to the extending direction of the perforation P. The inclination direction F shown in FIG. 35 is inclined relative to the thickness direction A (i.e., the inclination direction F is not parallel to the thickness direction A). Therefore, the compression device 201 that narrows or obstructs the perforation P without obstructing the vein such as the femoral vein FV illustrated in FIGS. 34A and 34B is easily realized. FIG. 35 is a view illustrating a state where the perforation P illustrated in FIG. 34B is narrowed or obstructed by the compression device 201. The compression devices 1 (refer to FIG. 1 and the like) and 101 (refer to FIG. 7 and the like) described above can also narrow or obstruct the perforation P without obstructing the vein such as the femoral vein FV, whereas as illustrated in FIG. 35, according to the compression device 201, the perforation P is more easily narrowed or obstructed without further obstructing the vein such as the femoral vein FV.

An inflation direction of the inflator 223 can be appropriately set by the shape of the inflator 223 itself, the shape of a housing portion 224 (to be described later) that guides the inflation direction of the inflator 223, or the like. In addition, the inflator 223 of the present embodiment is configured to have a flat external shape in the protruding form; however, the shape of the inflator 223 in the protruding form is not limited to the shape. By the way, it is preferable that as in the present embodiment, the inflator 223 has directivity in a protruding direction. In such a manner, the perforation P (refer to FIG. 34B) can be intensively compressed, and the vein can be further suppressed from being obstructed.

The inflator 223 may be a balloon that is inflated by gas such as air. Examples of the material from which the inflator 223 may be fabricated include the same material as the above-described forming material of the inflator 23 (refer to FIG. 4B and the like) can be used.

The holder 222 of the present embodiment includes the housing portion 224 that is located in the out-of-edge region SP2 to accommodate the inflator 223 as the expander 221; a support portion 225 that is located in the in-edge region SP1 to include the contact surface 222*a*; and an arm portion 226 that connects the housing portion 224 and the support portion 225.

In comparison to the housing portion 124 (refer to FIG. 7 and the like) described above, the housing portion 224 has a different external shape, and the external shape of the housing portion 224 can be appropriately designed according to the shape of the inflator 223 or the like. In addition, an insertion hole into which the tube 28 is inserted is formed in the housing portion 224. The insertion hole of the housing portion 224 of the present embodiment is formed in a side surface on which the arm portion 226 is mounted; however, as with the above-described insertion hole of the housing portion 124 (refer to FIG. 7 and the like), the insertion hole may be formed in a side surface different from the side surface on which the arm portion 226 is mounted.

In addition, projection portions 233 are provided on opposite side surfaces of the housing portion 224 of the present embodiment. Namely, a health care worker who uses the compression device 201 pinches the side surfaces of the housing portion 224 with the fingers, the projection portions 233 being formed on the side surfaces, so that the fingers are caught on the projection portions 233. Therefore, the compression device 201 can be easily gripped. In other words, both the side surfaces of the housing portion 224, the projection portions 233 being formed on the side surfaces, form a grip portion of the compression device 201. Furthermore, since the projection portions 233 are provided, the fingertips are guarded by the support portion 225, and thus the outer edge 13 of the adhesion sheet 2 can be suppressed from being touched and peeled off with the fingers, and the adhesion sheet 2 can be suppressed from being bent.

In addition, similar to the compression device 101 described above, a lower end surface on the downward direction A1 side of the housing portion 224 and a lower end on the downward direction A1 side of the expander 221 in the retracted form illustrated in FIG. 12 are located closer to the upward direction A2 side than the mounting surface 12 of the adhesion sheet 2. In such a manner, in the above-described mounting step S1 (refer to FIGS. 5 and 6A to 6D), the compression device 201 is mountable on the biological surface BS at a proper position for narrowing or obstructing the perforation P (refer to FIG. 34B), for example, a position where the housing portion 224 covers a wound hole of the biological surface BS. Namely, the compression position of the expander 221 (refer to FIG. 13B) on the biological surface BS is more easily adjusted.

The point of difference between the support portion 225 and the support portion 125 (refer to FIG. 7 and the like) described above is whether or not a flange portion is provided. The support portion 225 of the present embodiment includes a support main body portion 231 and a flange portion 232. The support main body portion 231 extends in an annular shape along the adhesion sheet 2 having an annular shape. The flange portion 232 protrudes from an end portion of the support main body portion 231 in the downward direction A1 of the support main body portion 231, and also extends inward and outward in the radial direction C with respect to the support main body portion 231. Surfaces of the support main body portion 231 and the flange portion 232 in the downward direction A1 are flush with each other to form one flat surface. The upward direction A2 of the adhesion sheet 2 extending in an annular shape is covered by the support main body portion 231 and the flange portion 232.

As described above, the fixing portion 4 of the present embodiment is formed of the contact surface 222*a* of the holder 222, the contact surface 222*a* being in contact with the adhesion sheet 2 in the in-edge region SP1. More specifically, the fixing portion 4 of the present embodiment is formed of a lower surface of the support main body portion 231 in a lower surface as the contact surface 222*a* of the support portion 225. In other words, the lower surface of the support main body portion 231 is fixed to the mounting surface 12 of the adhesion sheet 2 by adhesion or the like, whereas the lower surface of the flange portion 232 covers the mounting surface 12 without being fixed to the mounting surface 12 of the adhesion sheet 2, and can come into contact with and is separable from the mounting surface 12 in the thickness direction A.

Even with such a configuration where the flange portion 232 is provided, since the flange portion 232 is not fixed to the mounting surface 12, force that peels the adhesion sheet 2 off from the inner edge 14 is unlikely to be applied. Meanwhile, since the flange portion 232 is provided, in comparison to the support portion 125 (refer to FIG. 7), the area by which the support portion 225 covers the mounting surface 12 of the adhesion sheet 2 can be increased. For this reason, when the adhesion sheet 2 adheres to the biological surface, the area of the adhesion surface 11 of the adhesion sheet 2 pressed to a biological surface side via the support portion 225 is increased. Namely, since the support portion 225 is pressed toward the biological surface, a wider range of the adhesion surface 11 of the adhesion sheet 2 (in the present embodiment, the entire region of the adhesion surface 11 of the adhesion sheet 2) can be pressed toward the biological surface. Therefore, the operability in the mounting step S1 (refer to FIGS. 5 and 6A to 6D) of the compression device 201 is improved.

The flange portion 232 of the present embodiment covers the entire region of the mounting surface 12 of the adhesion sheet 2; however, the present disclosure is not limited to this configuration, and the flange portion may cover a part of the mounting surface 12. According to the configuration where as in the present embodiment, the flange portion 232 covers the entire region of the mounting surface 12 of the adhesion sheet 2, since the support portion 225 is pressed toward the biological surface, the entire region of the adhesion surface 11 of the adhesion sheet 2 can be pressed against the biological surface, and thus the operability in the mounting step S1 (refer to FIGS. 5 and 6A to 6D) of the compression device 201 is further improved.

In addition, as in the present embodiment, it is preferable that the flange portion 232 is provided inside and outside the support main body portion 231 in the radial direction C. However, the flange portion 232 may be configured to be provided on either one of inside and outside the support main body portion 231 in the radial direction C. In the configuration where the flange portion 232 is provided on either one, it is preferable that the flange portion 232 is provided inside the support main body portion 231 in the radial direction C. A space between the support main body portion 231 and the housing portion 224 is a relatively small space for inserting the fingers, and so if the flange portion 232 is not provided inside the support main body portion 231, it may be difficult to press the portion of the adhesion sheet 2 toward the biological surface. On the other hand, when the flange portion 232 is provided inside the support main body portion 231 in the radial direction C, the portion of the adhesion sheet 2 which is located between the support main body portion 231 and the housing portion 224 can be easily pressed toward the biological surface via the flange portion 232.

The arm portion 226 includes an arm main body 226*a* that protrudes from an outer wall of the housing portion 224 to be connected to the support portion 225. More specifically, the arm portion 226 of the present embodiment is formed of only the arm main body 226*a*. The arm main body 226*a* protrudes from the outer wall of the housing portion 224 in the direction orthogonal to the thickness direction A. A plurality (two in the present embodiment) of the arm main bodies 226*a* of the present embodiment are provided, and protrude from the outer wall of the housing portion 224 toward opposite directions.

Fourth Embodiment

Next, a compression device 301 as a fourth embodiment will be described with reference to FIGS. 14 to 17. Here, the point of difference from the compression device 1 (refer to FIG. 1 and the like) described above will be mainly described. In the description below, features that are the same or similar to those described above are identified by the same reference numerals and a detailed description of such features is not repeated.

Figure 14:
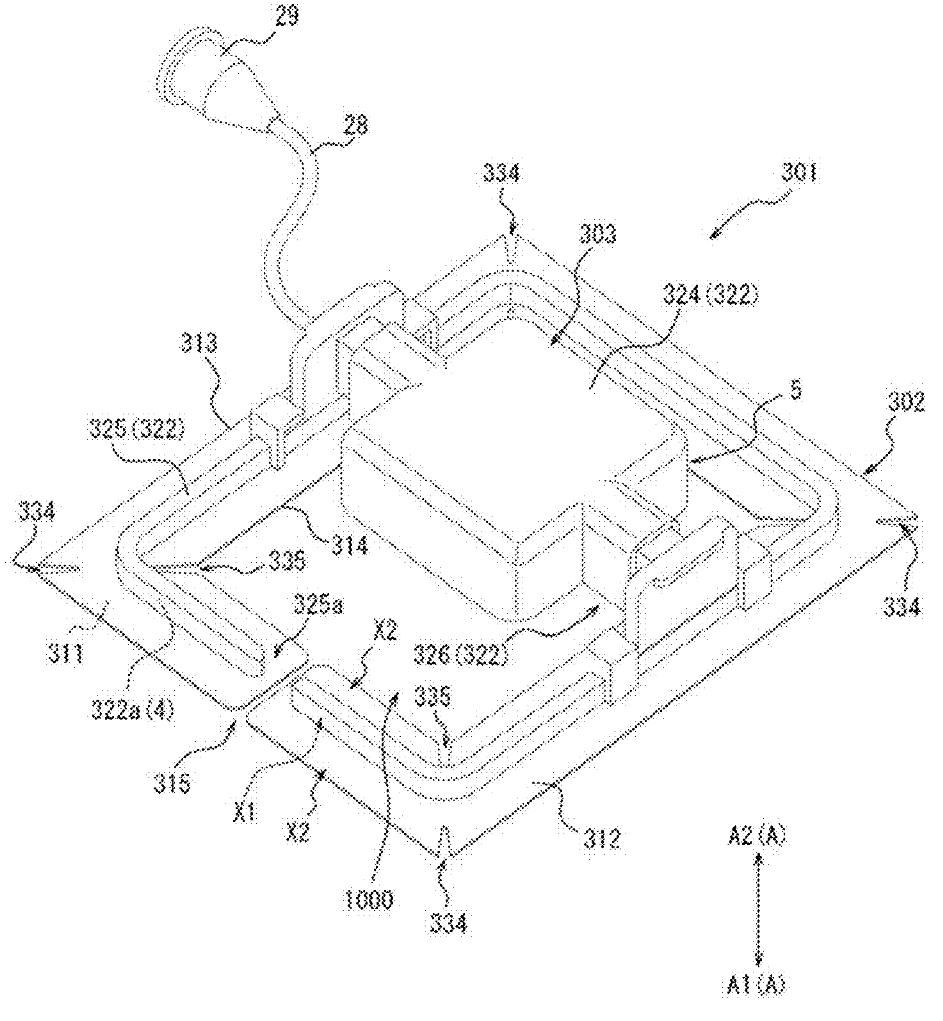
FIG. 14 is a perspective view of a compression device as one embodiment.
Figure 15:
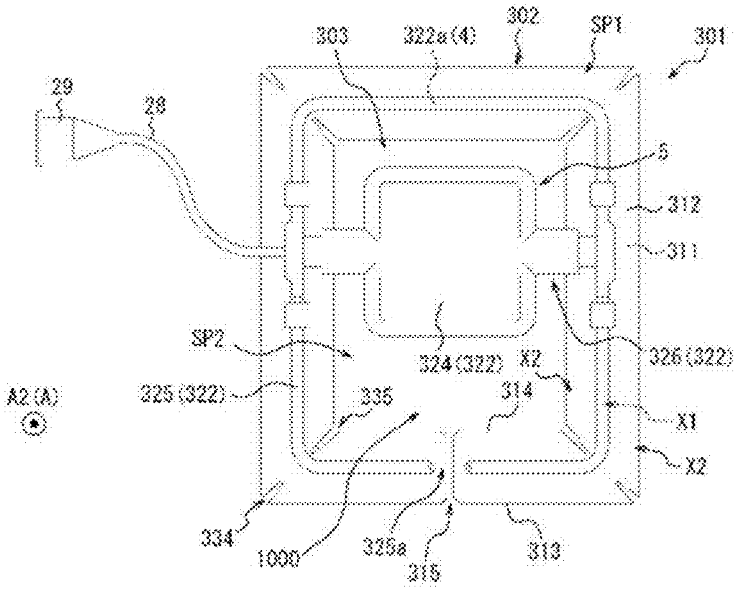
FIG. 15 is a top view of the compression device illustrated in FIG. 14.
Figure 16:
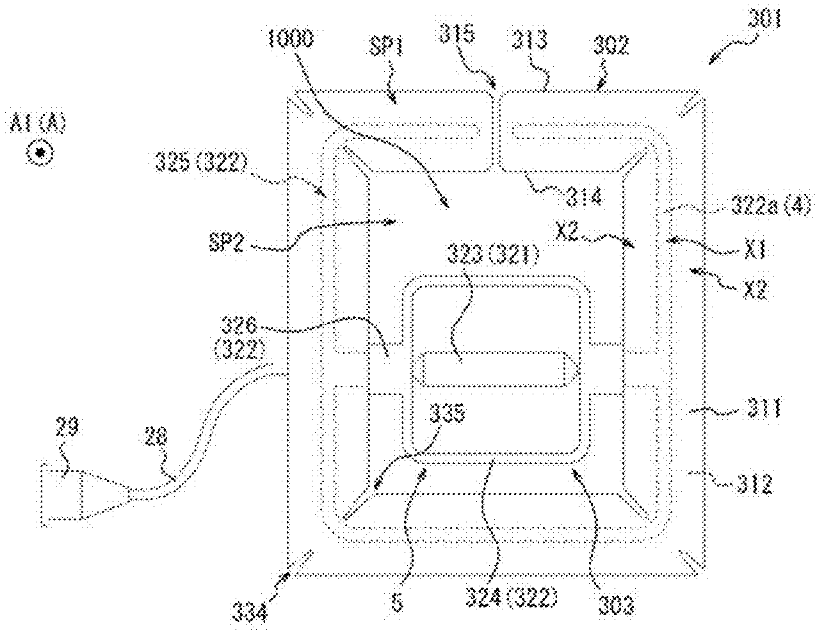
FIG. 16 is a bottom view of the compression device illustrated in FIG. 14.
Figure 17:
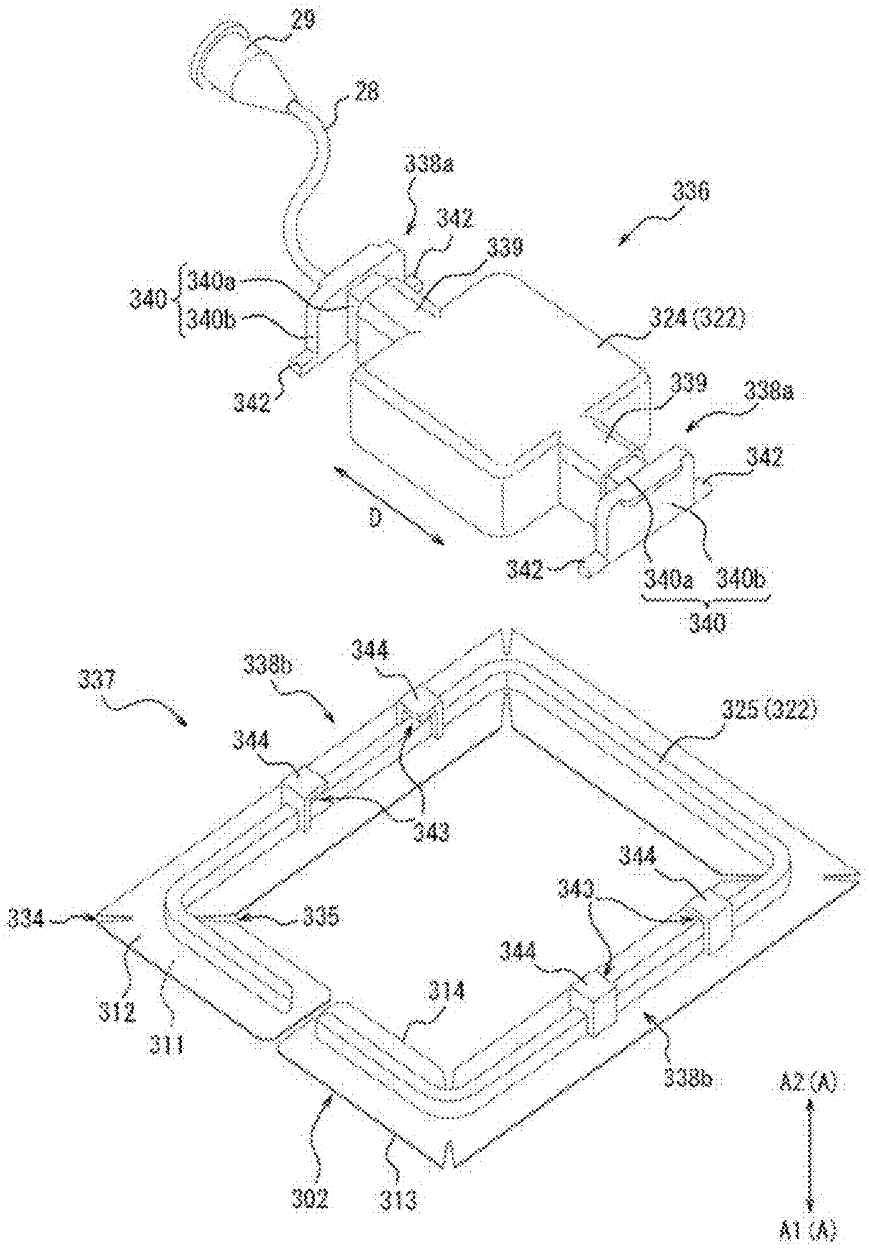
FIG. 17 is an exploded perspective view of the compression device illustrated in FIG. 14.

FIG. 14 is a perspective view of the compression device 301. FIGS. 15 and 16 are plan views of the compression device 301. Specifically, FIG. 15 is a top view of the compression device 301. FIG. 16 is a bottom view of the compression device 301. FIG. 17 is an exploded perspective view of the compression device 301.

The compression device 301 includes an adhesion sheet 302 and a compression member 303. The adhesion sheet 302 includes an adhesion surface 311 that adheres to a biological surface, and a mounting surface 312 that is located on an opposite side of the adhesion sheet 302 from the adhesion surface 311. In a plan view seen along the thickness direction A, the compression member 303 is disposed across the in-edge region SP1 which overlaps the adhesion sheet 302 and the out-of-edge region SP2 which does not overlap the adhesion sheet 302.

The compression member 303 includes the fixing portion 4 and the compression main body portion 5.

The adhesion sheet 302 includes the first portion X1 to which the fixing portion 4 is fixed and the second portion X2 to which the fixing portion 4 is not fixed. In the compression device 301, the second portion X2 is provided on at least a compression main body portion 5 side of the adhesion sheet 302. An adhesion portion made of an adhesive or the like is provided in the adhesion surface 311 of the adhesion sheet 302 at the position of each of the first portion X1 and the second portion X2.

In other words, in the adhesion sheet 302 of the compression device 301, the second portion X2 is provided on at least the compression main body portion 5 side with respect to the first portion X1 of the adhesion sheet 302. More specifically, in the adhesion sheet 302 of the present embodiment, the second portion X2 that continuously extends from the first portion X1 is provided on at least the compression main body portion 5 side with respect to the first portion X1 of the adhesion sheet 302.

In comparison to the adhesion sheet 2 (refer to FIG. 1 and the like) described above, the adhesion sheet 302 has a different external shape. The outer edge 13 (refer to FIG. 1 and the like) and the inner edge 14 (refer to FIG. 1 and the like) of the adhesion sheet 2 describe above have an oval shape, but an outer edge 313 and an inner edge 314 of the adhesion sheet 302 illustrated in FIGS. 14 to 17 have a rectangular shape. In addition, a slit 334 that extends from the outer edge 313 toward the inner edge 314 but does not reach the inner edge 314 is formed in each of four corners of the outer edge 313 of the adhesion sheet 302. Furthermore, a slit 335 that extends from the inner edge 314 toward the outer edge 313 but does not reach the outer edge 313 is also formed in each of four corners of the inner edge 314 of the adhesion sheet 302. Since the slits 334 and 335 described above are provided, the followability of the adhesion sheet 302 with respect to the biological surface can be improved.

The compression member 303 of the present embodiment includes an expander 321 that is expandable toward the downward direction A1 of the thickness direction A, and a holder 322 that holds the expander 321.

The fixing portion 4 of the present embodiment described above is formed of a contact surface 322*a* of the holder 322, the contact surface 322*a* being in contact with the adhesion sheet 302 in the in-edge region SP1. The compression main body portion 5 of the present embodiment described above includes the expander 321 and the holder 322.

The expander 321 of the present embodiment is an inflator 323 that is inflatable toward the downward direction A1 of the thickness direction A by supply of a fluid, and has the same above-described configuration as the inflator 23 of the compression device 1.

The holder 322 of the present embodiment includes a housing portion 324 that is located in the out-of-edge region SP2 to accommodate the inflator 323 as the expander 321; a support portion 325 that is located in the in-edge region SP1 to include the contact surface 322*a*; and an arm portion 326 that connects the housing portion 324 and the support portion 325.

As illustrated in FIG. 17, the holder 322 of the present embodiment is configured to be disassemblable. Specifically, the holder 322 can be disassembled into a first member 336 including the housing portion 324 and a second member 337 including the support portion 325.

The first member 336 of the present embodiment includes a first arm forming portion 338*a* connectable to the second member 337, in addition to the housing portion 324. In addition, the second member 337 of the present embodiment includes a second arm forming portion 338*b* connectable to the first member 336, in addition to the support portion 325. When the first arm forming portion 338*a* of the first member 336 and the second arm forming portion 338*b* of the second member 337 are connected, the arm portion 326 is formed and the housing portion 324 and the support portion 325 are connected.

The first arm forming portion 338*a* includes a tubular portion 339 which protrudes from the housing portion 324 and has an open distal end, and a movable portion 340 of which a part is accommodated in the tubular portion 339, another part protrudes from a distal end opening of the tubular portion 339, and is movable in an axial direction of the tubular portion 339. The movable portion 340 includes a main body portion 340*a* that extends from inside the tubular portion 339 to outside the tubular portion 339 through the distal end opening, and a plate-shaped flange portion 340*b* that is provided at a distal end of the main body portion 340*a*. The movable portion 340 is biased from inside the tubular portion 339 toward the distal end opening by a biasing member such as a coil spring. When the movable portion 340 is moved against the biasing force of the biasing member, the plate-shaped flange portion 340*b* is movable to approach the housing portion 324.

A projecting portion 342 that is accommodated in a recessed portion 343 of the second arm forming portion 338*b* (to be described later) is formed in the plate-shaped flange portion 340*b*.

The first arm forming portions 338*a* described above are provided on one end side of the first member 336 and on the other end side thereof which is an opposite side.

The second arm forming portion 338*b* includes a receiving portion 344 that protrudes from the support portion 325 to define the recessed portion 343 which is open toward an inner edge 314 side of the adhesion sheet 302.

The second arm forming portions 338*b* described above are provided on one end side of the second member 337 and on the other end side thereof which is an opposite side.

When the projecting portion 342 of the plate-shaped flange portion 340*b* of the first arm forming portion 338*a* is fitted into the recessed portion 343 of the receiving portion 344 of the second arm forming portion 338*b*, the first arm forming portion 338*a* and the second arm forming portion 338*b* are connected. Hereinafter, a method for connecting the first arm forming portion 338*a* and the second arm forming portion 338*b* will be described.

First, two movable portions 340 of the first arm forming portions 338*a* are moved to a housing portion 324 side against the biasing forces of the biasing members. Therefore, the total length of the first member 336 in an axial direction D of the tubular portion 339 can be shortened. In this state, the first member 336 is disposed at a position between two second arm forming portions 338*b* of the second member 337 and forces against the biasing forces are released, so that the first member 336 extends in the axial direction D. Therefore, the projecting portions 342 of the plate-shaped flange portions 340*b* of the first arm forming portions 338*a* of the first member 336 are inserted into the recessed portions 343 of the receiving portions 344 of the second arm forming portions 338*b*. In a state where the projecting portions 342 are inserted into the recessed portions 343, unless the first member 336 is deformed to be shortened in the axial direction D against the biasing forces of the biasing members, a relative movement of the first member 336 with respect to the second member 337 is restricted. Namely, the first member 336 is connected to the second member 337, so that the arm portion 326 is formed.

The configuration of the first arm forming portion 338*a* and the second arm forming portion 338*b* where the holder 322 can be disassembled is not limited to the configuration illustrated in the present embodiment, and may be another configuration.

Since the holder 322 is configured to be disassemblable or to be disassembled, when a patient has a weak skin, the first member 336 which is disturbing is removed, and it is then possible to wait for the second member 337 to spontaneously peel off. In addition, in such a manner, the second member 337 is not required to be forcibly removed from the biological surface of the patient, and it becomes easier to use an adhesive having higher adhesiveness.

Fifth Embodiment

Next, a compression device 401 as a fifth embodiment will be described with reference to FIGS. 18 to 20. The following description will mainly focus on the point of difference relative to the compression device 1 (refer to FIG. 1 and the like), and features that are the same or similar to those described above are identified by the same reference numerals and a detailed description of such features is not repeated.

Figure 18:
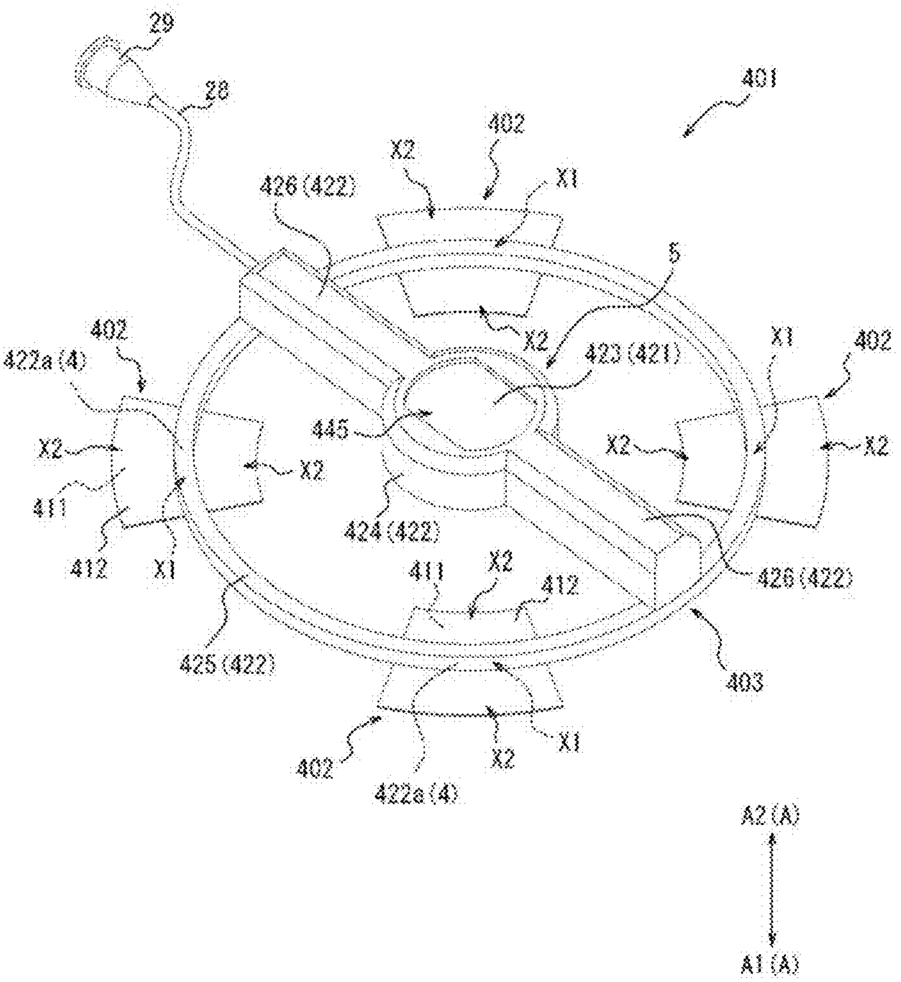
FIG. 18 is a perspective view of a compression device as one embodiment.

FIG. 18 is a perspective view of the compression device 401. FIGS. 19 and 20 are plan views of the compression device 401. Specifically, FIG. 19 is a top view of the compression device 401. FIG. 20 is a bottom view of the compression device 401.

The compression device 401 includes an adhesion sheet 402 and a compression member 403. The adhesion sheet 402 includes an adhesion surface 411 that adheres to a biological surface, and a mounting surface 412 that is located on an opposite side of the adhesion sheet 402 from the adhesion surface 411. In a plan view seen along the thickness direction A, the compression member 403 is disposed across the in-edge region SP1 which overlaps the adhesion sheet 402 and the out-of-edge region SP2 which does not overlap the adhesion sheet 402.

The compression member 403 includes the fixing portion 4 and the compression main body portion 5.

The adhesion sheet 402 includes the first portion X1 to which the fixing portion 4 is fixed and the second portion X2 to which the fixing portion 4 is not fixed. In the compression device 401, the second portion X2 is provided on at least a compression main body portion 5 side of the adhesion sheet 402. An adhesion portion made of an adhesive or the like is provided in the adhesion surface 411 of the adhesion sheet 402 at the position of each of the first portion X1 and the second portion X2.

In other words, in the adhesion sheet 402 of the compression device 401, the second portion X2 is provided on at least the compression main body portion 5 side with respect to the first portion X1 of the adhesion sheet 402. More specifically, in the adhesion sheet 402 of the present embodiment, the second portion X2 that continuously extends from the first portion X1 is provided on at least the compression main body portion 5 side with respect to the first portion X1 of the adhesion sheet 402.

In comparison to the adhesion sheet 2 (refer to FIG. 1 and the like) described above, the adhesion sheet 402 has a different external shape. The adhesion sheet 2 described above is configured to extend in an annular shape over substantially the entire region in the circumferential direction of the support portion 25 (refer to FIG. 1 and the like) of the compression member 3 (refer to FIG. 1 and the like), whereas a plurality of the adhesion sheets 402 illustrated in FIGS. 18 to 20 are intermittently disposed at intervals along a circumferential direction of a support portion 425 (to be described later) of the compression member 403. Since the adhesion sheets 402 are intermittently disposed, the adhesion area adhering to the biological surface can be reduced. For this reason, a rash caused by adhesion or a pain when the adhesion sheet is peeled off can be reduced.

Each of the adhesion sheets 402 of the present embodiment may have a substantially trapezoidal external shape, but is not limited to this shape, and various shapes such as an oval shape, a circular shape, and a rectangular shape can be used.

In addition, four adhesion sheets 402 of the present embodiment are disposed at substantially equal intervals along the circumferential direction of the support portion 425 (to be described later); however, the present disclosure is not limited to this configuration and the distance between the adhesion sheets adjacent to each other in the circumferential direction and the number of the adhesion sheets disposed can be appropriately changed.

The compression member 403 of the present embodiment includes an expander 421 that is expandable toward the downward direction A1 of the thickness direction A, and a holder 422 that holds the expander 421.

The fixing portion 4 of the present embodiment described above is formed of a contact surface 422*a* of the holder 422, the contact surface 422*a* being in contact with the adhesion sheet 402 in the in-edge region SP1. The compression main body portion 5 of the present embodiment described above includes the expander 421 and the holder 422.

The expander 421 of the present embodiment is an inflator 423 that is inflatable toward the downward direction A1 of the thickness direction A by supply of a fluid. Similar to the inflator 23 (refer to FIG. 4B and the like) described above, the inflator 423 as the expander 421 of the present embodiment is also changed in form from a retracted form to a protruding form, and thus the inflator 423 protrudes further toward the downward direction A1 in the thickness direction A than the adhesion surface 411 of the adhesion sheet 402, to take a posture capable of compressing the biological surface.

Figure 19:
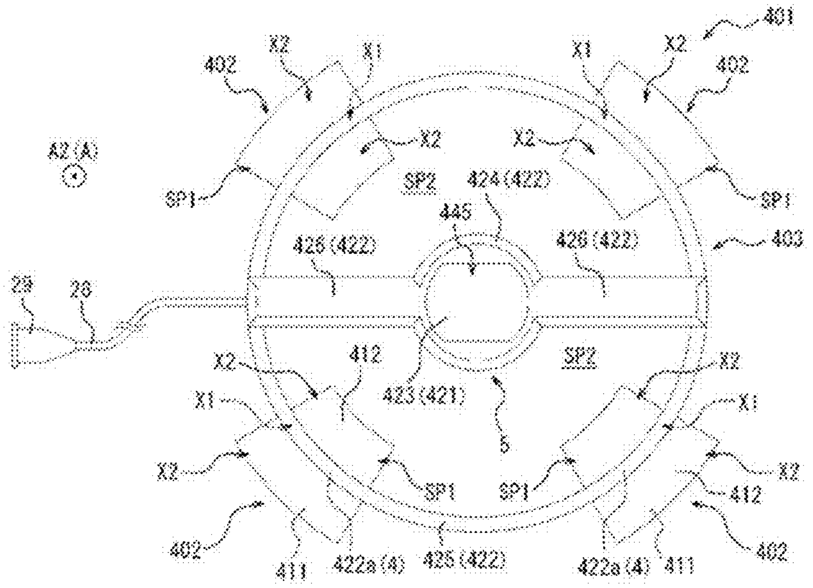
FIG. 19 is a top view of the compression device illustrated in FIG. 18.
Figure 20:
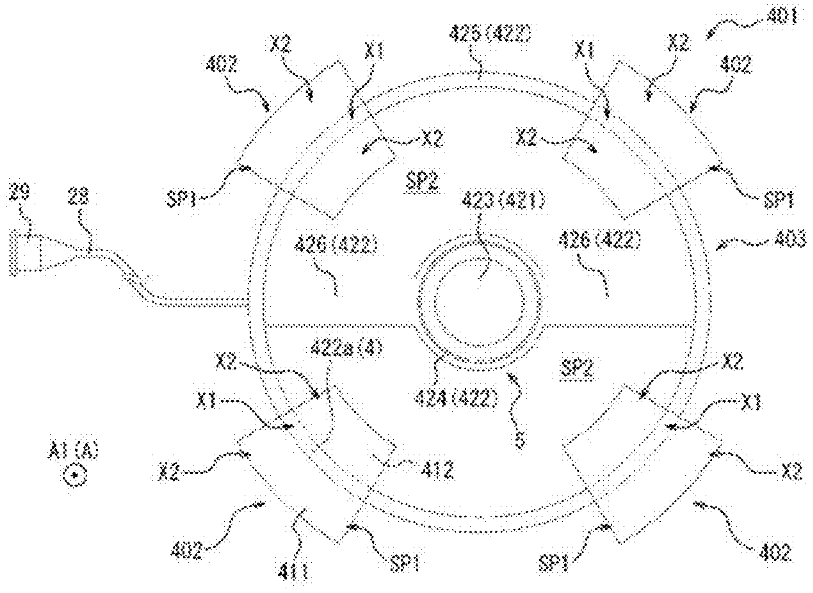
FIG. 20 is a bottom view of the compression device illustrated in FIG. 18.

FIGS. 18 to 20 illustrate the inflator 423 in the retracted form. As illustrated in FIGS. 18 to 20, when in the retracted form, the inflator 423 of the present embodiment is disposed in a recessed portion of the holder 422. When in the retracted form, the inflator 423 of the present embodiment defines a substantially columnar internal space. A fluid is supplied through the tube 28 to the internal space of the inflator 423 from a fluid supply device to be connected to the connection portion 29 provided in the end portion of the tube 28. Therefore, the inflator 423 can be changed in form from the retracted form to the protruding form.

As illustrated in FIGS. 18 and 19, in the holder 422 of the present embodiment, an opening portion 445 is formed on an upward direction A2 side of the inflator 423. Namely, in the compression device 401 of the present embodiment, the inflator 423 is exposed outside the holder 422 through the opening portion 445. In addition, the inflator 423 is made of an ultrasound transmitting material. In addition, an ultrasound transmitting fluid such as water or gel is also used as the fluid to be supplied to the inflator 423. With such a configuration, even in a configuration where the holder 422 is not made of an ultrasound transmitting material, an obstructed state of a vein caused by the compression device 401 can be detected through the opening portion 445 and the inflator 423 by the ultrasound device.

The holder 422 of the present embodiment includes a housing portion 424 that is located in the out-of-edge region SP2 to accommodate the inflator 423 as the expander 421; the support portion 425 that is located in the in-edge region SP1 and the out-of-edge region SP2 to include the contact surface 422*a*; and an arm portion 426 that connects the housing portion 424 and the support portion 425.

The contact surface 422*a* of the present embodiment is formed of a portion of a lower surface of the support portion 425, the portion being in contact with each of the adhesion sheets 402.

The opening portion 445 described above is formed at the position of the housing portion 424 of the holder 422. In comparison to the housing portion 24 (refer to FIG. 1 and the like), the support portion 25 (refer to FIG. 1 and the like), and the arm portion 26 (refer to FIG. 1 and the like), the housing portion 424, the support portion 425, and the arm portion 426 have different external shapes; however, the external shapes of the housing portion 424, the support portion 425, and the arm portion 426 are not limited to the shapes of the present embodiment and can be appropriately changed.

Sixth Embodiment

Next, a compression device 501 as a sixth embodiment will be described with reference to FIGS. 21 to 23. The following description will mainly focus on the point of difference relative to the compression device 1 (refer to FIG. 1 and the like) described above, and features that are the same or similar to those described above are identified by the same reference numerals and a detailed description of such features is not repeated.

Figure 21:
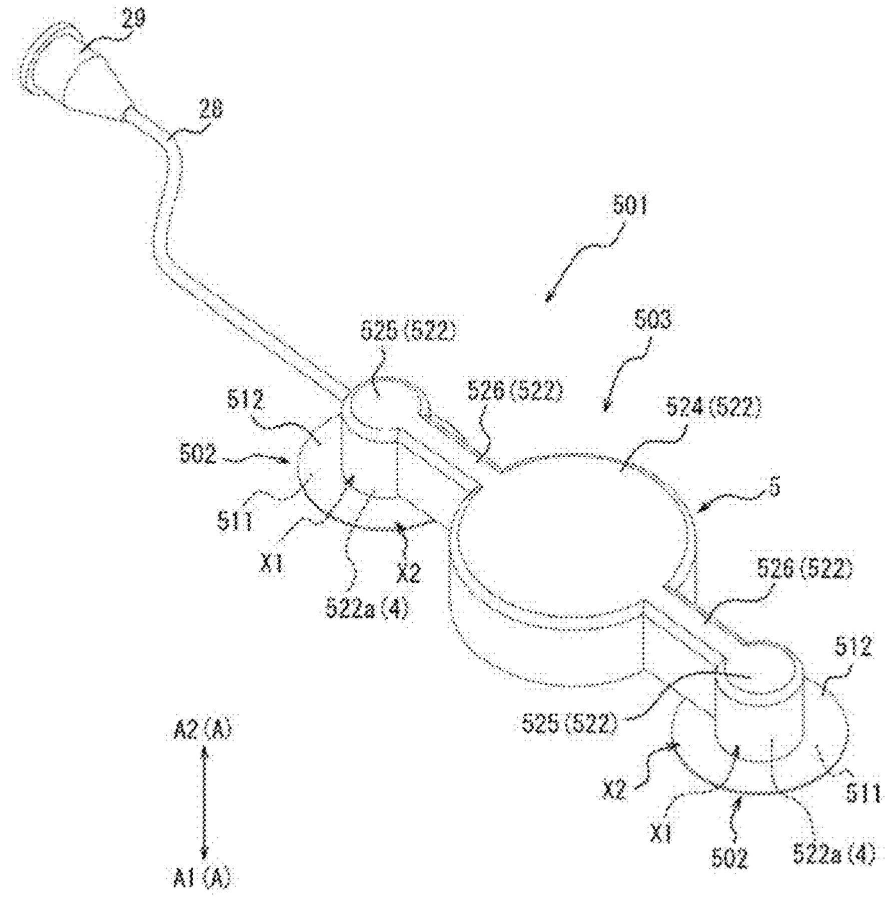
FIG. 21 is a perspective view of a compression device as one embodiment.

FIG. 21 is a perspective view of the compression device 501. FIGS. 22 and 23 are plan views of the compression device 501. Specifically, FIG. 22 is a top view of the compression device 501. FIG. 23 is a bottom view of the compression device 501.

The compression device 501 includes an adhesion sheet 502 and a compression member 503. The adhesion sheet 502 includes an adhesion surface 511 that adheres to a biological surface, and a mounting surface 512 that is located on an opposite side of the adhesion sheet 502 from the adhesion surface 511. In a plan view seen along the thickness direction A, the compression member 503 is disposed across the in-edge region SP1 which overlaps the adhesion sheet 502 and the out-of-edge region SP2 which does not overlap the adhesion sheet 502.

The compression member 503 includes the fixing portion 4 and the compression main body portion 5.

The adhesion sheet 502 includes the first portion X1 to which the fixing portion 4 is fixed and the second portion X2 to which the fixing portion 4 is not fixed. In the compression device 501, the second portion X2 is provided on at least a compression main body portion 5 side of the adhesion sheet 502. An adhesion portion made of an adhesive or the like is provided in the adhesion surface 511 of the adhesion sheet 502 at the position of each of the first portion X1 and the second portion X2.

In other words, in the adhesion sheet 502 of the compression device 501, the second portion X2 is provided on at least the compression main body portion 5 side with respect to the first portion X1 of the adhesion sheet 502. More specifically, in the adhesion sheet 502 of the present embodiment, the second portion X2 that continuously extends from the first portion X1 is provided on at least the compression main body portion 5 side with respect to the first portion X1 of the adhesion sheet 502.

The compression member 503 of the present embodiment includes an expander 521 that is expandable toward the downward direction A1 of the thickness direction A, and a holder 522 that holds the expander 521.

The fixing portion 4 of the present embodiment described above is formed of a contact surface 522*a* of the holder 522, the contact surface 522*a* being in contact with the adhesion sheet 502 in the in-edge region SP1. The compression main body portion 5 of the present embodiment described above includes the expander 521 and the holder 522.

The expander 521 of the present embodiment is an inflator 523 that is inflatable toward the downward direction A1 of the thickness direction A by supply of a fluid. Similar to the inflator 23 (refer to FIG. 4B and the like) described above, the inflator 523 as the expander 521 of the present embodiment is also changed in form from a retracted form to a protruding form, and thus the inflator 523 protrudes further toward the downward direction A1 in the thickness direction A than the adhesion surface 511 of the adhesion sheet 502, to take a posture capable of compressing the biological surface.

The holder 522 of the present embodiment includes a housing portion 524 that is located in the out-of-edge region SP2 to accommodate the inflator 523 as the expander 521; a support portion 525 that is located in the in-edge region SP1 to include the contact surface 522*a*; and an arm portion 526 that connects the housing portion 524 and the support portion 525.

In the compression device 501 of the present embodiment, the shape of the adhesion sheet and the shape of the support portion of the compression member differ in comparison to the compression device 1 (refer to FIG. 1 and the like) described above.

Specifically, the support portion 525 of the present embodiment has a columnar external shape of which the axial direction substantially coincides with the thickness direction A, and the arm portion 526 is connected to a peripheral surface of the support portion 525. The contact surface 522*a* of the present embodiment is formed of the entire region of a lower surface that is one bottom surface of the support portion 525 having a columnar shape. In such a manner, in a plan view (refer to FIG. 22 and the like), the support portion 525 of the present embodiment is not formed in an annular shape, and one support portion 525 is provided on each of both sides with the housing portion 524 interposed between the support portions 525. In other words, in the present embodiment, the housing portion 524, two support portions 525, and two arm portions 526 are linearly arranged in a plan view (refer to FIG. 22 and the like).

In addition, the adhesion sheet 502 of the present embodiment is disposed on a lower surface side of each of the support portions 525. Specifically, each of the adhesion sheets 502 has a circular outer edge, and includes a central portion as the first portion X1 which is in contact with and fixed to the lower surface of each of the support portions 525, and a peripheral edge portion as the second portion X2 which extends from the first portion X1 in a radial direction.

Figure 22:
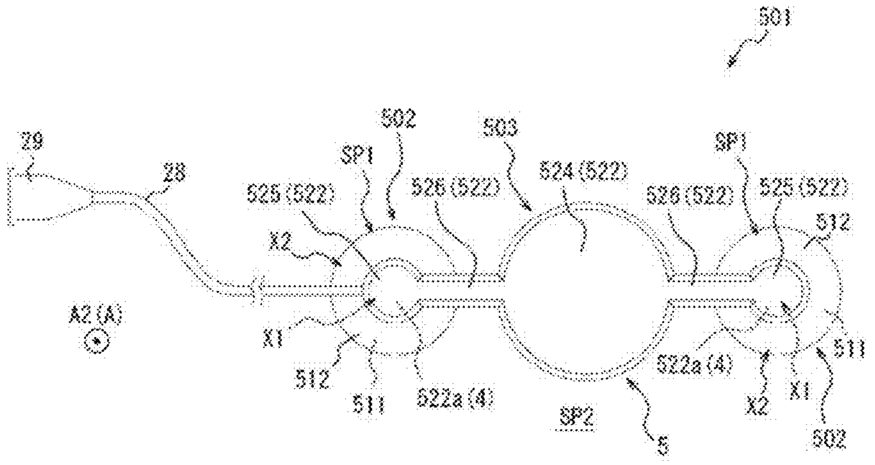
FIG. 22 is a top view of the compression device illustrated in FIG. 21.
Figure 23:
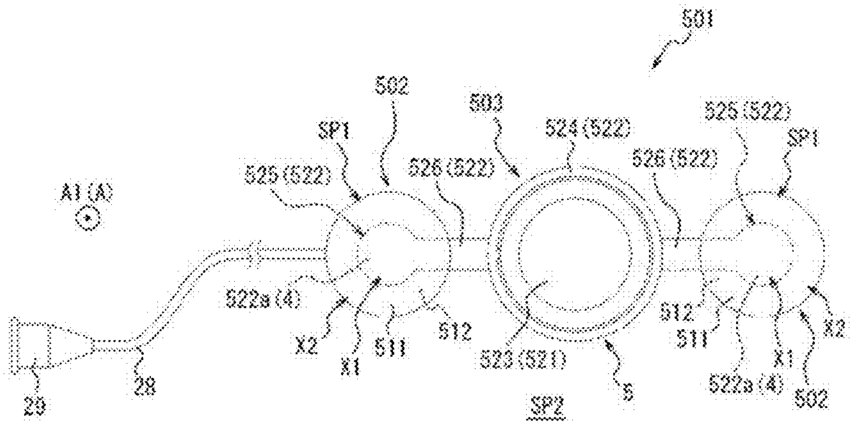
FIG. 23 is a bottom view of the compression device illustrated in FIG. 21.

As illustrated in FIG. 22, in a plan view, a part of the arm portion 526 of the present embodiment overlaps the adhesion sheet 502, namely, is located in the in-edge region SP1, but the arm portion 526 is not fixed to the adhesion sheet 502 and the adhesion sheet 502 is separable from a lower surface on the downward direction A1 side of the arm portion 526.

The number of the support portions 525 and the adhesion sheets 502 is not limited to 2 as in the present embodiment and may be, for example, 3 or more. In addition, the shape of each of the support portions 525 of the present embodiment is not limited to a columnar shape and may be, for example, a prismatic shape or the like. Furthermore, the shape of the outer edge of each of the adhesion sheets 502 of the present embodiment is not limited to a circular shape and may be, for example, a polygonal shape, an elliptical shape, or the like.

Seventh Embodiment

Next, a compression device 601 as a seventh embodiment will be described with reference to FIGS. 24 to 27. The following description will mainly focus on the point of difference relative to the compression device 501 (refer to FIG. 21 and the like), and features that are the same or similar to those described above are identified by the same reference numerals and a detailed description of such features is not repeated.

Figure 24:
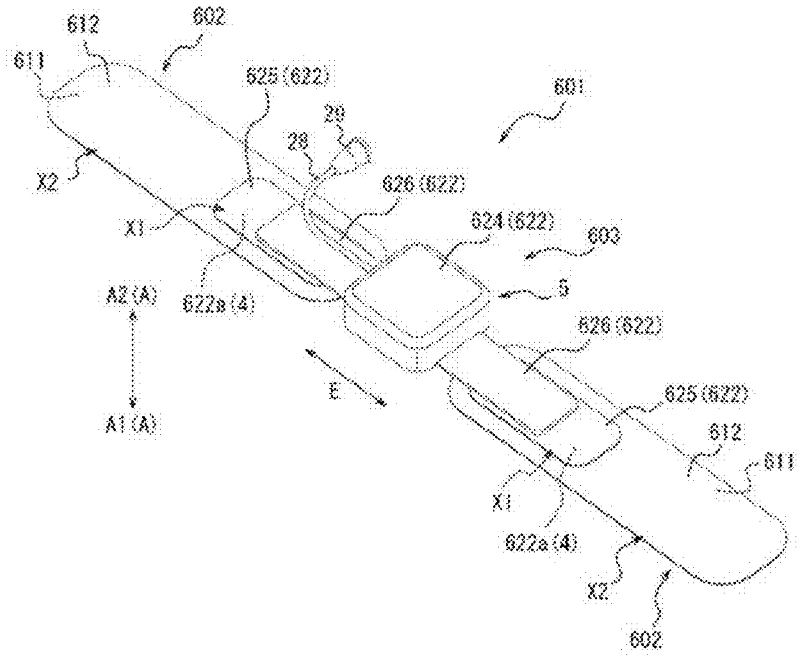
FIG. 24 is a perspective view of a compression device as one embodiment.
Figure 25:
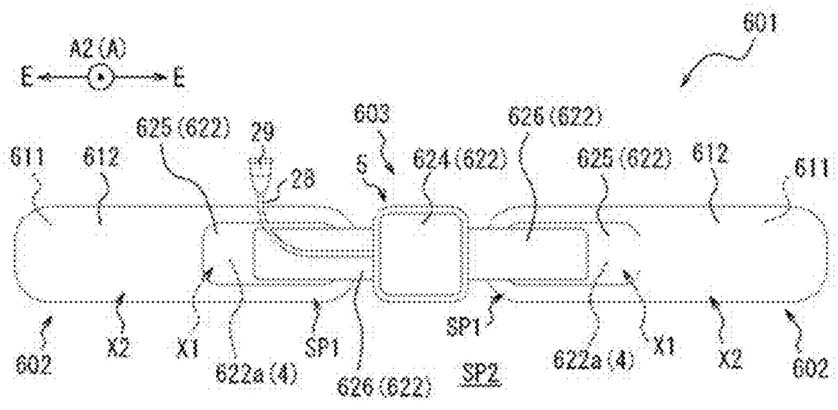
FIG. 25 is a top view of the compression device illustrated in FIG. 24.
Figure 26:
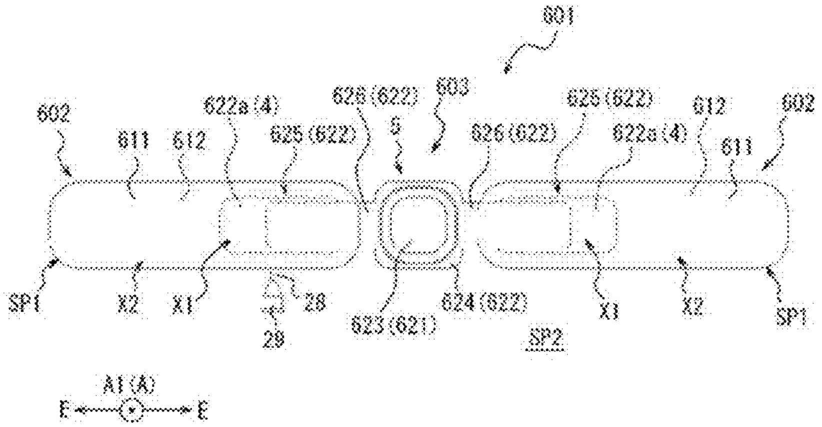
FIG. 26 is a bottom view of the compression device illustrated in FIG. 24.
Figure 27:
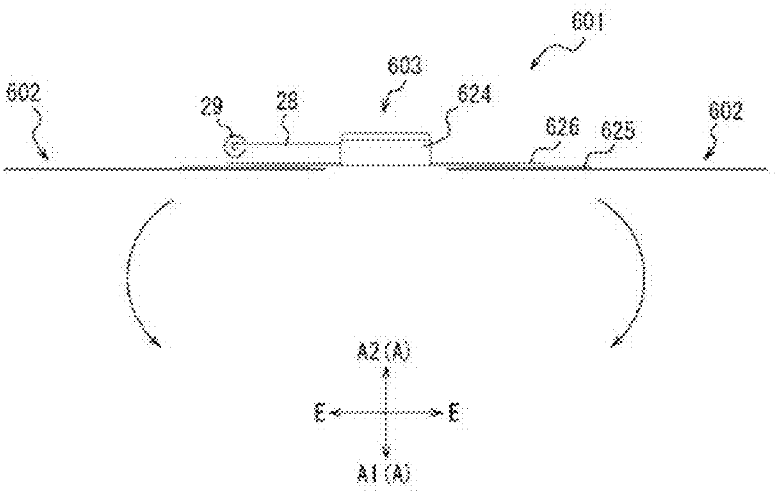
FIG. 27 is a side view of the compression device illustrated in FIG. 24.

FIG. 24 is a perspective view of the compression device 601. FIGS. 25 and 26 are plan views of the compression device 601. Specifically, FIG. 25 is a top view of the compression device 601. FIG. 26 is a bottom view of the compression device 601. FIG. 27 is a side view of the compression device 601.

The compression device 601 includes an adhesion sheet 602 and a compression member 603. The adhesion sheet 602 includes an adhesion surface 611 that adheres to a biological surface, and a mounting surface 612 that is located on an opposite side of the adhesion sheet 602 from the adhesion surface 611. In a plan view seen along the thickness direction A, the compression member 603 is disposed across the in-edge region SP1 which overlaps the adhesion sheet 602 and the out-of-edge region SP2 which does not overlap the adhesion sheet 602.

The compression member 603 includes the fixing portion 4 and the compression main body portion 5.

The adhesion sheet 602 includes the first portion X1 to which the fixing portion 4 is fixed and the second portion X2 to which the fixing portion 4 is not fixed. In the compression device 601, the second portion X2 is provided on at least a compression main body portion 5 side of the adhesion sheet 602. An adhesion portion made of an adhesive or the like is provided in the adhesion surface 611 of the adhesion sheet 602 at the position of each of the first portion X1 and the second portion X2.

In other words, in the adhesion sheet 602 of the compression device 601, the second portion X2 is provided on at least the compression main body portion 5 side with respect to the first portion X1 of the adhesion sheet 602. More specifically, in the adhesion sheet 602 of the present embodiment, the second portion X2 that continuously extends from the first portion X1 is provided on at least the compression main body portion 5 side with respect to the first portion X1 of the adhesion sheet 602.

The compression member 603 of the present embodiment includes an expander 621 that is expandable toward the downward direction A1 of the thickness direction A, and a holder 622 that holds the expander 621.

The fixing portion 4 of the present embodiment described above is formed of a contact surface 622*a* of the holder 622, the contact surface 622*a* being in contact with the adhesion sheet 602 in the in-edge region SP1. The compression main body portion 5 of the present embodiment described above includes the expander 621 and the holder 622.

The expander 621 of the present embodiment is an inflator 623 that is inflatable toward the downward direction A1 of the thickness direction A by supply of a fluid. Similar to the inflator 523 described above, the inflator 623 as the expander 621 of the present embodiment is also changed in form from a retracted form to a protruding form, and thus the inflator 623 protrudes further toward the downward direction A1 in the thickness direction A than the adhesion surface 611 of the adhesion sheet 602, to take a posture capable of compressing the biological surface.

The holder 622 of the present embodiment includes a housing portion 624 that is located in the out-of-edge region SP2 to accommodate the inflator 623 as the expander 621; a support portion 625 that is located in the in-edge region SP1 to include the contact surface 622*a*; and an arm portion 626 that connects the housing portion 624 and the support portion 625.

In the compression device 601 of the present embodiment, the shape of the adhesion sheet, the shape of the support portion of the compression member, and the shape of the arm portion of the compression member differ in comparison to the compression device 501 (refer to FIG. 21 and the like) described above.

Specifically, the support portion 625 of the present embodiment is formed in a rectangular sheet shape extending in the direction orthogonal to the thickness direction A. In addition, the support portion 625 of the present embodiment is flexible and deformable in the thickness direction A.

Similar to the support portion 625, the arm portion 626 of the present embodiment is formed in a rectangular sheet shape extending in the direction orthogonal to the thickness direction A. In addition, the arm portion 626 of the present embodiment is flexible and deformable in the thickness direction A. Furthermore, the arm portion 626 of the present embodiment is connected to a surface on the upward direction A2 side of the support portion 625 in a state where the arm portion 626 overlaps the upward direction A2 side of the support portion 625. In other words, the support portion 625 and the arm portion 626 of the present embodiment are connected in a laminated state in the thickness direction A.

The contact surface 622*a* of the present embodiment is formed of the entire region of a lower surface of the support portion 625 having a sheet shape. In such a manner, similar to the support portion 525 (refer to FIG. 22 and the like) of the compression device 501 described above, in a plan view (refer to FIG. 25 and the like), the support portion 625 of the present embodiment is not formed in an annular shape, and one support portion 625 is provided on each of both sides with the housing portion 624 interposed between the support portions 625. In other words, in the present embodiment, the housing portion 624 and two support portions 625 are linearly arranged in a plan view (refer to FIG. 25 and the like).

In addition, the adhesion sheet 602 of the present embodiment is disposed on a lower surface side of each of the support portions 625. Specifically, each of the adhesion sheets 602 has a rectangular outer edge, and includes the first portion X1 which is in contact with and fixed to the lower surface of each of the support portions 625, and the second portion X2 which extends from the first portion X1.

More specifically, in a plan view (refer to FIG. 25 and the like), the adhesion sheet 602 having a rectangular shape of the present embodiment has a longitudinal direction along a linear direction E where the housing portion 624 and the two support portions 625 are arranged. In addition, in the second portion X2 of the adhesion sheet 602 of the present embodiment, the maximum length in the linear direction E of a portion that extends to a housing portion 624 side with respect to the first portion X1 is shorter than the maximum length in the linear direction E of a portion that extends opposite to the housing portion 624 side with respect to the first portion X1. Namely, the second portion X2 of the adhesion sheet 602 of the present embodiment extends lengthways opposite to the housing portion 624 side. With such a configuration, the adhesion sheet 602 can adhere to a biological surface of, for example, the leg, the arm, the neck, the chest, or the like in a bending (curving or arcuate) manner (refer to arrows in FIG. 27).

As illustrated in FIG. 25, in a plan view, a part of the arm portion 626 of the present embodiment overlaps the adhesion sheet 602, namely, is located in the in-edge region SP1, but the arm portion 626 is not fixed to the adhesion sheet 602. In the present embodiment, since the support portion 625 is interposed between the arm portion 626 and the adhesion sheet 602, both are separated from each other in the thickness direction A, and as long as both are not fixed to each other, both may be configured to be in contact with each other.

Eighth Embodiment

Next, a compression device 701 as an eighth embodiment will be described with reference to FIGS. 28 and 29. The following description will mainly focus on the point of difference relative to the compression device 601 (refer to FIG. 24 and the like), and features that are the same or similar to those described above are identified by the same reference numerals and a detailed description of such features is not repeated.

Figure 28:
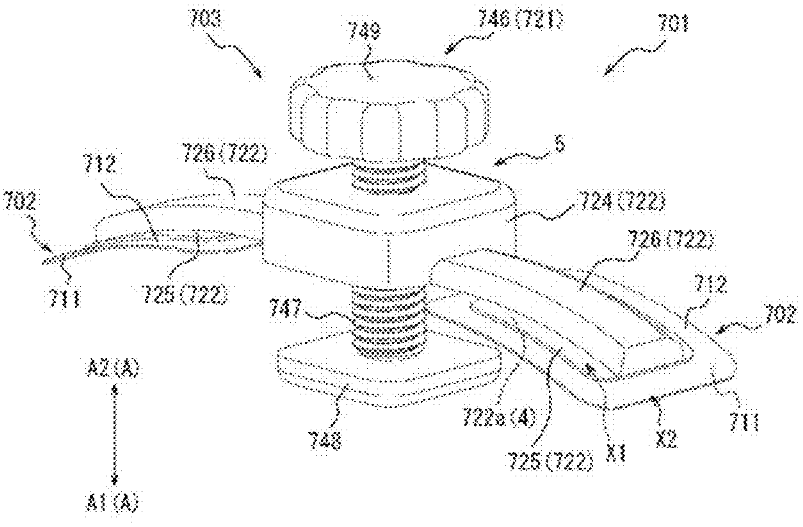
FIG. 28 is a perspective view of a compression device as one embodiment.
Figure 29:
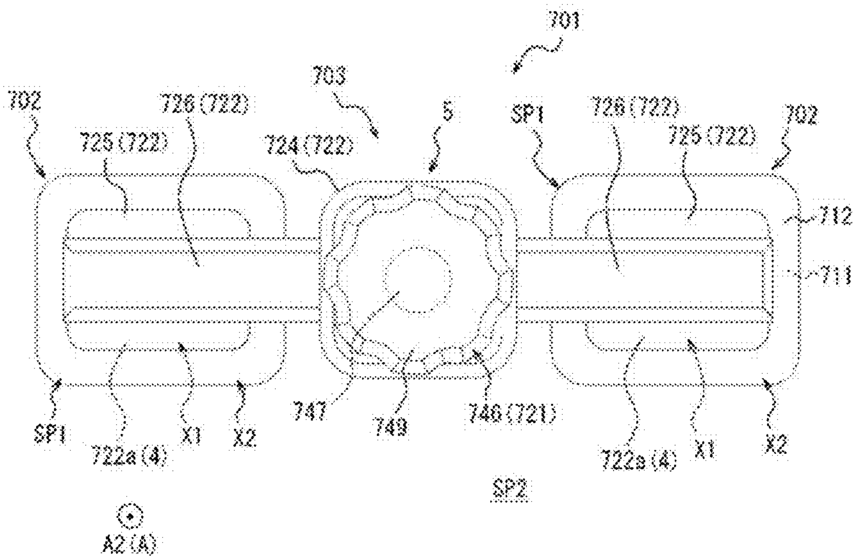
FIG. 29 is a top view of the compression device illustrated in FIG. 28.

FIG. 28 is a perspective view of the compression device 701. FIG. 29 is a plan view of the compression device 701, more specifically, a top view.

The compression device 701 includes an adhesion sheet 702 and a compression member 703. The adhesion sheet 702 includes an adhesion surface 711 that adheres to a biological surface, and a mounting surface 712 that is located on an opposite side of the adhesion sheet 702 from the adhesion surface 711. In a plan view seen along the thickness direction A, the compression member 703 is disposed across the in-edge region SP1 which overlaps the adhesion sheet 702 and the out-of-edge region SP2 which does not overlap the adhesion sheet 702.

The compression member 703 includes the fixing portion 4 and the compression main body portion 5.

The adhesion sheet 702 includes the first portion X1 to which the fixing portion 4 is fixed and the second portion X2 to which the fixing portion 4 is not fixed. In the compression device 701, the second portion X2 is provided on at least a compression main body portion 5 side of the adhesion sheet 702. An adhesion portion made of an adhesive or the like is provided in the adhesion surface 711 of the adhesion sheet 702 at the position of each of the first portion X1 and the second portion X2.

In other words, in the adhesion sheet 702 of the compression device 701, the second portion X2 is provided on at least the compression main body portion 5 side with respect to the first portion X1 of the adhesion sheet 702. More specifically, in the adhesion sheet 702 of the present embodiment, the second portion X2 that continuously extends from the first portion X1 is provided on at least the compression main body portion 5 side with respect to the first portion X1 of the adhesion sheet 702.

The compression member 703 of the present embodiment includes an expander 721 that is expandable toward the downward direction A1 of the thickness direction A, and a holder 722 that holds the expander 721.

The fixing portion 4 of the present embodiment described above is formed of a contact surface 722*a* of the holder 722, the contact surface 722*a* being in contact with the adhesion sheet 702 in the in-edge region SP1. The compression main body portion 5 of the present embodiment described above includes the expander 721 and the holder 722.

The holder 722 of the present embodiment includes a housing portion 724 that is located in the out-of-edge region SP2 to accommodate the expander 721; a support portion 725 that is located in the in-edge region SP1 to include the contact surface 722*a*; and an arm portion 726 that connects the housing portion 724 and the support portion 725.

In the compression device 701 of the present embodiment, the configuration of the expander of the compression member differs in comparison to the compression device 601 (refer to FIG. 24 and the like) described above.

The expander 721 of the present embodiment is formed of a moving body 746 that is movable with respect to the holder 722 in the thickness direction A. Specifically, the moving body 746 of the present embodiment includes a moving main body portion 747 which has a bar shape, and on an outer surface of which a male thread is formed; a pressing portion 748 which has a plate shape and is fixed to one end on the downward direction A1 of the moving main body portion 747 to press the biological surface; and an operation portion 749 that is fixed to one end on the upward direction A2 of the moving main body portion 747.

The moving main body portion 747 is movable in the thickness direction A by the holder 722. A through-hole that penetrates through the holder 722 in the thickness direction A is formed in the holder 722 of the present embodiment. A female thread is provided on an inner surface of the through-hole. The male thread on the outer surface of the moving main body portion 747 is screwed with or threadably engaged with the female thread of the through-hole of the holder 722, so that the moving main body portion 747 is held by the holder 722. The moving main body portion 747 is held by the holder 722 in a state where the moving main body portion 747 protrudes from the through-hole of the holder 722 toward both sides of the thickness direction A.

The pressing portion 748 protrudes outward in a radial direction from the one end on the downward direction A1 of the moving main body portion 747. The pressing portion 748 is movable in the thickness direction A by rotating the moving main body portion 747 around an axis (central or rotation axis of the moving main body portion 747). Specifically, when the biological surface is to be pressed by the pressing portion 748, the pressing portion 748 is moved in the downward direction A1. On the contrary, when the pressing portion 748 is to be separated from the biological surface, the pressing portion 748 is moved in the upward direction A2.

The moving main body portion 747 is rotatable around the axis by gripping and rotating the operation portion 749.

In such a manner, the expander 721 is not limited to the inflator 623 (refer to FIG. 26) described above, and may be configured to be mechanically expandable.

Ninth Embodiment

Figure 31:
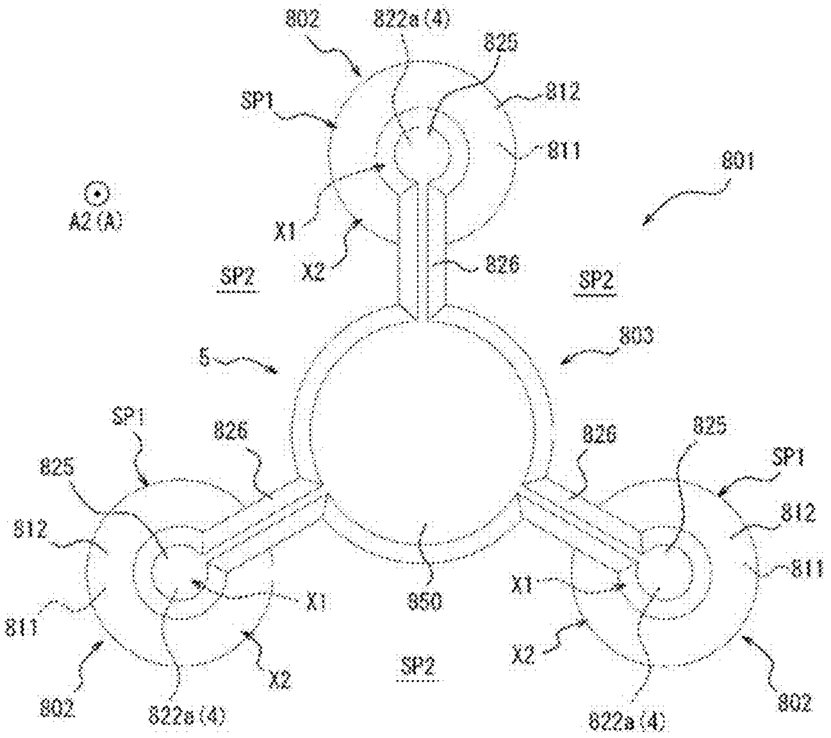
FIG. 31 is a top view of the compression device illustrated in FIG. 30.
Figure 32:
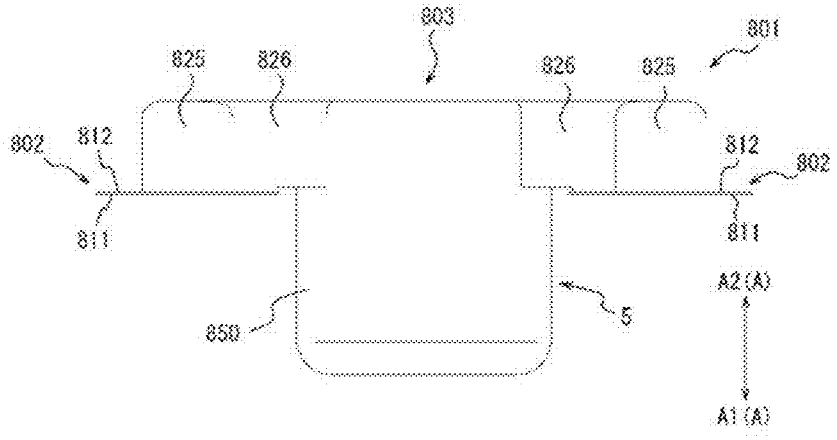
FIG. 32 is a side view of the compression device illustrated in FIG. 30.

Next, a compression device 801 as a ninth embodiment will be described with reference to FIGS. 30 to 32. The following description will mainly focus on the point of difference relative to the compression device 501 (refer to FIG. 21 and the like), and features that are the same or similar to those described above are identified by the same reference numerals and a detailed description of such features is not repeated.

Figure 30:
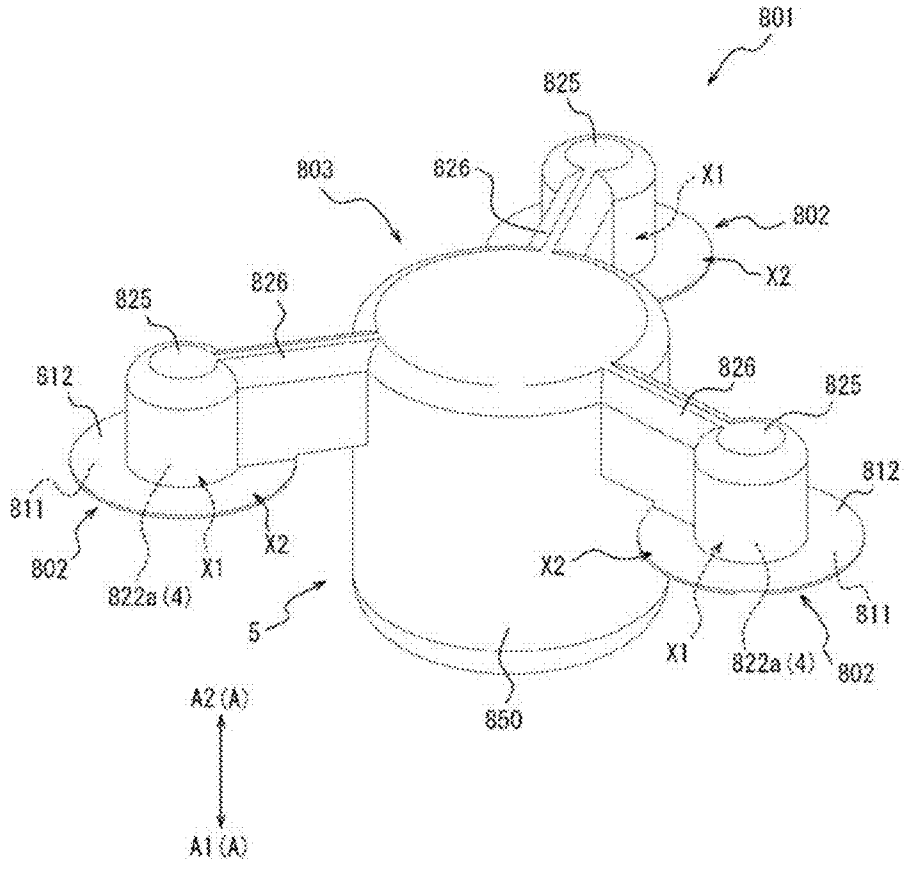
FIG. 30 is a perspective view of a compression device as one embodiment.

FIG. 30 is a perspective view of the compression device 801. FIG. 31 is a plan view of the compression device 801, more specifically, a top view. FIG. 32 is a side view of the compression device 801.

The compression device 801 includes the adhesion sheet 802 and a compression member 803. The adhesion sheet 802 includes the adhesion surface 811 that adheres to a biological surface, and a mounting surface 812 that is located on an opposite side of the adhesion sheet 802 from the adhesion surface 811. In a plan view (refer to FIG. 31) seen along the thickness direction A, the compression member 803 is disposed across the in-edge region SP1 which overlaps the adhesion sheet 802 and the out-of-edge region SP2 which does not overlap the adhesion sheet 802.

The compression member 803 includes the fixing portion 4 and the compression main body portion 5.

The adhesion sheet 802 includes the first portion X1 to which the fixing portion 4 is fixed and the second portion X2 to which the fixing portion 4 is not fixed. In the compression device 801, the second portion X2 is provided on at least a compression main body portion 5 side of the adhesion sheet 802. An adhesion portion made of an adhesive or the like is provided in the adhesion surface 811 of the adhesion sheet 802 at the position of each of the first portion X1 and the second portion X2.

In other words, in the adhesion sheet 802 of the compression device 801, the second portion X2 is provided on at least the compression main body portion 5 side with respect to the first portion X1 of the adhesion sheet 802. More specifically, in the adhesion sheet 802 of the present embodiment, the second portion X2 that continuously extends from the first portion X1 is provided on at least the compression main body portion 5 side with respect to the first portion X1 of the adhesion sheet 802.

The fixing portion 4 of the present embodiment described above is formed of a contact surface 822*a* of the compression member 803, the contact surface 822*a* being in contact with the adhesion sheet 802 in the in-edge region SP1. In addition, as will be described in detail later, the compression main body portion 5 of the present embodiment is formed of a portion of the compression member 803, the portion protruding further in the downward direction A1 than the adhesion sheet 802 in the out-of-edge region SP2.

In the compression device 801 of the present embodiment, the configuration of the compression member and the number of the adhesion sheets differ in comparison to the compression device 501 (refer to FIG. 21 and the like) described above.

The compression member 803 of the present embodiment does not include an expander and is not configured to extend in the thickness direction A. Namely, the compression member 803 of the present embodiment includes a pressing portion 850 as the compression main body portion 5 which has a columnar shape and extends from a mounting surface 812 side of the adhesion sheet 802 to an adhesion surface 811 side in the thickness direction A in the out-of-edge region SP2; a support portion 825 which is located in the in-edge region SP1 to include the contact surface 822*a*; and an arm portion 826 which connects the pressing portion 850 and the support portion 825.

The number of the support portions 825 and the arm portions 826 of the present embodiment which are provided differs relative to the support portions 525 and the arm portions 526 shown in FIG. 21, but the shape of each of the support portion 825 and the arm portion 826 is the same in comparison to the support portion 525 (refer to FIG. 21 and the like) and the arm portion 526 (refer to FIG. 21 and the like) of the compression device 501 (refer to FIG. 21 and the like) described above.

Since the pressing portion 850 of the present embodiment protrudes further in the downward direction A1 than the adhesion surface 811 of the adhesion sheet 802, when the adhesion sheet 802 adheres to the biological surface, the pressing portion 850 presses the biological surface. In such a manner, the compression member 803 that does not include an expander may be adopted.

The compression member 803 of the present embodiment can be integrally molded. Examples of the material of the compression member 803 of the present embodiment include a resin material. As the resin material, the same material as the material of the holder 22 (refer to FIG. 1 and the like) described above can be used.

The compression device and the compression method according to the present disclosure are not limited to the specific configurations and steps described in the above embodiments, and various modifications and changes can be made without departing from the concept of the present disclosure. For example, also a compression device that is configured by appropriately combining the components illustrated in the above-described first to ninth embodiments belongs to the technical scope of the present disclosure.

In the above-described embodiments, the adhesion sheet is provided as one example of the mounting member that is mountable on a biological surface; however, the mounting member is not limited to the adhesion sheet, and examples of the mounting member include a band member (band) made of resin, or the like. The band member as a mounting member includes, for example, a latch portion such as a surface fastener. For this reason, the band member as a mounting member can be wound around and fixed to the arm or leg by the latch portion. The latch portion is not limited to the surface fastener and may include, for example, a claw portion and a fastening portion on which the claw portion is caught.

In addition, in the compression device according to the present disclosure, a receiving opening portion that can receive a medical device 100 (refer to FIGS. 6A to 6G and the like) such as a catheter and a sheath may be formed in at least one of the mounting member and the compression member.

Specifically, in the compression device 1 illustrated in FIGS. 1 to 6G, a receiving opening portion 1000 is formed by the adhesion sheet 2 as a mounting member and the compression member 3. The receiving opening portion 1000 of the compression device 1 illustrated in FIGS. 1 to 6G is formed of an opening region including a part of the central opening region defined by the adhesion sheet 2. More specifically, the receiving opening portion 1000 of the compression device 1 illustrated in FIGS. 1 to 6G is formed of (1) the slit 15 of the adhesion sheet 2, (2) the gap 25*a* formed by the support portion 25 of the compression member 3, and (3) a part of the central opening region defined by both the adhesion sheet 2 and the support portion 25 of the compression member 3.

Furthermore, the receiving opening portion 1000 of the compression device 1 illustrated in FIGS. 1 to 6G is defined by not the expander 21 but the holder 22 of the compression member 3. More specifically, the receiving opening portion 1000 of the compression device 1 illustrated in FIGS. 1 to 6G is defined by the support portion 25 of the holder 22 of the compression member 3. Namely, the receiving opening portion 1000 of the compression device 1 illustrated in FIGS. 1 to 6G is formed by the adhesion sheet 2 as a mounting member and the holder 22 of the compression member 3.

Figure 8:
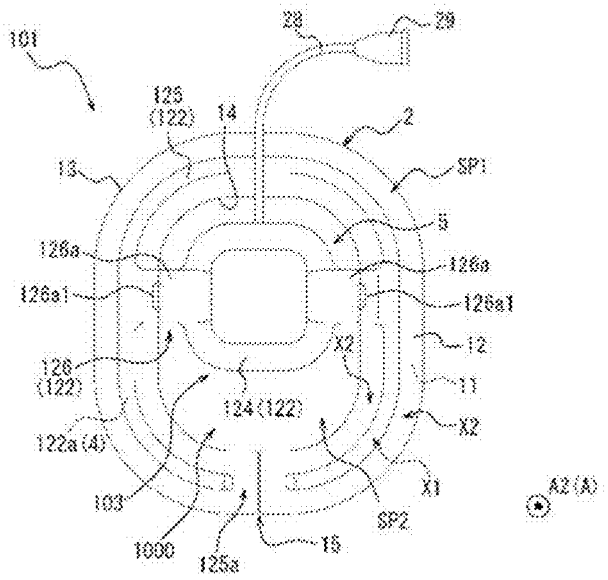
FIG. 8 is a top view of the compression device illustrated in FIG. 7.

In the compression device 101 illustrated in FIGS. 7 to 9, the receiving opening portion 1000 is formed by the adhesion sheet 2 as a mounting member and the compression member 103. The receiving opening portion 1000 of the compression device 101 illustrated in FIGS. 7 to 9 is formed of an opening region including a part of the central opening region defined by the adhesion sheet 2. More specifically, the receiving opening portion 1000 of the compression device 101 illustrated in FIGS. 7 to 9 is formed of (1) the slit 15 of the adhesion sheet 2, (2) a gap 125*a* formed by the support portion 125 of the compression member 103, and (3) a part of the central opening region defined by both the adhesion sheet 2 and the support portion 125 of the compression member 103.

Furthermore, the receiving opening portion 1000 of the compression device 101 illustrated in FIGS. 7 to 9 is defined by not the expander 121 but the holder 122 of the compression member 103. More specifically, the receiving opening portion 1000 of the compression device 101 illustrated in FIGS. 7 to 9 is defined by the support portion 125 of the holder 122 of the compression member 103. Namely, the receiving opening portion 1000 of the compression device 101 illustrated in FIGS. 7 to 9 is formed by the adhesion sheet 2 as a mounting member and the holder 122 of the compression member 103.

In the compression device 201 illustrated in FIGS. 10 to 13B, the receiving opening portion 1000 is formed by the adhesion sheet 2 as a mounting member and the compression member 203. The receiving opening portion 1000 of the compression device 201 illustrated in FIGS. 10 to 13B is formed of an opening region including a part of the central opening region defined by the adhesion sheet 2. More specifically, the receiving opening portion 1000 of the compression device 201 illustrated in FIGS. 10 to 13B is formed of (1) the slit 15 of the adhesion sheet 2, (2) a gap 225*a* formed by the support portion 225 of the compression member 203, and (3) a part of the central opening region defined by both the adhesion sheet 2 and the support portion 225 of the compression member 203.

Furthermore, the receiving opening portion 1000 of the compression device 201 illustrated in FIGS. 10 to 13B is defined by not the expander 221 but the holder 222 of the compression member 203. More specifically, the receiving opening portion 1000 of the compression device 201 illustrated in FIGS. 10 to 13B is defined by the support portion 225 of the holder 222 of the compression member 203. Namely, the receiving opening portion 1000 of the compression device 201 illustrated in FIGS. 10 to 13B is formed by the adhesion sheet 2 as a mounting member and the holder 222 of the compression member 203.

In the compression device 301 illustrated in FIGS. 14 to 17, the receiving opening portion 1000 is formed by the adhesion sheet 302 as a mounting member and the compression member 303. The receiving opening portion 1000 of the compression device 301 illustrated in FIGS. 14 to 17 is formed of an opening region including a part of the central opening region defined by the adhesion sheet 302. More specifically, the receiving opening portion 1000 of the compression device 301 illustrated in FIGS. 14 to 17 is formed of (1) a slit 315 of the adhesion sheet 302, (2) a gap 325*a* formed by the support portion 325 of the compression member 303, and (3) a part of the central opening region defined by both the adhesion sheet 302 and the support portion 325 of the compression member 303.

Furthermore, the receiving opening portion 1000 of the compression device 301 illustrated in FIGS. 14 to 17 is defined by not the expander 321 but the holder 322 of the compression member 303. More specifically, the receiving opening portion 1000 of the compression device 301 illustrated in FIGS. 14 to 17 is defined by the support portion 325 of the holder 322 of the compression member 303. Namely, the receiving opening portion 1000 of the compression device 301 illustrated in FIGS. 14 to 17 is formed by the adhesion sheet 302 as a mounting member and the holder 322 of the compression member 303.

Also in the compression device 401 illustrated in FIGS. 18 to 20, for example, a gap may be provided in a part of the support portion 425 to form a receiving opening portion.

Figure 36:
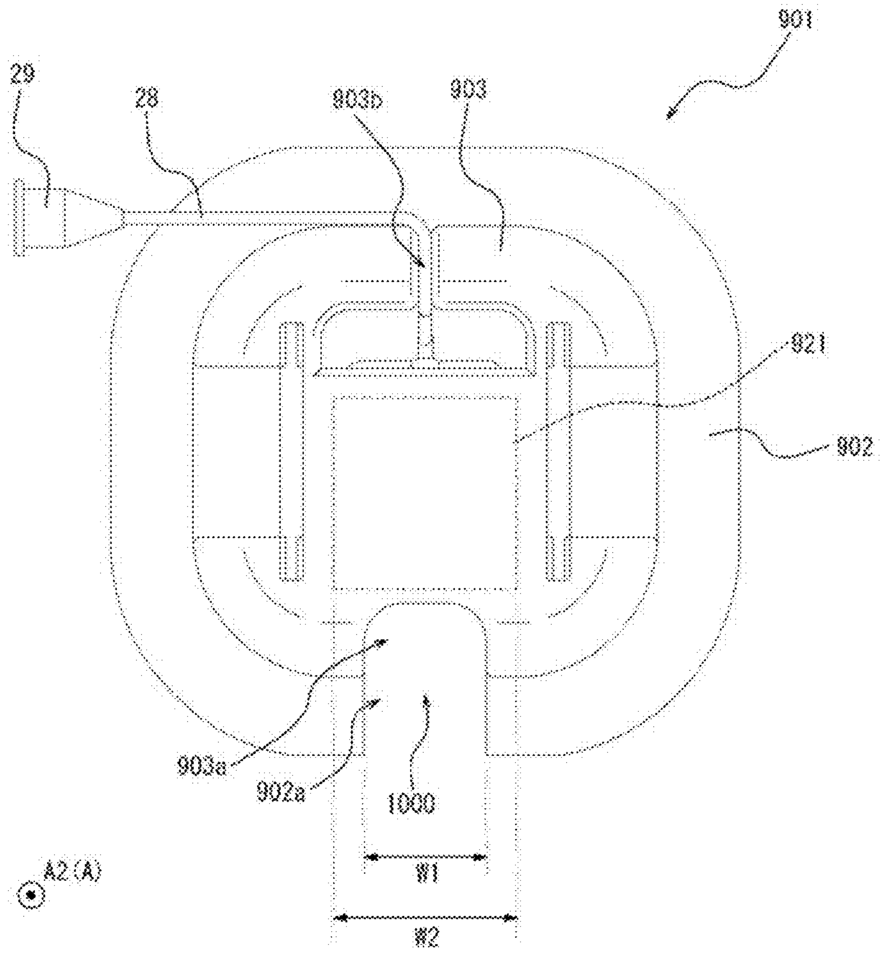
FIG. 36 is a top view of a compression device as one embodiment.

In addition, FIG. 36 is a top view of a compression device 901 as one embodiment of the present disclosure. The compression device 901 illustrated in FIG. 36 includes an adhesion sheet 902 as a mounting member and a compression member 903. As described above, in each of the compression devices 1, 101, 201, and 301 illustrated in FIGS. 1 to 17, the receiving opening portion 1000 is formed of an opening region including a part of the central opening region defined by each of the adhesion sheets 2 and 302. However, the receiving opening portion 1000 may not include the central opening region defined by the adhesion sheet. In the compression device 901 illustrated in FIG. 36, the receiving opening portion 1000 is formed of a cutout opening region formed by the adhesion sheet 902 and the compression member 903. More specifically, the receiving opening portion 1000 illustrated in FIG. 36 is a U-shaped cutout opening region that is defined by a gap 902*a* formed by the adhesion sheet 902 and a cutout portion 903*a* formed at an outer edge of the compression member 903. In such a manner, the shape of the receiving opening portion 1000 is not particularly limited, and the receiving opening portion 1000 may be configured to include the central opening region of the adhesion sheet, or may be configured to not include the central opening region of the adhesion sheet. For this reason, the receiving opening portion 1000 may be a cutout opening region that is defined by a concave cutout formed at the outer edge of the mounting member and the outer edge of the compression member.

It is preferable that the receiving opening portion 1000 is formed to be adjacent to the compression main body portion of the compression member. For this reason, it is preferable that the position of the receiving opening portion 1000 is determined according to the position of the compression main body portion. Therefore, the receiving opening portion 1000 may be formed in at least one of the mounting member and the compression member, and the present disclosure is not limited to this configuration where the receiving opening portion 1000 is formed in both the mounting member and the compression member. Namely, each the receiving opening portions 1000 illustrated in FIGS. 1 to 17 and 36 is formed by both the adhesion sheet as a mounting member and the compression member, but the invention is not limited to this configuration. The receiving opening portion 1000 may be formed only in either one of the mounting member and the compression member.

In addition, in a top view, a width W1 of the receiving opening portion 1000 illustrated in FIG. 36 is smaller than a width W2 of an inflator 923 as an expander 921. In a top view, the "width W1" and the "width W2" mean widths in a direction (rightward and leftward direction in FIG. 36) substantially orthogonal to a direction (upward and downward direction in FIG. 36) where the receiving opening portion 1000 and the expander 921 are arranged. In FIG. 36, the position of the expander 921 is indicated by a dotted line. In such a manner, after the sheath is removed, the perforation P (refer to FIG. 34B) is easily located immediately below the biological surface pressed by the expander 921. For this reason, the perforation P can be more reliably narrowed or obstructed by the expander 921.

Furthermore, in the compression device 901 illustrated in FIG. 36, similar to the compression device 101 illustrated in FIGS. 7 to 9, in a top view, the receiving opening portion 1000 is provided opposite to an expansion port with the expander 921 interposed therebetween. The expansion port in the compression device 901 illustrated in FIG. 36 means a portion of the holder 922, to which one end of the tube 28 is connected.

In addition, in the compression device 901 illustrated in FIG. 36, a part of the tube 28 is held by a slit 903*b* formed in the compression member 903. In addition, in a top view, the tube 28 is provided opposite to the receiving opening portion 1000 with the expander 921 interposed therebetween. In such a manner, the connection portion 29 is unlikely to be located in the vicinity of the receiving opening portion 1000. For this reason, when the compression device 901 is disposed on the biological surface, a trouble that the connection portion 29 hangs around to be located on the receiving opening portion 1000 to cause a disturbance can be reduced.

In addition, in the compression device 901 illustrated in FIG. 36, the compression member 903 is made of a harder material than the adhesion sheet 902 as a mounting member. In other words, the compression member 903 is less likely to be deformed and has greater rigidity than the adhesion sheet 902 as a mounting member.

As described above, since the compression device includes the receiving opening portion 1000, a health care worker that uses the compression device easily disposes the medical device 100 (refer to FIGS. 6A to 6G and the like) such as a sheath at a proper position for the compression device. For this reason, the position of the biological surface compressed by the compression device can be suppressed from deviating from the proper position to be compressed. Namely, according to the compression device, the proper position on the biological surface is easily compressed.

Specifically, since the compression device includes the receiving opening portion 1000, a portion of the sheath as the medical device 100 (refer to FIGS. 6A to 6G and the like) inserted into the living body, the portion extending outside the living body, can be disposed in the receiving opening portion 1000 (refer to FIGS. 6A and 6B). In FIGS. 6A and 6B, as one example, the sheath as the medical device 100 (refer to FIGS. 6A to 6G) is moved from outside the adhesion sheet 2 into the central opening region of the adhesion sheet 2 through the slit 15 of the adhesion sheet 2 extending in an annular shape.

In addition, the sheath as the medical device 100 can be removed outside the living body through the receiving opening portion 1000 (refer to FIGS. 6F and 6G). In FIGS. 6F and 6G, as one example, the sheath is removed outside the living body through the central opening region of the adhesion sheet 2.

After the sheath is removed, the compression member (for example, the "compression member 3" in FIGS. 6A to 6G) compresses at least one of the wound hole of the biological surface or the vicinity of the wound hole after the sheath as the medical device 100 is removed. Therefore, hemostasis can be performed by narrowing or obstructing the perforation P (refer to FIG. 34B).

Next, the compression device 201 illustrated in FIGS. 10 to 13B will be described in further detail.

As illustrated in FIG. 35, in the compression device 201 illustrated in FIGS. 10 to 13B, in a state where the adhesion sheet 2 as a mounting member is mounted on the living body, the compression main body portion 5 of the compression member 203 can compress the biological surface toward the inclination direction F inclined to a receiving opening portion 1000 side (left side in FIG. 35) in a perpendicular direction perpendicular to the biological surface BS (the same direction as the thickness direction A in FIG. 35, an upward and downward direction in FIG. 35, and hereinafter, simply referred to as a "perpendicular direction"). In such a manner, as illustrated in FIG. 35, the perforation P is easily narrowed or obstructed without obstructing the vein such as the femoral vein FV.

Specifically, the compression main body portion 5 of the compression device 201 illustrated in FIGS. 10 to 13B can protrude toward the inclination direction F rather than the above-described perpendicular direction. More specifically, in the compression device 201, the inflator 223 as the expander 221 of the compression member 203 is configured to protrude toward the inclination direction F rather than the above-described perpendicular direction.

In FIGS. 10 to 13B, the compression main body portion 5 includes the expander 221 and the holder 222, but the invention is not limited to this configuration. For example, the compression main body portion 5 may be configured to protrude toward the inclination direction F at all times rather than the above-described perpendicular direction.

Figure 37:
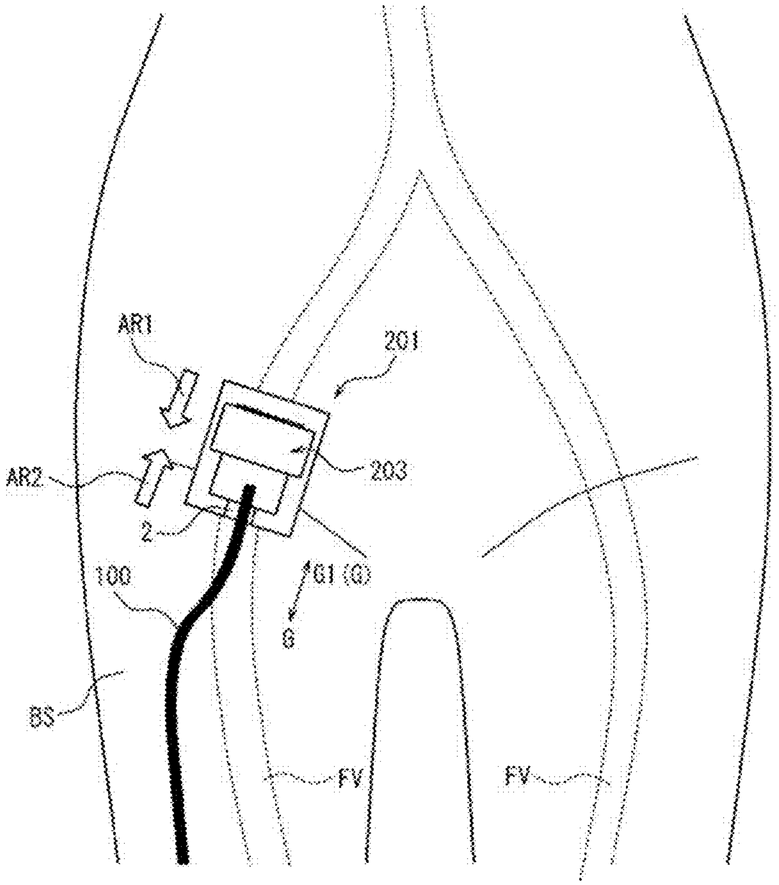
FIG. 37 is a front view of the state illustrated in FIG. 35 as seen from a biological surface side.

FIG. 37 is a front view of the state illustrated in FIG. 35 as seen from a biological surface BS side. In other words, FIG. 37 illustrates a front view at a position on the biological surface BS, which is compressed by the compression device 201. Here, the expression "a front view at a position on the biological surface, which is compressed by the compression device" means a state where a portion of the biological surface, which is to be compressed by the compression device, is seen from a direction perpendicular to the portion before compression. FIG. 37 illustrates a front view of the inguinal region. In the front view illustrated in FIG. 37, a direction where the biological surface BS is compressed (refer to white arrow "AR1" in FIG. 37) is opposite to an insertion direction G1 of the sheath from the biological surface BS toward the vein (refer to white arrow "AR2" in FIG. 37) in an extending direction G of the perforation P. Namely, in the front view illustrated in FIG. 37, the direction where the compression device 201 compresses the biological surface BS is opposite to the insertion direction G1 of the sheath. In such a manner, the perforation P (refer to FIG. 35) is easily narrowed or obstructed without obstructing the vein such as the femoral vein FV.

In other words, as illustrated in FIG. 35, the extending direction G of the perforation P is inclined with respect to the biological surface BS, and is inclined also with respect to the perpendicular direction (upward and downward direction in FIG. 35) perpendicular to the biological surface BS. In addition, as illustrated in FIG. 35, since the compression main body portion 5 protrudes toward the inclination direction F, the direction of compression of the biological surface BS by compression device 201 is inclined with respect to the biological surface BS, and is inclined also with respect to the perpendicular direction (upward and downward direction in FIG. 35) perpendicular to the biological surface BS. Furthermore, as illustrated in FIG. 35, the extending direction G of the perforation P is inclined reverse to the inclination direction F, which is the direction of compression of the biological surface by the compression device 201, with respect to the above perpendicular direction (upward and downward direction in FIG. 35). Namely, the compression of the biological surface by the compression device 201 is executed such that the direction of compression intersects the extending direction G of the perforation P. Therefore, the perforation P can be efficiently narrowed or obstructed.

Figure 38:
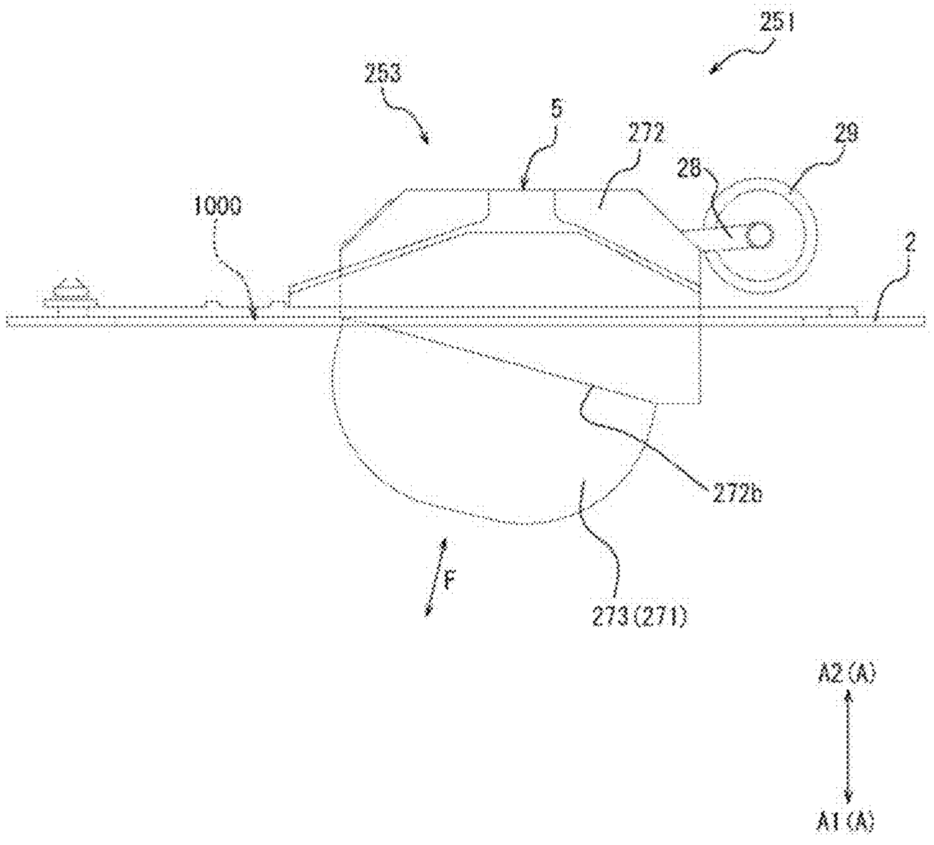
FIG. 38 is a side view of a compression device as one modification example of the compression device illustrated in FIG. 10.

Next, a compression device 251 as a modification example of the compression device 201 illustrated in FIGS. 10 to 13B will be described with reference to FIG. 38. FIG. 38 is a side view of the compression device 251. The compression device 251 illustrated in FIG. 38 includes the adhesion sheet 2 as a mounting member and a compression member 253. The compression member 253 includes an inflator 273 as an expander 271 and a holder 272 that holds the inflator 273.

In the compression device 251 illustrated in FIG. 38, the inflator 273 is held by a holding flat surface 272*b* of the holder 272. In addition, the inflator 273 is inflatable to protrude in a direction perpendicular to the holding flat surface 272*b*. Here, in the compression device 251 illustrated in FIG. 38, the holding flat surface 272*b* of the holder 272 extends obliquely with respect to the thickness direction A. For this reason, in the compression device 251 illustrated in FIG. 38, in a state where the adhesion sheet 2 as a mounting member is mounted on the living body, the compression main body portion 5 of the compression member 253 can compress the biological surface toward the inclination direction F that is inclined to a receiving opening portion 1000 side (left side in FIG. 38) with respect to a perpendicular direction perpendicular to the biological surface (the same direction as the thickness direction A in FIG. 38).

Specifically, the compression main body portion 5 of the compression device 251 illustrated in FIG. 38 can protrude toward the inclination direction F rather than the above-described perpendicular direction. More specifically, in the compression device 251, the inflator 273 as the expander 271 of the compression member 253 is configured to protrude toward the inclination direction F rather than the above-described perpendicular direction.

As described above, according to the compression device 201 illustrated in FIGS. 10 to 13B and the compression device 251 illustrated in FIG. 38, the compression main body portion 5 compresses the biological surface toward the inclination direction F that is inclined with respect to the direction perpendicular to the biological surface. For this reason, in comparison to when the compression main body portion 5 compresses the biological surface toward the direction perpendicular to the biological surface, the perforation P (refer to FIG. 34B and the like) can be efficiently narrowed or obstructed by a smaller pressing force.

The detailed description above describes embodiments of a compression device and a compression method representing examples of the inventive compression device and compression method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A compression device comprising:

an adhesion sheet including an adhesion surface that is adherable to a biological surface, the adhesion sheet possessing a thickness, the thickness of the adhesion sheet extending in a thickness direction of the adhesion sheet between one side of the adhesion sheet and an other side of the adhesion sheet that face in opposite directions, the adhesion surface being on the one side of the adhesion sheet in the thickness direction; and a compression member mounted on the adhesion sheet and configured to compress the biological surface when the adhesion surface of the adhesion sheet is adhered to the biological surface;

the compression member comprising:

a fixing portion fixed to the adhesion sheet on the other side of the adhesion sheet in the thickness direction;

an expandable expander configured to compress the biological surface when the adhesion surface of the adhesion sheet is adhered to the biological surface, the expandable expander positioned to not overlap the adhesion sheet in a plan view of the compression device, the expandable expander including a part that is configured to protrude further toward the one side of the adhesion sheet in the thickness direction than the adhesion surface of the adhesion sheet;

a housing portion that accommodates the part of the expandable expander that is configured to protrude further toward the one side of the adhesion sheet in the thickness direction than the adhesion surface of the adhesion sheet, the housing portion being located so that the housing portion does not overlap the adhesion sheet in the plan view;

a support portion located in overlapping relation to the adhesion sheet in the plan view, the support portion being fixed to the adhesive sheet on the other side of the adhesive sheet in the thickness direction; and an arm portion that connects the housing portion and the support portion, and the housing portion and the arm portion collectively constituting a first member that is configured to be disassembled from the support portion and that is configured to be connected to the support portion after being disassembled from the support portion.

2. The compression device according to claim 1, wherein the arm portion that connects the housing portion and the support portion includes a movable portion that is movable relative to the housing portion in one direction approaching the housing portion and in an opposite direction away from the housing portion.

3. The compression device according to claim 1, wherein the arm portion is a first arm portion that projects away from the housing portion in a first direction, and further comprising a second arm portion that projects away from the housing portion in a second direction opposite the first direction.

4. The compression device according to claim 1, wherein the first member that is configured to be disassembled from the support portion and that is configured to be connected to the support portion after being disassembled from the support portion comprises a projecting portion that is positioned in a recessed portion to connect the first member to the support portion and is removable from the recessed portion to disassemble the first member from the support portion, one of the projecting portion and the recessed portion being provided on the arm portion and the other of the projecting portion and the recessed portion being fixed to the support portion.

5. The compression device according to claim 4, wherein the arm portion that connects the housing portion and the support portion includes a movable part that is movable relative to the housing portion in one direction approaching the housing portion and in an opposite direction away from the housing portion, the projecting portion being provided on the movable portion of the arm portion so that the projecting portion moves together with the movable portion, the recessed portion being fixed to the support portion.

6. The compression device according to claim 1, wherein the arm portion that connects the housing portion and the support portion includes a movable portion and a tubular portion that axially overlap one another, the movable portion being movable relative to the tubular portion both toward and away from the housing portion, the first member that is configured to be disassembled from the support portion and that is configured to be connected to the support portion after being disassembled from the support portion comprising a projecting portion projecting from the movable portion and being positioned in a recessed portion to connect the first member to the support portion, the projecting portion being removable from the recessed portion and the movable portion being movable toward the housing to disassemble the first member from the support portion.

7. The compression device according to claim 6, wherein the arm portion is a first arm portion that projects away from the housing portion in a first direction, and further comprising a second arm portion that projects away from the housing portion in a second direction opposite the first direction, the movable portion of the first arm portion being a first movable portion, the tubular portion of the first arm portion being a first tubular portion, the projecting portion being a first projecting portion, the recessed portion being a first recessed portion, the second arm portion including a second movable portion and a second tubular portion that axially overlap one another, the second movable portion being movable relative to the second tubular portion both toward and away from the housing portion, the movable portion including a second projecting portion that projects from the second movable portion and that is positioned in a second recessed portion to connect the second arm portion to the support portion.

8. The compression device according to claim 1, wherein the part of the expandable expander has an interior in fluid communication with a tube that projects away from the arm portion.

9. The compression device according to claim 1, wherein the housing portion comprising a recessed accommodation portion in which is accommodated the part of the expandable expander.

10. A compression device comprising:

an adhesion sheet possessing a thickness extending in a thickness direction of the adhesion sheet between a first side of the adhesion sheet and an opposite second side of the adhesion sheet, the adhesion sheet including an adhesion surface on the first side of the adhesion sheet to contact a biological surface and adhere the compression device to the biological surface;

the adhesion sheet being an annular-shaped adhesion sheet as seen in a plan view, the annular-shaped adhesion sheet having, as seen in the plan view, an inner periphery surrounding a region that is devoid of the adhesion sheet;

an upstanding support portion fixed to the annular-shaped adhesion sheet on the second side of the annular-shaped adhesion sheet;

a holder;

an expandable expander configured to compress the biological surface when the adhesion surface of the annular-shaped adhesion sheet is adhered to the biological surface, the expandable expander being mounted on the holder so that the expandable expander is positioned, as seen in the plan view, in the region that is surrounded by the inner periphery of the annular-shaped adhesion sheet and that is devoid of the adhesion sheet, the expandable expander being configured to protrude further toward the first side of the adhesion sheet in the thickness direction than the adhesion surface of the adhesion sheet; and an arm portion that removably connects the holder and the expandable expander to the support portion so that the holder and the expandable expander are disassemblable from the support portion.

11. The compression device according to claim 10, wherein the arm portion that removably connects the holder and the expandable expander to the support portion includes a movable portion that is movable relative to the holder in one direction approaching the holder and in an opposite direction away from the holder.

12. The compression device according to claim 11, wherein the arm portion that removably connects the holder and the expandable expander to the support portion also includes a protruding portion fixed to the holder and protruding away from the holder, the movable portion being movably mounted on the protruding portion to move along the protruding portion.

13. The compression device according to claim 12, wherein the protruding portion is a tubular portion, and a part of the movable portion being positioned in the tubular portion.

14. The compression device according to claim 11, wherein the movable portion includes a projecting portion that is fixed to the movable portion so that movement of the movable portion results in movement of the projecting portion, the projecting portion being removably positioned in a recessed portion that is fixed to the upstanding support portion so that the projecting portion is separable from the upstanding support portion to allow the holder and the expandable expander to be disassembled from the support portion.

15. The compression device according to claim 11, wherein the movable portion includes two projecting portions that are fixed to the movable portion so that movement of the movable portion results in movement of the two projecting portions, the two projecting portions being removably positioned in respective recessed portions that are fixed to the upstanding support portion so that the two projecting portions are separable from the upstanding support portion to allow the holder and the expandable expander to be disassembled from the support portion.

16. The compression device according to claim 10, wherein the arm portion that removably connects the holder and the expandable expander to the support portion is a first arm portion, and further comprising a second arm portion that removably connects the holder and the expandable expander to the support portion, the first arm portion extending from a first part of the upstanding support portion to a first part of the holder, the second arm portion extending from a second part of the upstanding support portion to a second part of the holder, the first part of the upstanding support portion being spaced apart from the second part of the upstanding support portion, the first part of the holder being spaced apart from the second part of the holder.

17. The compression device according to claim 10, wherein the holder comprises a recessed accommodation portion in which is accommodated the expandable expander.

18. A compression device comprising:

an adhesion sheet possessing a thickness extending in a thickness direction of the adhesion sheet between a first side of the adhesion sheet and an opposite second side of the adhesion sheet, the adhesion sheet including an adhesion surface on the first side of the adhesion sheet to contact a biological surface and adhere the compression device to the biological surface;

the adhesion sheet being an annular-shaped adhesion sheet as seen in a plan view, the annular-shaped adhesion sheet having, as seen in the plan view, an inner periphery surrounding a region that is devoid of the adhesion sheet;

an upstanding support portion fixed to the annular-shaped adhesion sheet on the second side of the annular-shaped adhesion sheet;

a holder;

an expandable expander mounted on the holder;

an arm portion configured to removably connect the holder to the upstanding support portion so that: i) the expandable expander mounted on the holder is positioned, as seen in the plan view, in the region that is surrounded by the inner periphery of the annular-shaped adhesion sheet and that is devoid of the adhesion sheet; and ii) the arm portion when connected to the support portion is separable from the support portion to disassemble the holder and the expandable expander from the support portion; and the expandable expander being configured to protrude further toward the first side of the adhesion sheet in the thickness direction than the adhesion surface of the adhesion sheet when the holder is connected to the upstanding support portion by the arm portion.

19. The compression device according to claim 18, wherein the arm portion that is configured to removably connect the holder to the upstanding support portion is a first arm portion, and further comprising a second arm portion that is configured to removably connect the holder to the upstanding support portion, the first arm portion extending from a first part of the upstanding support portion to a first part of the holder, the second arm portion extending from a second part of the upstanding support portion to a second part of the holder, the first part of the upstanding support portion being spaced apart from the second part of the upstanding support portion, the first part of the holder being spaced apart from the second part of the holder.

20. The compression device according to claim 18, wherein the arm portion that is configured to removably connect the holder to the upstanding support portion includes a movable portion that is movable relative to the holder in one direction approaching the holder and in an opposite direction away from the holder, the movable, the arm portion being configured to removably connect the holder to the upstanding support portion by virtue of at least one projecting portion that is removably positionable in a recessed portion.

* * * * *